United States Patent
Ritchie et al.

(10) Patent No.: US 8,409,794 B2
(45) Date of Patent: Apr. 2, 2013

(54) BIOMARKERS USEFUL FOR DIAGNOSING PROSTATE CANCER, AND METHODS THEREOF

(75) Inventors: Shawn Ritchie, Saskatoon (CA); Erin Bingham, Saskatoon (CA)

(73) Assignee: Phenomenome Discoveries Inc., Saskatoon, Saskatchewan (CA)

( * ) Notice: Subject to any disclaimer, the term of this patent is extended or adjusted under 35 U.S.C. 154(b) by 440 days.

(21) Appl. No.: 12/294,215

(22) PCT Filed: Mar. 23, 2007

(86) PCT No.: PCT/CA2007/000469
§ 371 (c)(1),
(2), (4) Date: Nov. 12, 2008

(87) PCT Pub. No.: WO2007/109881
PCT Pub. Date: Oct. 4, 2007

(65) Prior Publication Data
US 2009/0127454 A1     May 21, 2009

Related U.S. Application Data

(60) Provisional application No. 60/785,480, filed on Mar. 24, 2006.

(51) Int. Cl.
*C12Q 1/00* (2006.01)
(52) U.S. Cl. .......................................................... 435/4
(58) Field of Classification Search .................. None
See application file for complete search history.

(56) References Cited

U.S. PATENT DOCUMENTS

| 7,349,809 | B2 | 3/2008 | Goodenowe |
| 2003/0228639 | A1 | 12/2003 | Wright et al. |
| 2005/0244973 | A1* | 11/2005 | Andel et al. ................... 436/64 |
| 2007/0009970 | A1 | 1/2007 | Heller et al. |

FOREIGN PATENT DOCUMENTS

| CA | 2443806 A1 | 10/2002 |
| EP | 1270745 A2 | 1/2003 |
| JP | 2003-532055 A | 10/2003 |
| JP | 2004-500553 A | 1/2004 |
| JP | 2006-509186 A | 3/2006 |
| WO | 98/43093 A1 | 10/1998 |
| WO | 01/25791 A2 | 4/2001 |
| WO | 01/57518 A2 | 8/2001 |
| WO | 01/71360 A2 | 9/2001 |
| WO | 02/44417 A2 | 6/2002 |
| WO | 03/091695 A2 | 11/2003 |
| WO | 2004/030511 A2 | 4/2004 |

OTHER PUBLICATIONS

Tockman et al (Cancer Res., 1992, 52:2711s-2718s).*
Aharoni et al., "Nontargeted Metabolome Analysis by Use of Fourier Transform Ion Cyclotron Mass Spectrometry," OMICS A Journal of Integrative Biology 6(3):217-34 (2002).
Fan et al., "The Promise of Metabolomics in Cancer Molecular Therapeutics," Current Opinion in Molecular Therapeutics 6(6):584-92 (2004).
Glassbrook et al., "Metabolic Profiling on the Right Path," Nature Biotechnology 18:1142-43 (2000).
Grizzle et al., "Serum Protein Expression Profiling for Cancer Detection: Validation of a SELDI-based Approach for Prostate Cancer," Disease Markers 19:185-95 (2003,2004).
Tanaka et al., "Prostatic Acid Phosphatase Degrades Lysophosphatidic Acid in Seminal Plasma," FEBS Letters 571:197-204 (2004).
Troyer et al., "Promise and Challenge: Markers of Prostate Cancer Detection, Diagnosis and Prognosis," Disease Markers 20:117-28 (2004).
Gann et al., "A Prospective Evaluation of Plasma Prostate-Specific Antigen for Detection of Prostatic Cancer," American Medical Association 273(4):289-94 (1995).
Okajima et al., "Stimulatory and Inhibitory Actions of Lysophosphatidylcholine, Depending on its Fatty Acid Residue, on the Phospholipase C/Ca2+ System in HL-60," Biochem. J. 336:491-500 (1998).
Schroder et al., "Prostate Cancer Detection at Low Prostate Specific Antigen," The Journal of Urology 163:806-12 (2000).
Thompson et al., "The Influence of Finasteride on the Development of Prostate Cancer," N. Engl J Med 349(3)215-24 (2003).
Muti et al., "Urinary Estrogen Metabolites and Prostate Cancer: A Case-Control Study in the United States," Cancer Causes and Control 13:947-955 (2002).
Nithipatikom et al., "Determination of Cyclooxygenases and Arachidonic Acid Metabolites in Invasive Human Prostate Cancer Cells," Abstracts/Prostaglandins & other Lipid Mediators 59:1-235 (1999).
Supplemental European Search Report for EP 07710787, (2011).

* cited by examiner

*Primary Examiner* — Sean Aeder
(74) *Attorney, Agent, or Firm* — LeClairRyan, a Professional Corporation

(57) ABSTRACT

The present invention describes a method for predicting a health-state indicative of the presence of prostate cancer. The method measures the intensities of specific small biochemicals, called metabolites, in a blood sample from a patient with an undetermined health-state, and compares these intensities to the intensities observed in a population of healthy individuals and/or to the intensities previously observed in a population of confirmed prostate cancer-positive individuals. The method enables a practitioner to determine the probability that a screened patient is positive for prostate cancer.

30 Claims, 24 Drawing Sheets

495.3328

517.3148

521.3481

545.3460

531.3123

555.3101

565.3394

BIOMARKERS USEFUL FOR DIAGNOSING PROSTATE CANCER, AND METHODS THEREOF

This application is a national stage application under 35 U.S.C. §371 from PCT Application No. PCT/CA2007/000469, filed Mar. 23, 2007, which claims the priority benefit of U.S. Provisional Application No. 60/785,480, filed Mar. 24, 2006.

FIELD OF INVENTION

The present invention relates to small molecules or metabolites that are found to have significantly different abundances or intensities between clinically diagnosed prostate cancer-positive patients and normal patients. The present invention also relates to methods for diagnosing prostate cancer, or the risk of developing prostate cancer.

BACKGROUND OF THE INVENTION

Prostate cancer will affect one in every six men during their lifetime, with over 200,000 diagnoses and 30,000 deaths per year in the U.S. alone (1). It is the second leading cause of death due to cancer in men. Current screening methods for prostate cancer include the prostate-specific antigen (PSA) test, which detects the levels of prostate-specific antigen in a blood sample, and digital rectal examination (DRE). Although 60 to 70% of at-risk men in the U.S. have undergone PSA testing since the test was adopted, prostate cancer death rates have only slightly decreased. This is largely due to two reasons: 1) the fact that PSA testing fails to identify a subset of aggressive cancers, and 2) that only about 30% of men with a positive PSA test have a positive biopsy. Diagnosis is further complicated by the fact that of all men treated for prostate cancer, about 25% have disease recurrence and require additional treatment, while in other cases some tumors never progress at all and may be better left untreated. Therefore, a key issue with prostate cancer diagnosis today is the inability to predict the course of the disease. Together, these statistics have made prostate screening with conventional methods a controversial issue. The ideal prostate cancer biomarker(s) would therefore be suitable for early detection, as well as have the ability to predict disease aggressiveness and ideally to be able to monitor disease progression during therapy or post surgery.

Currently, PSA is recognized as the best available serum marker for prostate cancer, however, there is substantial room for improvement. The impact of PSA testing, beginning in the early 1990s, can be seen by decreases in the numbers of men diagnosed with metastasis, concurrent with overall decreased mortality (2). However, this may be due to the fact that PSA screening increased awareness of prostate cancer, which ultimately stimulated the analysis of more biopsies. Calculating the performance characteristics (sensitivity and specificity) of the PSA test is difficult because of ethnicity-related difference in incidence, and that in most studies, the percentage of biopsies performed is higher than what would normally be performed in clinical practice. In the Prostate Cancer Prevention Trial (PCPT) (3), the false-negative rate for detection of high-grade tumors was at least 15%, with a false-positive rate of 70% (i.e. only 30% of men with elevated PSA have a positive biopsy). In another study, the Physician's Health Study (4), the sensitivity for aggressive cancer over a four-year period was 87%, but dropped to 53% for non-aggressive cancers. There have been many other studies carried out to assess PSA sensitivity, but the latest findings claim overall sensitivity to be at best 73% (5). Lowering the PSA threshold would detect more cancers, but at the cost of more false-positives and subsequently more biopsies. To complicate matters further, it appears that due to increased prevalence of benign prostatic hyperplasia (BPH) in the ageing male population, the sensitivity of the PSA test with a cut-point of 4 ng/ml decreases with age.

PSA alone cannot diagnose prostate cancer. Diagnosis is a complex process, which involves integrating the results of a physical examination, a PSA test, the Gleason grade (by assessing glandular architecture at biopsy) and possibly other lab tests.

It is clear that there is a need for improving prostate cancer detection. A test that is able to detect risk for, or the presence of, prostate cancer or that can predict aggressive disease with high specificity and sensitivity would be very beneficial and would impact prostate cancer morbidity. The claimed invention describes the discovery of molecules present in serum samples which show a differential pattern of abundances between prostate cancer patients and normal individuals.

SUMMARY OF THE INVENTION

The present invention relates to small molecules or metabolites that are found to have significantly different abundances or intensities between clinically diagnosed prostate cancer-positive patients and normal patients. The present invention also relates to methods for diagnosing prostate cancer, or the risk of developing prostate cancer.

The present invention provides a method for identifying, validating, and implementing a high-throughput screening (HTS) assay for the diagnosis of a health-state indicative of prostate cancer. In a particular example, the method encompasses the analysis of prostate cancer-specific and normal biological samples using non-targeted FTMS technology to identify all statistically significant metabolite features which differ between normal and prostate cancer-positive biological samples, followed by the selection of the optimal feature subset using statistics and chemical properties of the molecules, and characterization of the feature set using methods including, but not limited to, chromatographic separation, mass spectrometry (MS/MS), and nuclear magnetic resonance (NMR), for the purposes of:

1. separating and identifying retention times of the metabolites;
2. producing descriptive MS/MS fragmentation patterns specific for each metabolite;
3. characterization of molecular structures; and
4. developing a high-throughput quantitative or semi-quantitative MS/MS-based diagnostic assay.

The present invention further provides a method for the diagnosis of prostate cancer or the risk of developing prostate cancer in humans by measuring the levels of specific small molecules present in a sample and comparing them to "normal" reference levels. The methods measure the intensities of specific small molecules, also referred to as metabolites, in the sample from the patient and compare these intensities to the intensities observed in a population of healthy individuals.

The present invention provides a method of identifying one or more than one metabolite marker for diagnosing prostate cancer, comprising the steps of:

a) introducing one or more than one sample from one or more than one patient with prostate cancer, said sample containing a plurality of metabolites into a high resolution mass spectrometer b) obtaining quantifying data for the metabolites;

c) creating a database of said quantifying data;
d) comparing the identifying and quantifying data from the sample with corresponding data from a sample from one or more than one reference sample; and
e) identifying one or more than one metabolite marker that differs between said sample and said one or more than one reference sample.

The metabolite markers are selected from the metabolites listed in Table 1, or any combination thereof. The method may further comprise selecting a minimal number of metabolite markers needed for optimal diagnosis. The high resolution mass spectrometer may be a Fourier Transform Ion Cyclotron Resonance Mass Spectrometer (FTMS).

The present invention also provides a method for diagnosing prostate cancer or the risk of prostate cancer in a patient, the method comprising the steps of:
a) obtaining a sample from said patient;
b) analyzing said sample to obtain quantifying data for one or more than one metabolite marker;
c) comparing the quantifying data for said one or more than one metabolite marker to corresponding data obtained from one or more than one reference sample; and
d) using said comparison to differentially diagnose prostate cancer or the risk of prostate cancer.

The one or more than one metabolite marker is selected from the metabolites listed in Table 1, or any combination thereof. The diagnostic method above may comprise analyzing the sample by liquid chromatography mass spectrometry (LC-MS) in step b). Alternatively, when the method is a high throughput method, step b) may comprise analyzing the sample by either liquid chromatography or direct injection followed by linear ion trap tandem mass spectrometry.

In the method as described above, the one or more than one reference sample may be a plurality of samples obtained from control individuals; one or more than one baseline sample obtained from the patient at an earlier date; or a combination thereof.

In another embodiment of the present invention, there is provided a method for diagnosing prostate cancer or the risk of prostate cancer in a patient, the method comprising the steps of:
a) obtaining a sample from said patient;
b) analyzing said sample to obtain quantifying data for one or more than one metabolite marker;
c) obtaining a ratio for each of the one or more than one metabolite marker to an internal control metabolite;
d) comparing each ratio of said one or more than one metabolite marker to the internal control metabolite to corresponding data obtained from one or more than one reference sample; and
e) using said comparison to diagnose prostate cancer or the risk of prostate cancer.

The diagnostic method above may comprise one or more than one metabolite marker selected from metabolites listed in Table 1, or any combination thereof. The diagnostic method above may comprise analyzing the sample by liquid chromatography mass spectrometry (LC-MS) in step b). Alternatively, when the method is a high throughput method, step b) may comprise analyzing the sample by either direct injection or liquid chromatography and linear ion trap tandem mass spectrometry.

In the method as described above, the one or more than one reference sample may be a plurality of samples obtained from control individuals; one or more than one baseline sample obtained from the patient at an earlier date; or a combination thereof.

The present invention further provides a method for evaluating the efficacy of a therapy for treating prostate cancer in a patient, comprising:
a) obtaining a sample from said patient;
b) analyzing said sample to obtain quantifying data for one or more than one metabolite marker;
c) comparing said quantifying data to corresponding data obtained from one or more than one reference sample; and
d) using said comparison to determine whether the therapy is improving the health state of the patient,
wherein the one or more than one metabolite marker is selected from metabolites listed in Table 1, or any combination thereof. The diagnostic method above may comprise analyzing the sample by liquid chromatography mass spectrometry (LC-MS) in step b). Alternatively, when the method is a high throughput method, step b) may comprise analyzing the sample by direct injection or liquid chromatography and linear ion trap tandem mass spectrometry.

In the method as described above, the one or more than one reference sample may be a plurality of samples obtained from control individuals; one or more than one pre-therapy baseline sample obtained from the patient; or a combination thereof.

In yet another embodiment of the present invention, there is provided a method for evaluating the efficacy of a therapy for treating prostate cancer in a patient, comprising:
a) obtaining a sample from said patient;
b) analyzing said sample to obtain quantifying data for one or more than one metabolite marker;
c) obtaining a ratio for each of the one or more than one metabolite marker to an internal control metabolite;
d) comparing each ratio of said one or more than one metabolite marker to the internal control metabolite to corresponding data obtained from one or more than one reference sample; and
e) using said comparison to determine whether the therapy is improving the health state of the patient,
wherein the one or more than one metabolite marker is selected from metabolites listed in Table 1, or any combination thereof. The diagnostic method above may comprise analyzing the sample by liquid chromatography mass spectrometry (LC-MS) in step b). Alternatively, when the method is a high throughput method, step b) may comprise analyzing the sample by direct injection or liquid chromatography and linear ion trap tandem mass spectrometry.

In the method as described above, the one or more than one reference sample may be a plurality of samples obtained from control individuals; one or more than one pre-therapy baseline sample obtained from the patient; or a combination thereof.

The methods described herein may be combined with other methods for monitoring prostate cancer, for example the PSA test.

In the diagnostic methods and methods of evaluating the efficacy of treatment as described above, the one or more than one metabolite marker may be selected from the group consisting of lysophospholipids, including lysophosphatidylcholines, lysophosphatidylethanolamines, lysophosphatidyldimethylethanolamines, lysophosphatidylserines, lysosphingosylphosphorylcholines, lysophosphatidylglycerols lysophosphatidylinositols, platelet activating factors (PAFs), and combinations thereof. For example, the one or more than one metabolite marker may comprise metabolites with accurate masses measured in Daltons of, or substantially equivalent to, a) 495.3328, b) 517.3148, c) 519.3328, d) 521.3480, e) 523.3640, f) 541.3148, g) 545.3460, h)

481.3171, i) 531.3123, j) 541.3422, k) 555.3101, l) 565.3394, m) 567.3546, and n) 569.3687. In methods where the quantifying data for the one or more than one metabolite is compared, these metabolites are observed to be decreased in patients with prostate cancer. In methods where a ratio for the one or more than one metabolite to the internal control metabolite is compared, the ratio of metabolite to internal control metabolite is decreased in patients with prostate cancer.

The metabolites a) to g) are lysophosphatidylcholine-related compounds and metabolites h) to n) are putatively N,N-dimethyl lysophosphatidylethanolamine-related compounds. Metabolites a) to n) may be further characterized by an MS/MS spectrum as shown in a) FIG. 7, and/or as described in Table 3; b) FIG. 8, and/or as described in Table 4; c) FIG. 9, and/or as described in Table 5; d) FIG. 10, and/or as described in Table 6; e) FIG. 11, and/or as described in Table 7; f) FIG. 12, and/or as described in Table 8; g) FIG. 13, and/or as described in Table 9; h) FIG. 14, and/or as described in Table 12; i) FIG. 15, and/or as described in Table 13; j) FIG. 16, and/or as described in Table 14; k) FIG. 17, and/or as described in Table 15; l) FIG. 18, and/or as described in Table 16; m) FIG. 19, and/or as described in Table 17; and n) FIG. 20, and/or as described in Table 18, respectively.

Additionally, the one or more than one metabolite above may be further characterized by molecular formula a) $C_{24}H_{50}NO_7P$, b) $C_{26}H_{48}NO_7P$, c) $C_{26}H_{50}NO_7P$, d) $C_{26}H_{52}NO_7P$, e) $C_{26}H_{54}NO_7P$, f) $C_{28}H_{48}NO_7P$, g) $C_{28}H_{52}NO_7P$, h) $C_{23}H_{48}NO_7P$, i) $C_{30}H_{46}NO_5P$, j) $C_{25}H_{52}NO_9P$, k) $C_{25}H_{50}NO_{10}P$, l) $C_{27}H_{52}NO_9P$, m) $C_{27}H_{54}NO_9P$, and n) $C_{27}H_{56}NO_9P$, respectively. The structures of the one or more than one metabolite may be characterized as follows:

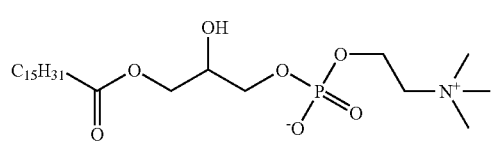

a)

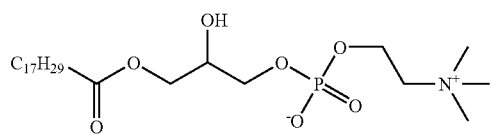

b)

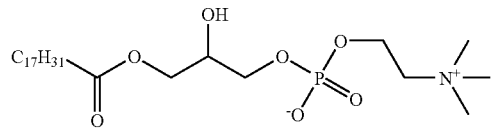

c)

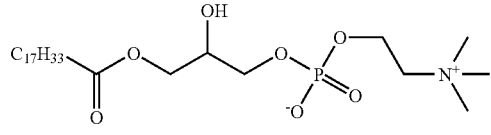

d)

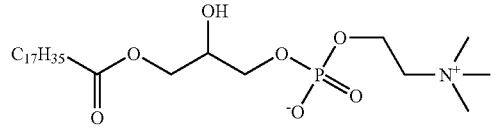

e)

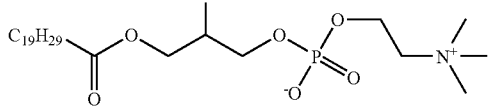

f)

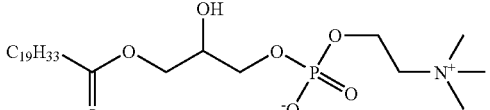

g)

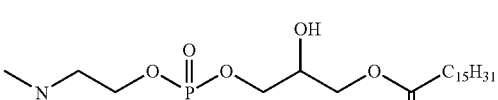

h)

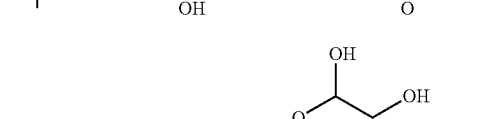

j)

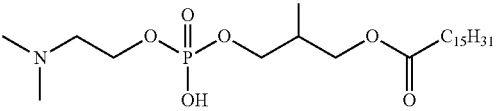

k)

l)

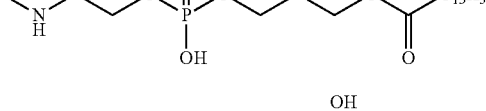

m)

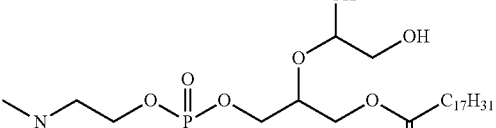

and

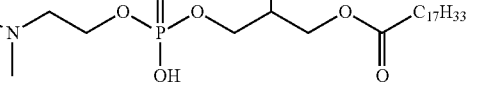

n)

respectively.

The present invention also provides novel compounds. These compounds are selected from the group consisting of the metabolites with accurate masses measured in Daltons of, or substantially equivalent to, a) 531.3123, b) 541.3422, c) 555.3101, d) 565.3394, e) 567.3546, and f) 569.3687.

The compounds described above may be further characterized by an MS/MS spectrum as shown in
a) FIG. 15, and/or as described in Table 13;
b) FIG. 16, and/or as described in Table 14;
c) FIG. 17, and/or as described in Table 15;
d) FIG. 18, and/or as described in Table 16;
e) FIG. 19, and/or as described in Table 17; and
f) FIG. 20, and/or as described in Table 18, respectively.

Likewise the compounds described above may be further characterized by an MS/MS spectrum as shown in tables 12 through 18, respectively.

The compounds may also be further characterized by molecular formula a) $C_{30}H_{46}NO_5P$, b) $C_{25}H_{52}NO_9P$, c) $C_{25}H_{50}NO_{10}P$, d) $C_{27}H_{52}NO_9P$, e) $C_{27}H_{54}NO_9P$, and f) $C_{27}H_{56}NO_9P$, respectively. In addition, the compounds described above may be characterized by the putative structures

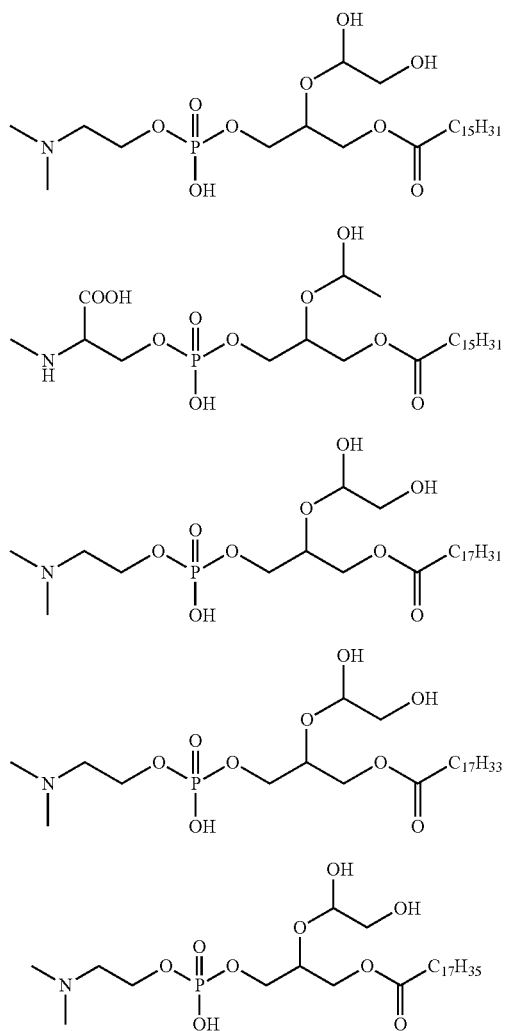

respectively.

The novel compounds of the present invention may be used for the diagnosis of prostate cancer, or for evaluating the efficacy of treatment of prostate cancer in a patient.

The present invention may significantly impact the ability to detect prostate cancer or the risk of developing prostate cancer, and may save lives. The statistical performance of a test based on these samples suggests that the test will outperform the PSA test, the only other serum-based diagnostic test for prostate cancer. Alternatively, a combination of the methods described herein and the PSA test may improve the overall diagnostic performance of each test.

The methods of the present invention, including HTS assays, can be used for the following, wherein the specific "health-state" refers to, but is not limited to prostate cancer:

1. identifying small-molecule metabolite biomarkers which can discriminate between prostate cancer-positive and prostate cancer-negative individuals using any biological sample, such as a serum sample, taken from the individual;

2. specifically diagnosing prostate cancer using metabolites identified in a sample such as serum, plasma, whole blood, and/or other tissue biopsy as described herein;

3. selecting the minimal number of metabolite features required for optimal diagnostic assay performance statistics using uni- or multivariate statistical methods and relevant chemical information about the molecules such as those mentioned herein;

4. identifying structural characteristics of biomarker metabolites selected from non-targeted metabolomic analysis using LC-MS/MS, $MS^n$ and NMR;

5. developing a high-throughput triple-quadrupole MS/MS method for assaying selected metabolite levels in a sample;

6. diagnosing prostate cancer, or the risk of developing prostate cancer, by determining the levels of any combination of metabolite features disclosed from the FTMS analysis of patient sample, using any method including but not limited to mass spectrometry, NMR, UV detection, ELISA (enzyme-linked immunosorbant assay), chemical reaction, image analysis, or other;

7. monitoring any therapeutic treatment of prostate cancer, including drug (chemotherapy), radiation therapy, surgery, dietary, lifestyle effects or other; and/or 9. longitudinal monitoring or screening of the general population for prostate cancer using any single or combination of features disclosed in the method.

The impact of the present invention on the diagnosis of prostate cancer would be tremendous, as literally everyone could be screened longitudinally throughout their lifetime to assess risk. Given that the performance characteristics of the test of the present invention are representative for the general population, this test alone may be superior to any other currently available screening method, as it may have the potential to detect disease progression prior to the emergence of clinical symptoms.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1:
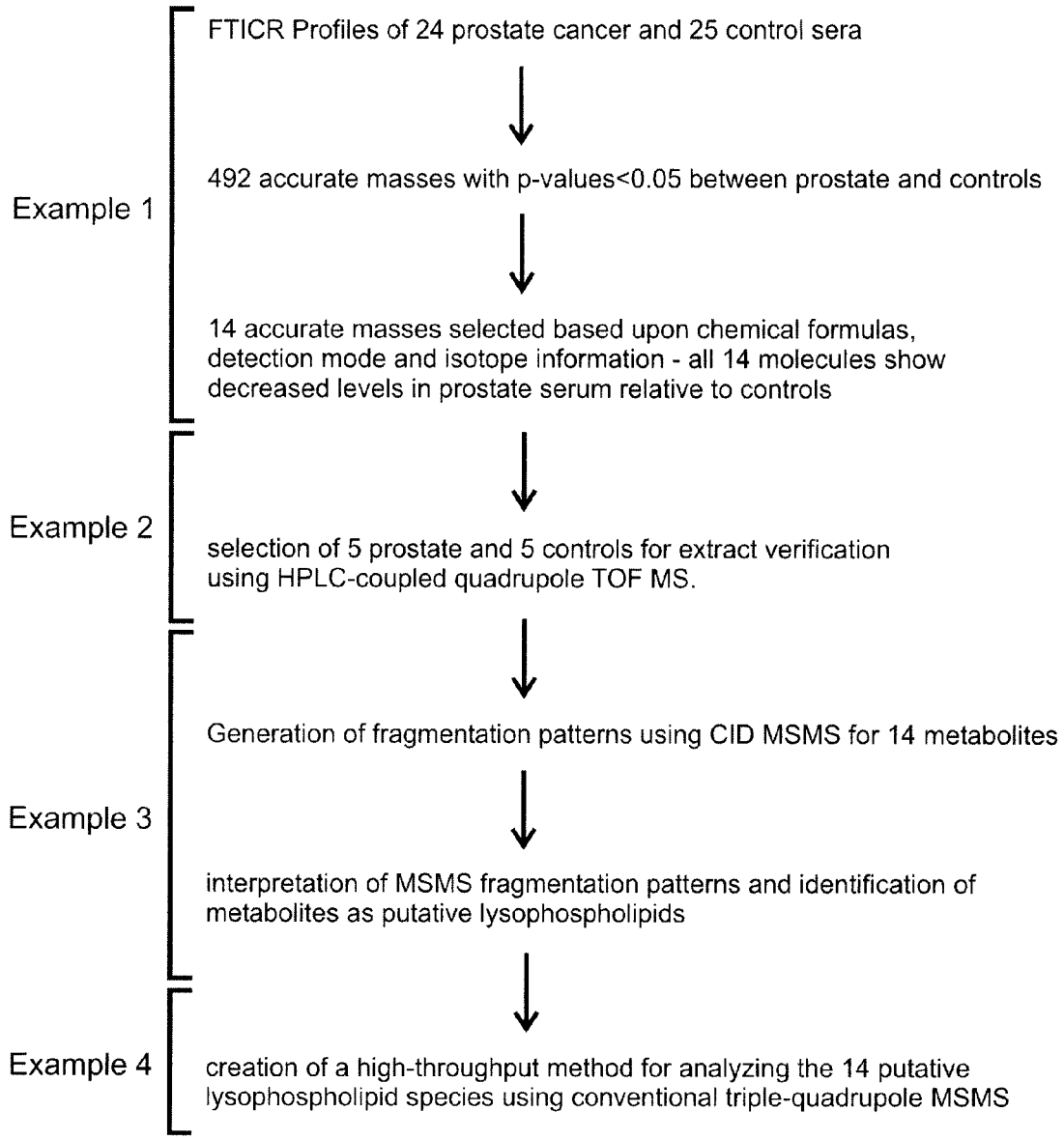
FIG. 1 shows a summary of the steps involved in the discovery, identification and characterization of metabolites, including those relating to lysophospholipid species, which are associated with the presence of prostate cancer.

The present invention relates to small molecules or metabolites that are found to have significantly different abundances or intensities between clinically diagnosed prostate cancer-positive patients and normal patients. The present invention also relates to methods for diagnosing prostate cancer, or the risk of developing prostate cancer.

The present invention provides novel methods for discovering, validating, and implementing a diagnosis method for prostate cancer. In one embodiment of the present invention, there is provided a method for identifying specific biomarkers for diagnosing prostate cancer comprising the steps of: introducing one or more than one sample from one or more than one patient with prostate cancer, said sample containing a plurality of metabolites into a high resolution mass spectrometer (for example, and without wishing to be limiting, a Fourier Transform Ion Cyclotron Resonance Mass Spectrometer (FTMS)); obtaining, identifying and quantifying data for the metabolites; creating a database of said quantifying data; comparing the quantifying data from the sample with corresponding data obtained from one or more than one sample from a control patient; identifying one or more than one metabolites that differ. The metabolite markers identified using the method of the present invention may include the metabolites listed in Table 1. The method may further comprise selecting the minimal number of metabolite markers needed for optimal diagnosis.

In order to determine the biochemical markers of a given health-state in a particular population, a group of patients representative of the health state (i.e., a particular disease) and/or a group of "normal" or "control" counterparts (i.e., individuals that do not suffer from the particular health state) are required. Biological samples taken from the patients in the particular health state can then be compared to the same samples taken from the normal population as well as to patients in similar health-state category in the hopes of identifying biochemical differences between the two groups, by analyzing the biochemicals present in the samples using analytical methods including, but not limited to, FTMS and/or LC-MS.

The method for the discovery of metabolite markers as described above may be done using non-targeted metabolomic strategies or methods. Multiple non-targeted metabolomics strategies have been described in the scientific literature including NMR (6), GC-MS (7), LC-MS (8), and FTMS strategies (9-11). The metabolic profiling strategy employed for the discovery of differentially expressed metabolites in the present invention was the non-targeted FTMS strategy by Phenomenome Discoveries [21, 24-27; see also US Published Application No. 2004-0029120 A1, Canadian Application No. 2,298,181, and WO 0157518]. Non-targeted analysis involves the measurement of as many molecules in a sample as possible, without any prior knowledge or selection of components prior to the analysis. Therefore, the potential for non-targeted analysis to discover novel metabolite biomarkers is high versus targeted methods, which detect a predefined list of molecules. The present invention uses a non-targeted method to identify metabolite components in serum samples that differ between individuals with prostate cancer and control individuals (i.e., individuals that do not have prostate cancer).

However, a person skilled in the art would recognize that other metabolite profiling strategies could be used to discover some or all of the differentially regulated metabolites disclosed in the present invention and that the metabolites described herein, however discovered or measured, represent unique chemical entities that are independent of the analytical technology that may be used to detect and measure them. For example, and without wishing to be limiting in any manner, other methods of metabolite detection could be used, for example other MS-based platforms, ELISAs, colorimetric assays, etc.

The present invention also provides a method for diagnosing prostate cancer or the risk of developing prostate cancer in a patient, the method comprising the steps of:
  a) obtaining a sample from said patient;
  b) analyzing said sample to obtain quantifying data for one or more than one metabolite marker;
  c) comparing the quantifying data for said one or more than one metabolite marker to corresponding data obtained from one or more than one reference sample; and
  d) using said comparison to diagnose prostate cancer or the risk of developing prostate cancer.

The step of analyzing the sample (step b) may comprise analyzing the sample using a mass spectrometer (MS). For example, and without wishing to be limiting, such mass spectrometer could be of the FTMS, orbitrap, time-of-flight (TOF) or quadrupole types. Alternatively, the mass spectrometer could be equipped with an additional pre-detector mass filter. For example, and without wishing to be limiting such instruments are commonly referred to as quadrupole-FTMS (Q-FTMS), quadrupole-TOF (Q-TOF) or triple quadrupole (TQ or QQQ). In addition, the mass spectrometer could be operated in either the parent ion detection mode (MS) or in MSn mode, where n>=2. MSn refers to the situation where the parent ion is fragmented by collision induced dissociation (CID) or other fragmentation procedures to create fragment ions, and then one or more than one of said fragments are detected by the mass spectrometer. Such fragments can then be further fragmented to create further fragments. Alternatively, the sample could be introduced into the mass spectrometer using a liquid or gas chromatographic system or by direct injection.

In the methods of the present invention, any type of biological sample that originates from anywhere within the body, for example but not limited to, blood (serum/plasma), CSF, urine, stool, breath, saliva, or biopsy of any solid tissue including tumor, adjacent normal, smooth and skeletal muscle, adipose tissue, liver, skin, hair, brain, kidney, pancreas, lung, colon, stomach, or other may be used. Of particular interest are samples that are serum. While the term "serum" is used herein, those skilled in the art will recognize that plasma or whole blood or a sub-fraction of whole blood may also be used.

The biological samples may be obtained in both normal and prostate cancer-positive groups from a diverse population of individuals, ranging in age, ethnicity, weight, occupation, and displaying varying non-prostate cancer-related health-states. Choosing subjects in this way introduces more variability into a dataset, however, reduces potential confounding bias that ultimately results in a more robust set of biomarkers (since it can still detect disease in the presence of many other variables).

In a non-limiting example, when a blood sample is drawn from a patient there are several ways in which the sample can be processed. The range of processing can be as little as none (i.e. frozen whole blood) or as complex as the isolation of a particular cell type. The most common and routine procedures involve the preparation of either serum or plasma from whole blood. All blood sample processing methods, including spotting of blood samples onto solid-phase supports, such as filter paper or other immobile materials, are also contemplated by the present invention.

Without wishing to be limiting in any manner, the processed blood or serum or sample described above may then be further processed to make it compatible with the methodical analysis technique to be employed in the detection and measurement of the metabolites contained within the processed serum or blood sample. The types of processing can range from as little as no further processing to as complex as differential extraction and chemical derivatization. Extraction methods could include sonication, soxhlet extraction, microwave assisted extraction (MAE), supercritical fluid extraction (SFE), accelerated solvent extraction (ASE), pressurized liquid extraction (PLE), pressurized hot water extraction (PHWE) and/or surfactant assisted extraction (PHWE) in common solvents such as methanol, ethanol, mixtures of alcohols and water, or organic solvents such as ethyl acetate or hexane. A method of particular interest for extracting metabolites for FTMS non-targeted analysis as well as for direct injection on triple quadrupole mass spectrometers, is to perform a liquid/liquid extraction whereby non-polar metabolites dissolve in an organic solvent and polar metabolites dissolve in an aqueous solvent.

The extracted samples may be analyzed using any suitable method known in the art. For example, and without wishing to be limiting in any manner, extracts of biological samples are amenable to analysis on essentially any mass spectrometry platform, either by direct injection or following chromatographic separation. Typical mass spectrometers are comprised of a source which ionizes molecules within the sample, and a detector for detecting the ionized molecules or fragments of molecules. Non-limiting examples of common sources include electron impact, electrospray ionization (ESI), atmospheric pressure chemical ionization (APCI), atmospheric pressure photo ionization (APPI), matrix assisted laser desorption ionization (MALDI), surface enhanced laser desorption ionization (SELDI), and derivations thereof. Common mass separation and detection systems can include quadrupole, quadrupole ion trap, linear ion trap, time-of-flight (TOF), magnetic sector, ion cyclotron (FTMS), Orbitrap, and derivations and combinations thereof. The advantage of FTMS over other MS-based platforms is its high resolving capability that allows for the separation of metabolites differing by only hundredths of a Dalton, many of which would be missed by lower resolution instruments.

By the term "metabolite", it is meant specific small molecules, the levels or intensities of which are measured in a sample, and that may be used as markers to diagnose a disease state. These small molecules may also be referred to herein as "metabolite marker", "metabolite component", "biomarker", "biochemical marker", or "metabolite feature".

The metabolites are generally characterized by their accurate mass, as measured by mass spectrometry technique used in the above method. The accurate mass may also be referred to as "accurate neutral mass" or "neutral mass". The accurate mass of a metabolite is given herein in Daltons (Da), or a mass substantially equivalent thereto. By "substantially equivalent thereto", it is meant that a +/−5 ppm (part per million) difference in the accurate mass would indicate the same metabolite, as would be recognized by a person of skill in the art. The mass accuracy is the difference which is observed between the theoretical mass and a measured mass: delta mass accuracy ($\Delta m$)=mreal−mmeasured, which is often expressed in parts per million (ppm). Ppm is defined as 1,000,000*$\Delta m$ accuracy/mmeasured (for example, theoretical mass: 1000, measured mass: 999.9 error: 100 ppm).

The accurate mass is given as the mass of the neutral metabolite. As would be recognized by a person of skill in the art, the ionization of the metabolites, which occurs during analysis of the sample, the metabolite will cause either a loss or gain of one or more hydrogen atoms and a loss or gain of an electron. This changes the accurate mass to the "ionized mass", which differs from the accurate mass by the mass of hydrogens and electrons lost or gained during ionization. Unless otherwise specified, the accurate neutral mass will be referred to herein.

Similarly, when a metabolite is described by its molecular formula or structure, the molecular formula or structure of the neutral metabolite will be given, unless otherwise specified. Naturally, the molecular formula or structure of the ionized metabolite will differ from the neutral molecular formula or structure by the number of hydrogens lost or gained during ionization.

Data is collected during analysis and quantifying data for one or more than one metabolite is obtained. "Quantifying data" is obtained by measuring the levels or intensities of specific metabolites present in a sample. The measurement itself could be a relative measurement (e.g. comparison of intensity to another sample or distribution), or a quantitative measurement (e.g. a concentration such as X mg/ml).

The quantifying data is compared to corresponding data from one or more than one reference sample. The "reference sample", also referred to herein as a "control sample", is any suitable reference sample for the particular disease state. For example, and without wishing to be limiting in any manner, in the present invention the reference sample may be a sample from a control individual, i.e., a person not suffering from prostate cancer (also referred to herein as a "normal", "control", or "reference" individual or patient); the reference sample may also be a sample obtained from a patient with prostate cancer. As would be understood by a person of skill in the art, more than one reference sample may be used for comparison to the quantifying data. For example and without wishing to be limiting, the one or more than one reference sample may be a first reference sample obtained from a control individual. The one or more than one reference sample may also be a sample obtained from a patient at an earlier date; this would allow longitudinal monitoring of a patient's health state throughout their lifetime. Such samples could be collected over successive intervals of time. In another example, the reference sample could also be obtained from a patient with prostate cancer prior to therapy (i.e., pre-therapy) in order to monitor the efficacy of the therapy administered. A person of skill in the art would also recognize that a combination of such reference samples could be used in the methods of the present invention.

The present invention also provides novel compounds, identified using the methods of the present invention. The novel compounds may be used as metabolite markers in the diagnosis of prostate cancer or the risk of developing prostate cancer, as described above.

In one embodiment, the compounds may be selected from the metabolites listed in Table 1, or any combination thereof. An optimal panel of metabolites may be selected from the group of 492 metabolites shown in Table 1. For example, and without wishing to be limiting, the optimal panel of metabolite markers may be metabolites with accurate masses (measured in Daltons) of 519.3328, 541.3148, 545.3460, 555.3101, 541.3422, 565.3394, 521.3480, 517.3148, 567.3546, 523.3640, 531.3123, 481.3171, 495.3328, 569.3687, where a +/−5 ppm difference would indicate the same metabolite. In particular, it is presently shown that the 14 metabolites just described, when measured in serum or tissue, show a lower concentration in prostate cancer-positive subjects relative to control (disease-free) individuals.

The 14 metabolite markers described above can be categorized into one of two groups, based on their detection in an aqueous extract and their propensity to ionize either positively or negatively. The metabolites with accurate masses (measured in Daltons) of 0495.3328, 517.3148, 519.3328, 521.3480, 523.3640, 541.3148, and 545.3460, where a +/−5 ppm difference would indicate the same metabolite, were detected as positive ions using methods presently described; metabolites with accurate masses (measured in Daltons) of 481.3171, 531.3123, 541.3422, 555.3101, 565.3394, 567.3546, and 569.3687, where a +/−5 ppm difference would indicate the same metabolite, were detected as negative ions using the methods presently described.

The 14 metabolites described above relate to metabolites of the lysophospholipid class, for example, lysophosphatidylcholine, lysophosphatidylethanolamines, lysophosphatidyldimethylethanolamines, lysophosphatidylserines, lysosphingosylphosphorylcholines, lysophosphatidylglycerols, lysophosphatidylinositols, platelet activating factors (PAFs), and combinations thereof.

The concentration of specific metabolites described above, including lysophospholipid species, is detected in order to diagnose prostate cancer or the risk of prostate cancer. Any combination of the above metabolites could be measured simultaneously, in a serial manner, or in different combinations to arrive at a diagnostic output.

Structural characterization of the above metabolites may be carried out using methods well known to those skilled in the area. The principal characteristics that may be used to characterize the metabolites may include, but are not limited to accurate mass, molecular formula, polarity, acid/base properties, NMR spectra, and MS/MS or MSn spectra. Techniques used to determine these characteristics include, but are not limited to reverse phase LC-MS using a C18 column followed by analysis by MS, MS/MS fragmentation using collision induced dissociation (CID), NMR, and extraction. The data obtained can be used as fingerprints or unique identifiers of a particular metabolite under the experimental conditions specified. Any or all of the metabolites described by the present application may be fingerprinted under various conditions to provide additional information on the metabolites, for example, the structure or nature of the molecule.

Figure 7:
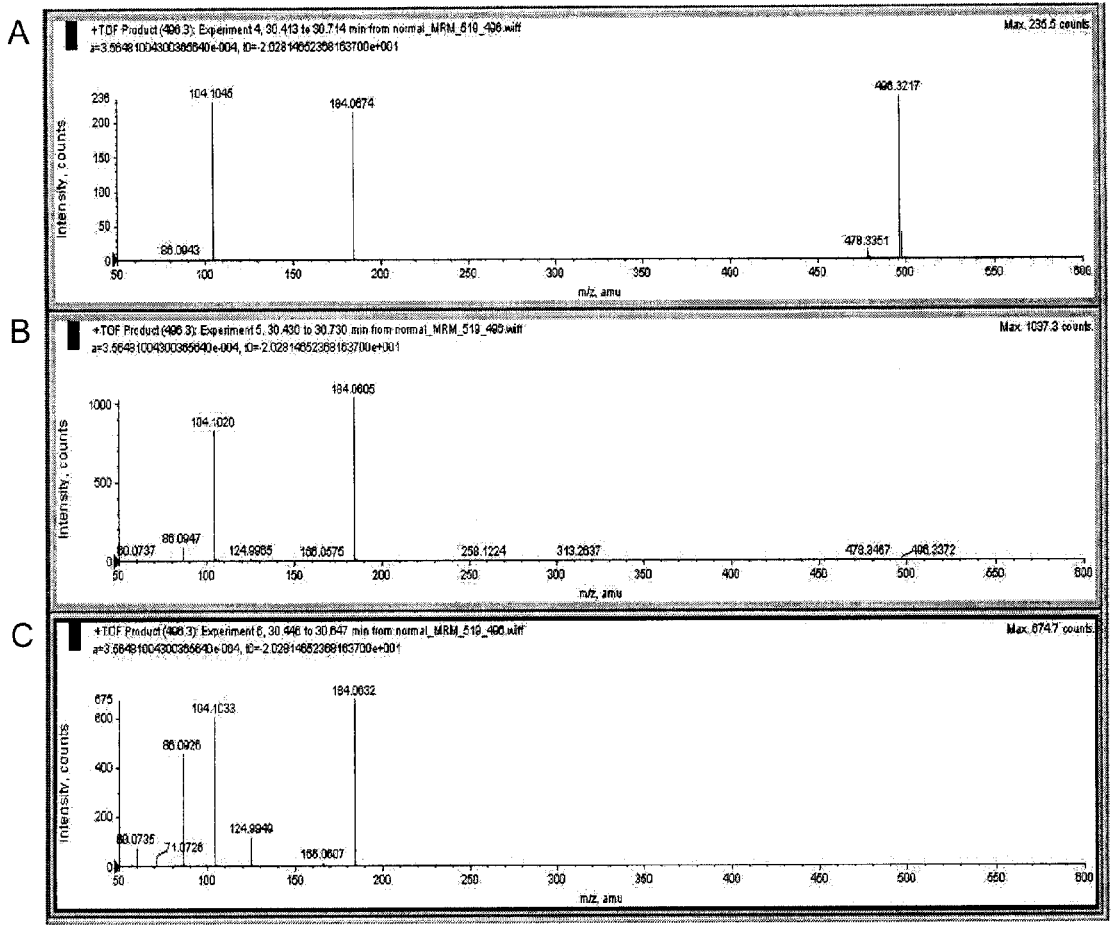
FIG. 7 shows the MS/MS extracted mass spectra for 495.3328 (496.3401 [M+H]), at collision energy voltages of 20 (A), 35 (B) and 50 (C) volts, respectively.
Figure 8:
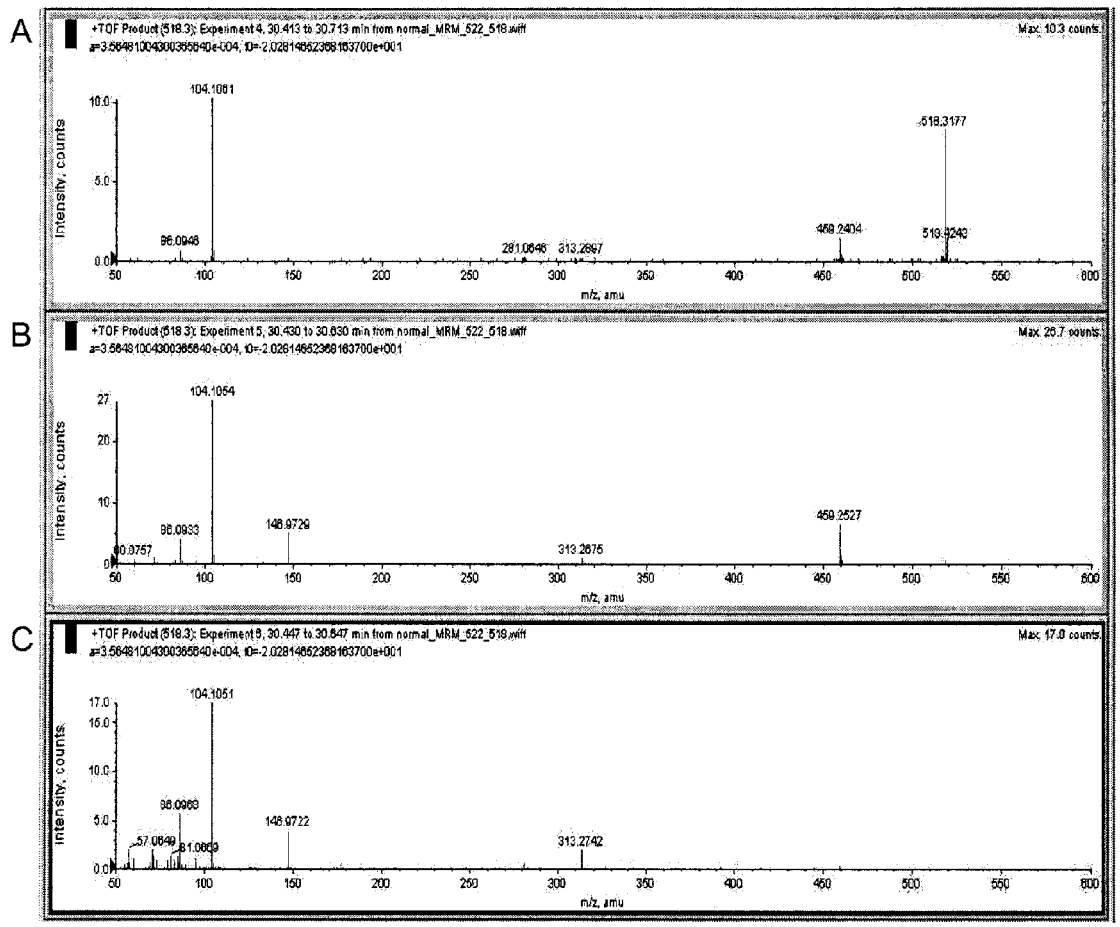
FIG. 8 shows the MS/MS extracted mass spectra for 517.3148 (518.3219 [M+H]), at collision energy voltages of 20 (A), 35 (B) and 50 (C) volts, respectively.
Figure 9:
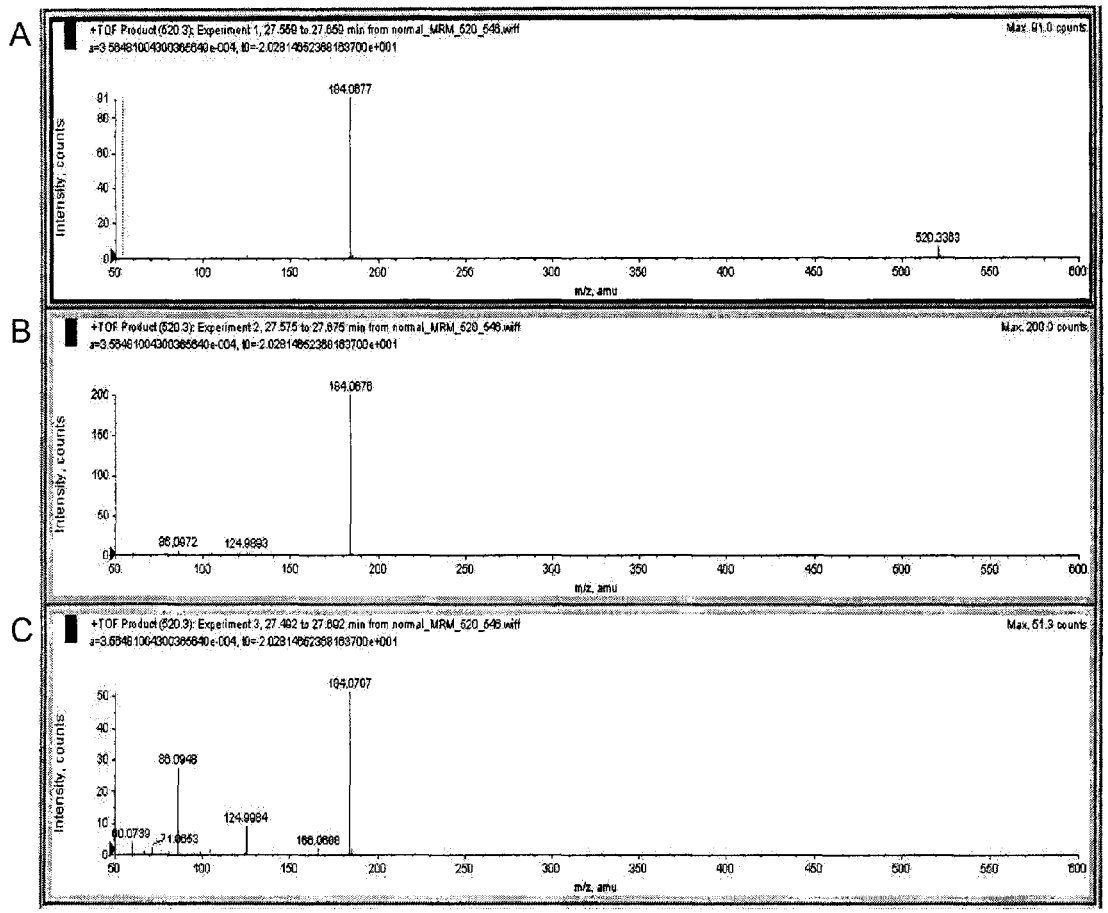
FIG. 9 shows the MS/MS extracted mass spectra for 519.3328 (520.3401 [M+H]), at collision energy voltages of 20 (A), 35 (B) and 50 (C) volts, respectively.
Figure 10:
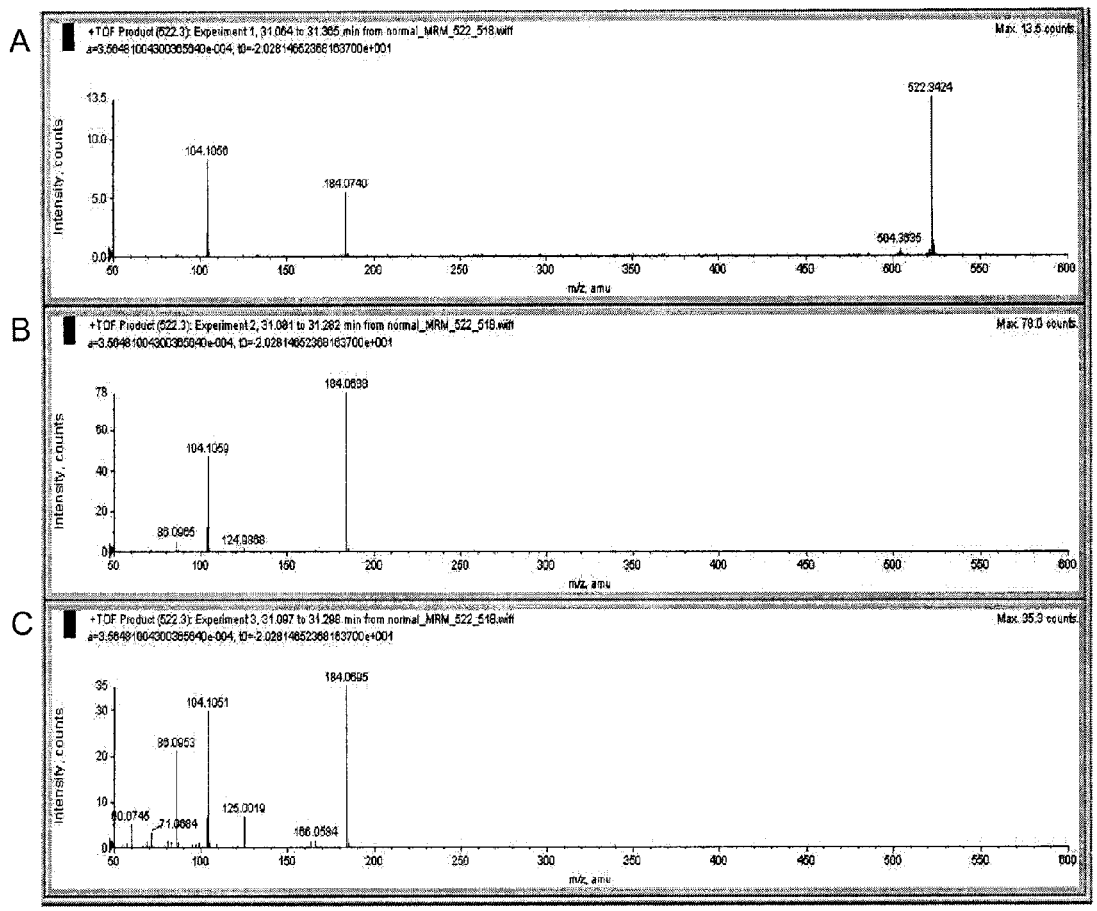
FIG. 10 shows the MS/MS extracted mass spectra for 521.3480 (522.3554 [M+H]), at collision energy voltages of 20 (A), 35 (B) and 50 (C) volts, respectively.
Figure 11:
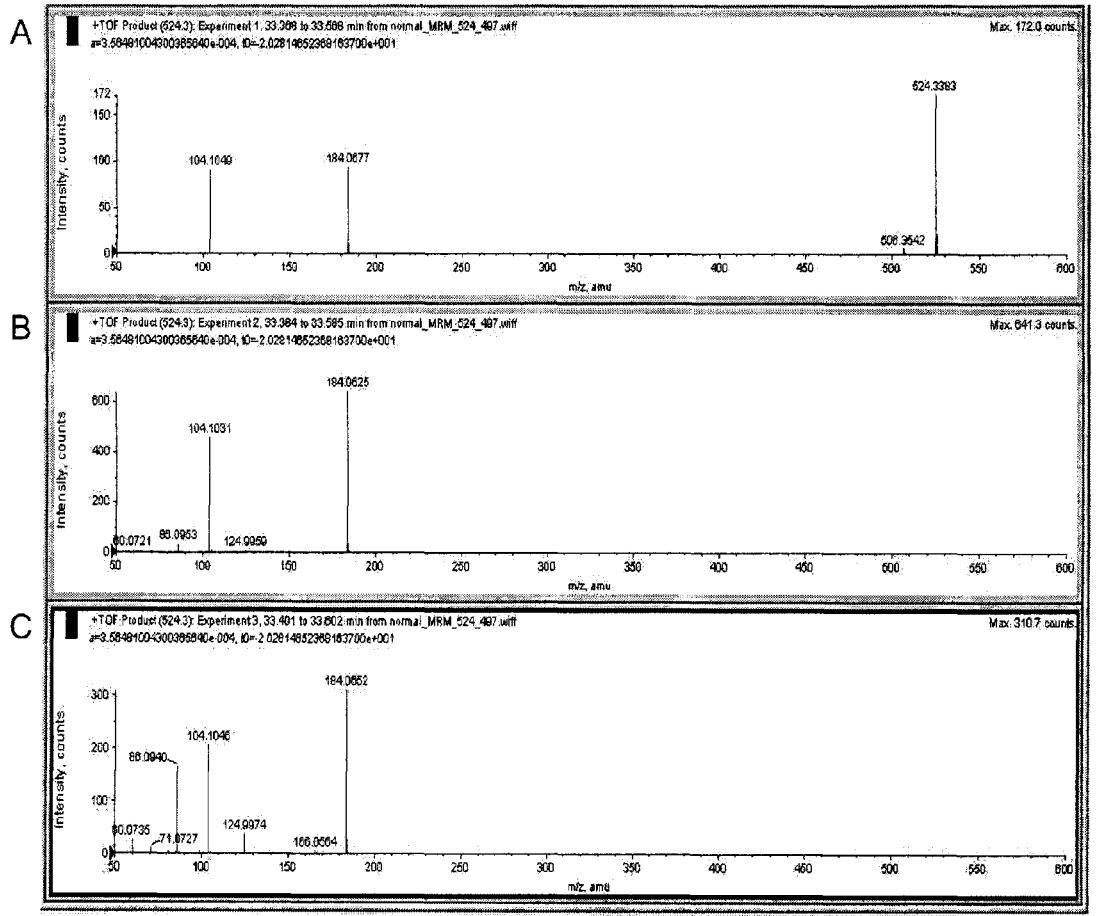
FIG. 11 shows the MS/MS extracted mass spectra for 523.3640 (524.3713 [M+H]), at collision energy voltages of 20 (A), 35 (B) and 50 (C) volts, respectively.
Figure 12:
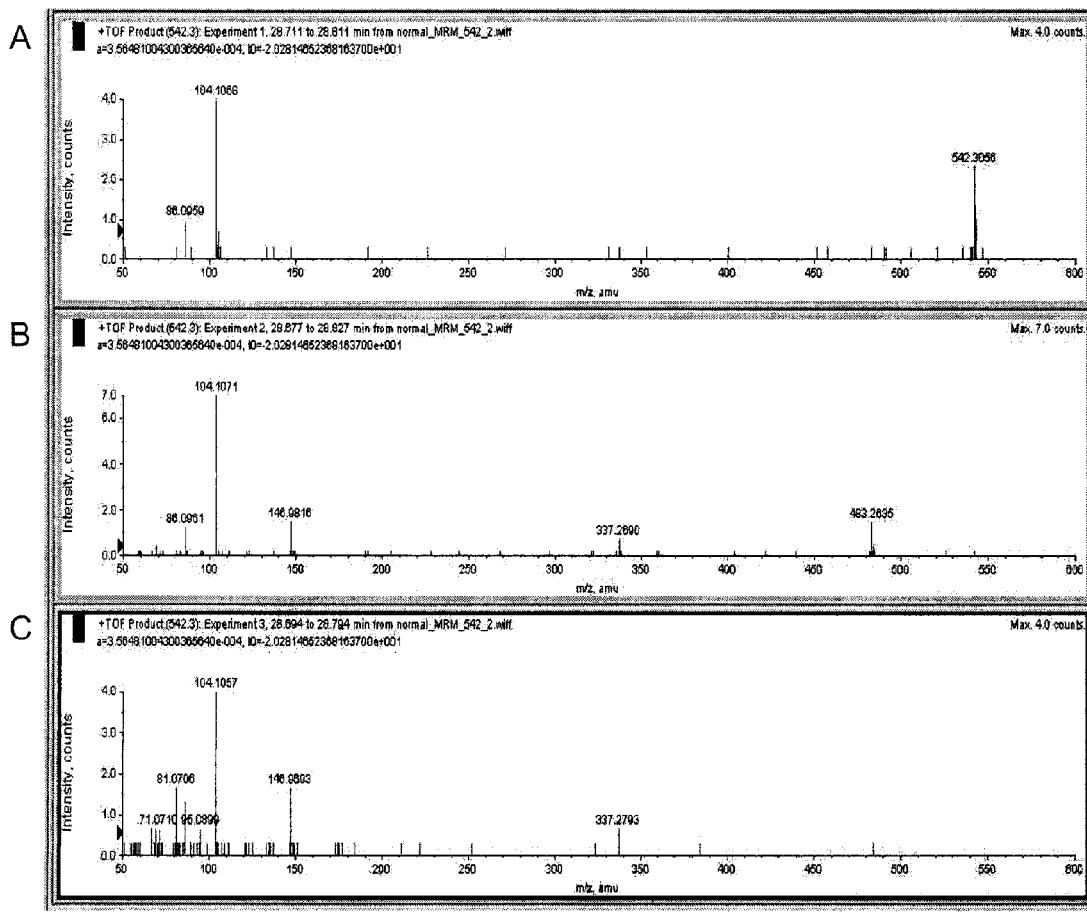
FIG. 12 shows the MS/MS extracted mass spectra for 541.3148 (542.3219 [M+H]), at collision energy voltages of 20 (A), 35 (B) and 50 (C) volts, respectively.
Figure 13:
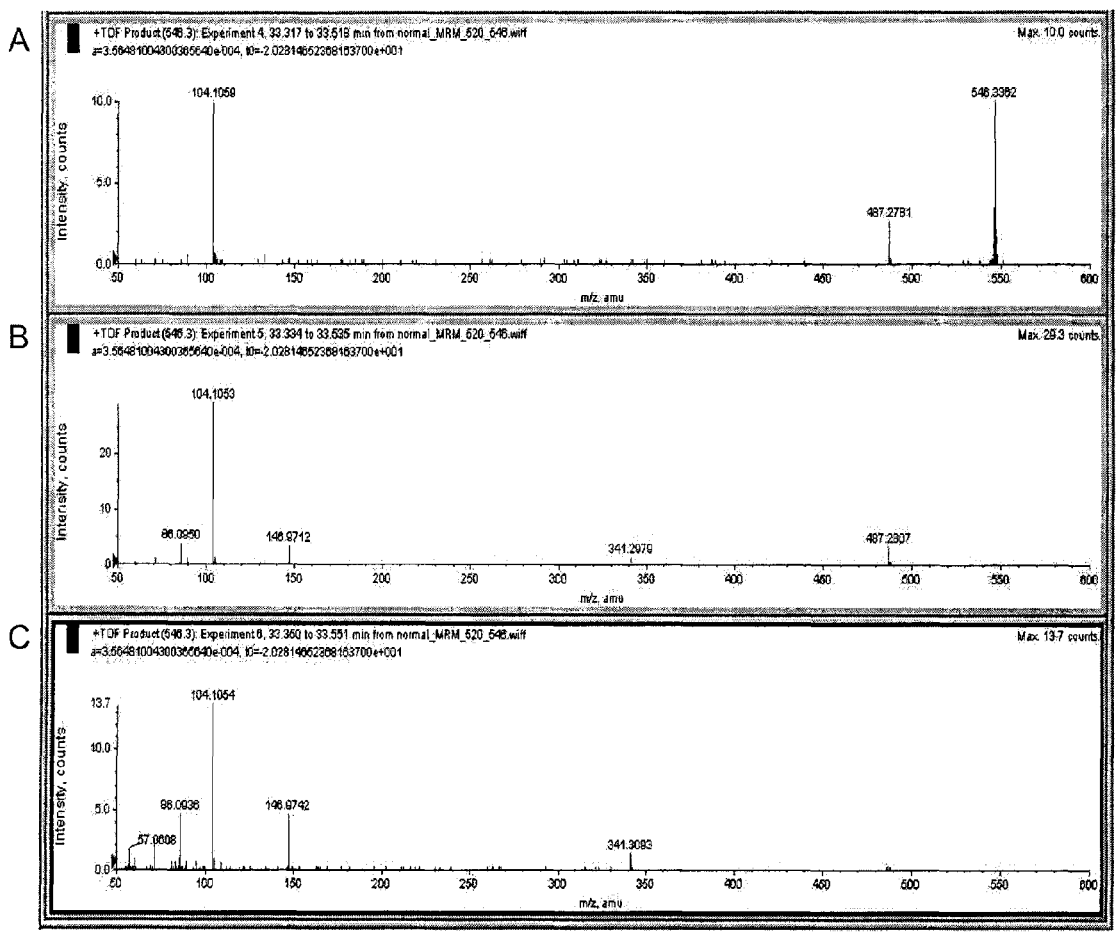
FIG. 13 shows the MS/MS extracted mass spectra for 545.3460 (546.3534 [M+H]), at collision energy voltages of 20 (A), 35 (B) and 50 (C) volts, respectively.
Figure 14:
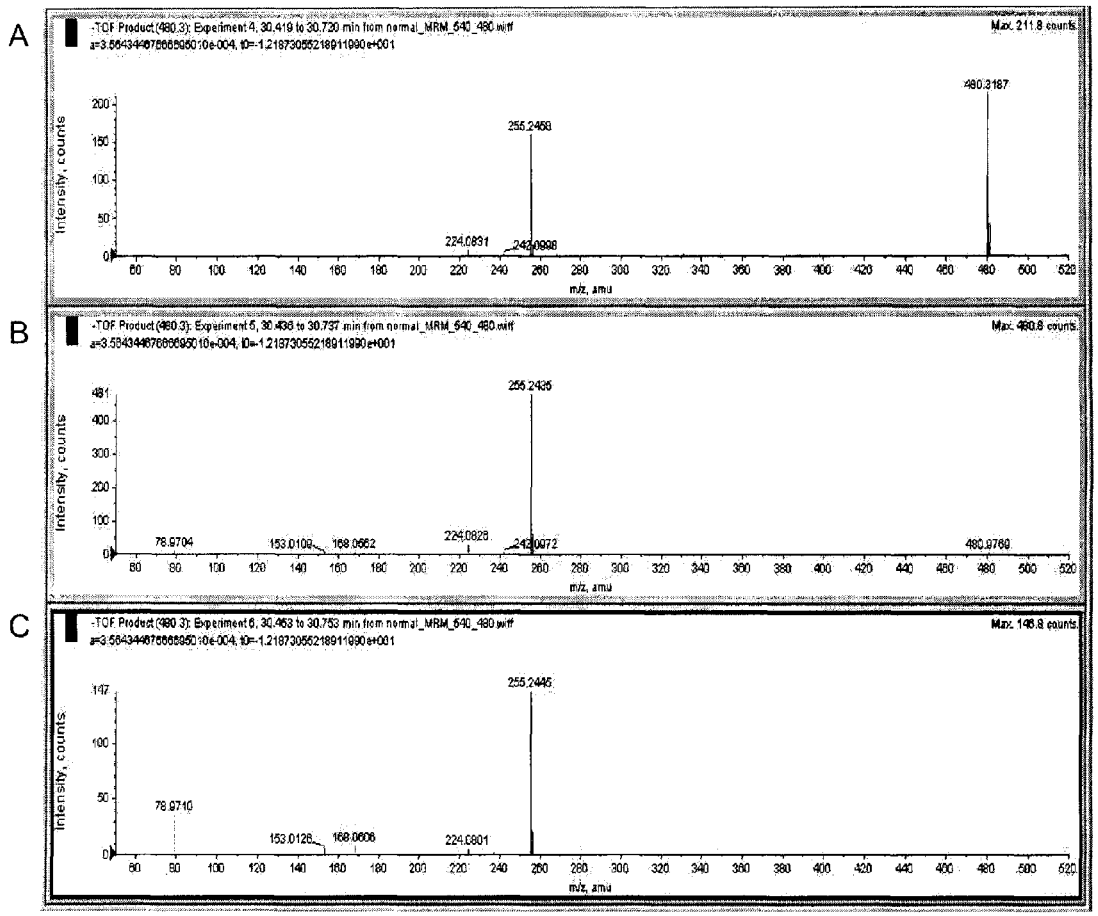
FIG. 14 shows the MS/MS extracted mass spectra for 481.3171 (480.3091 [M−H]), at collision energy voltages of 20 (A), 35 (B) and 50 (C) volts, respectively.
Figure 15:
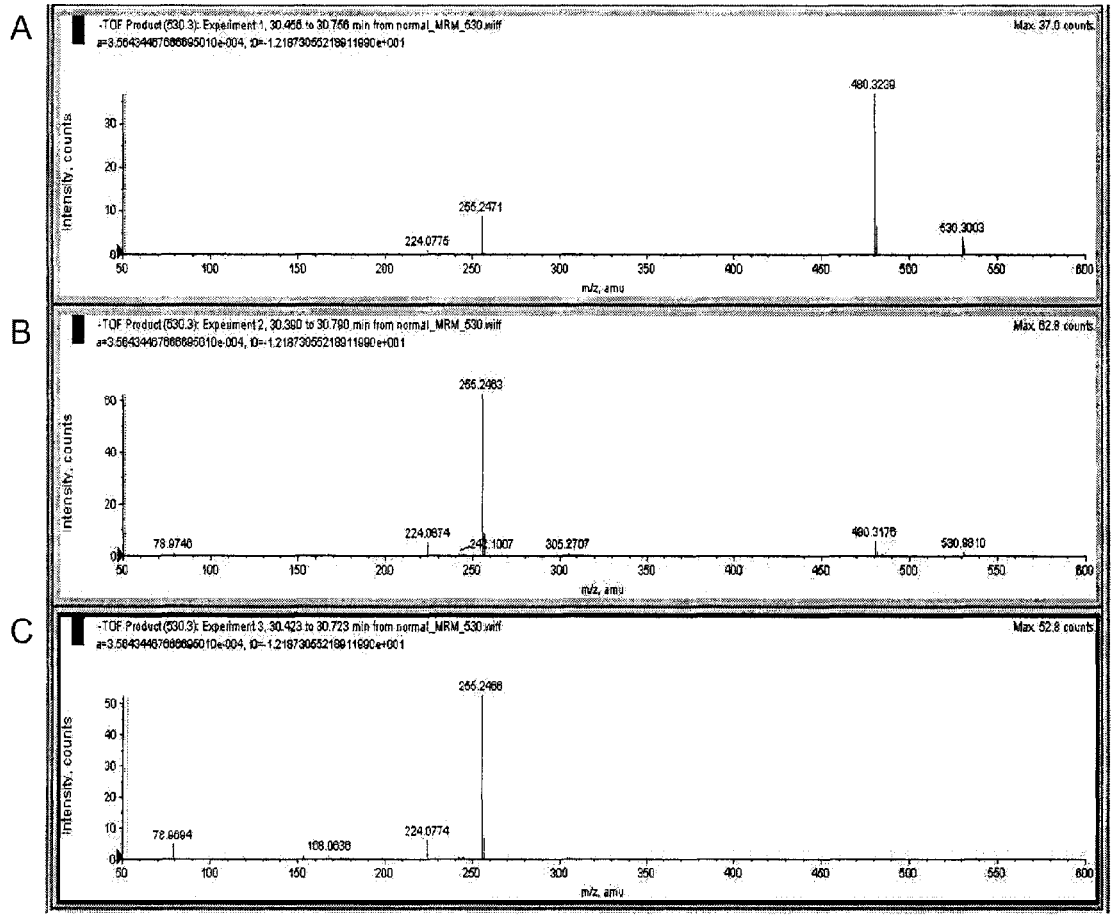
FIG. 15 shows the MS/MS extracted mass spectra for 531.3123 (530.3035 [M−H]), at collision energy voltages of 20 (A), 35 (B) and 50 (C) volts, respectively.
Figure 16:
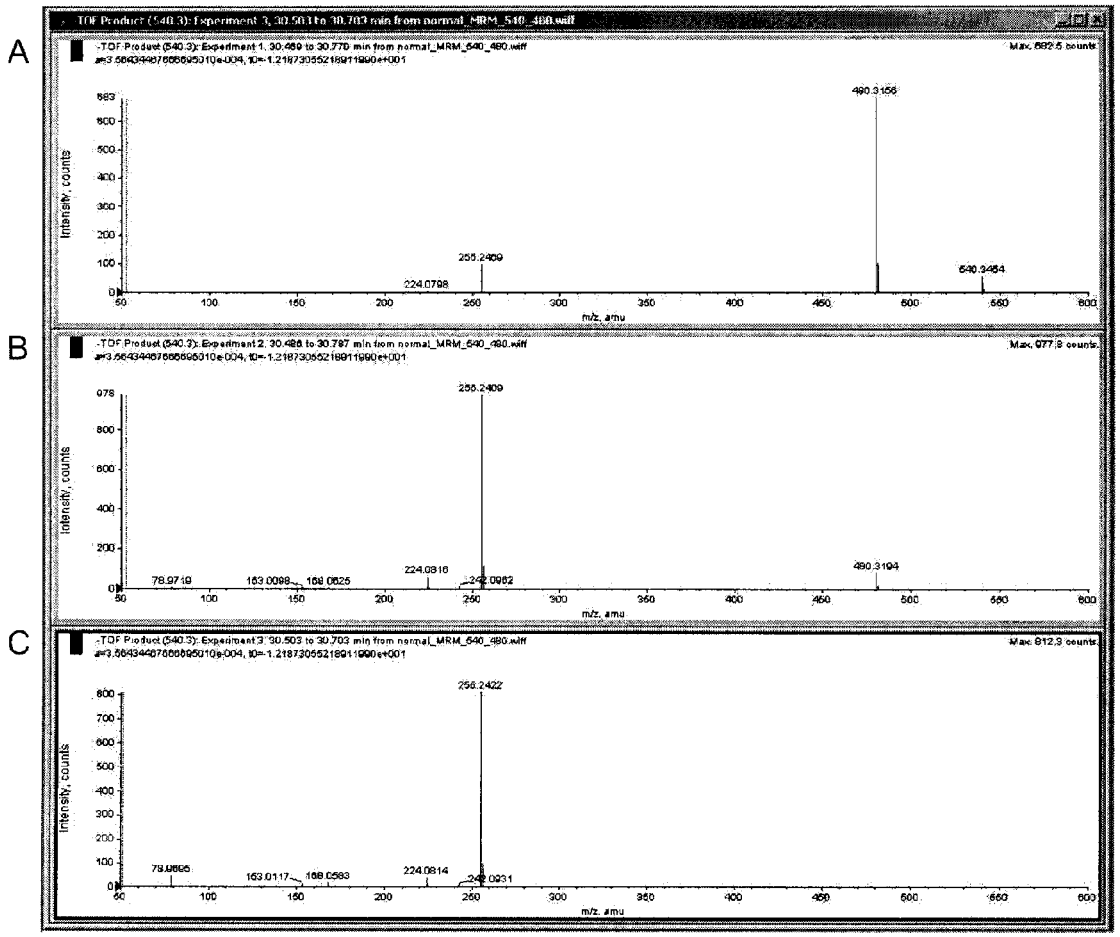
FIG. 16 shows the MS/MS extracted mass spectra for 541.3422 (540.3335 [M−H]), at collision energy voltages of 20 (A), 35 (B) and 50 (C) volts, respectively.
Figure 17:
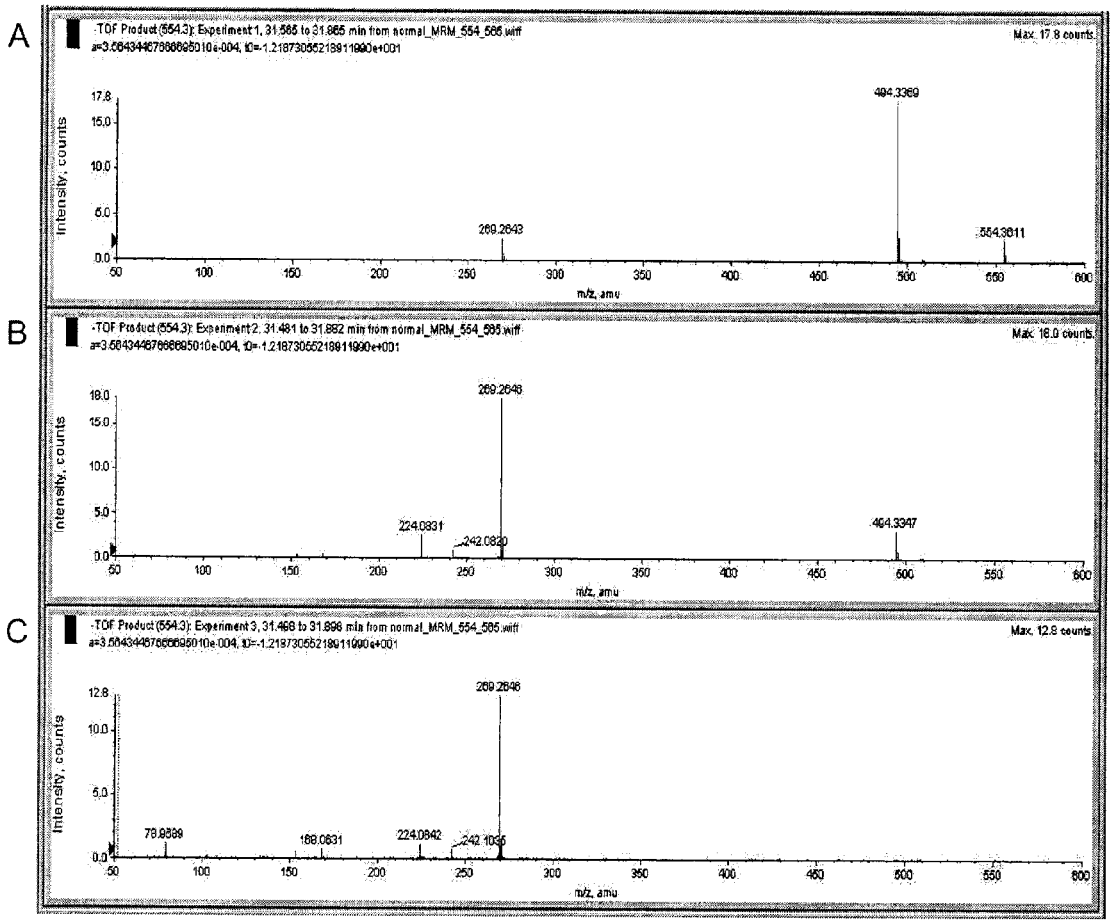
FIG. 17 shows the MS/MS extracted mass spectra for 555.3101 (554.3013 [M−H]), at collision energy voltages of 20 (A), 35 (B) and 50 (C) volts, respectively.
Figure 18:
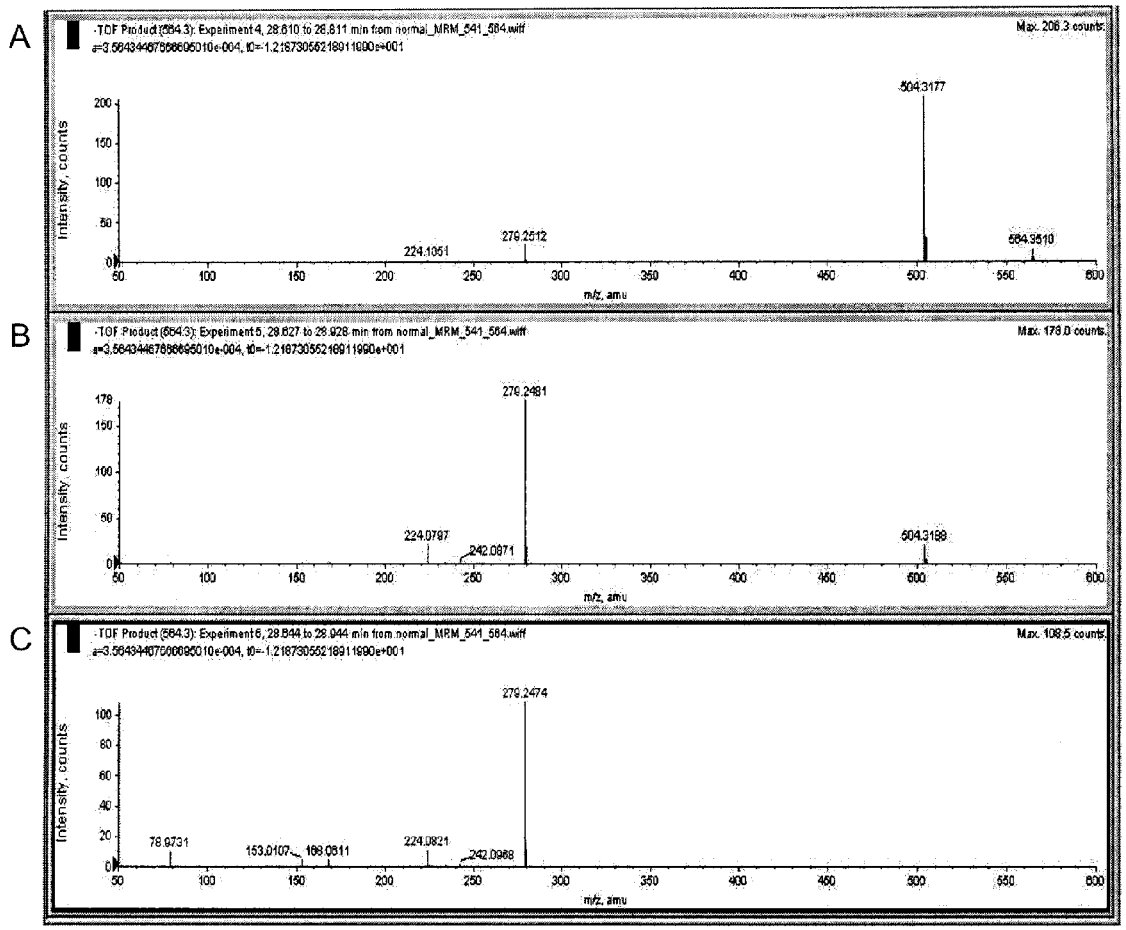
FIG. 18 shows the MS/MS extracted mass spectra for 565.3394 (564.3306 [M−H]), at collision energy voltages of 20 (A), 35 (B) and 50 (C) volts, respectively.
Figure 19:
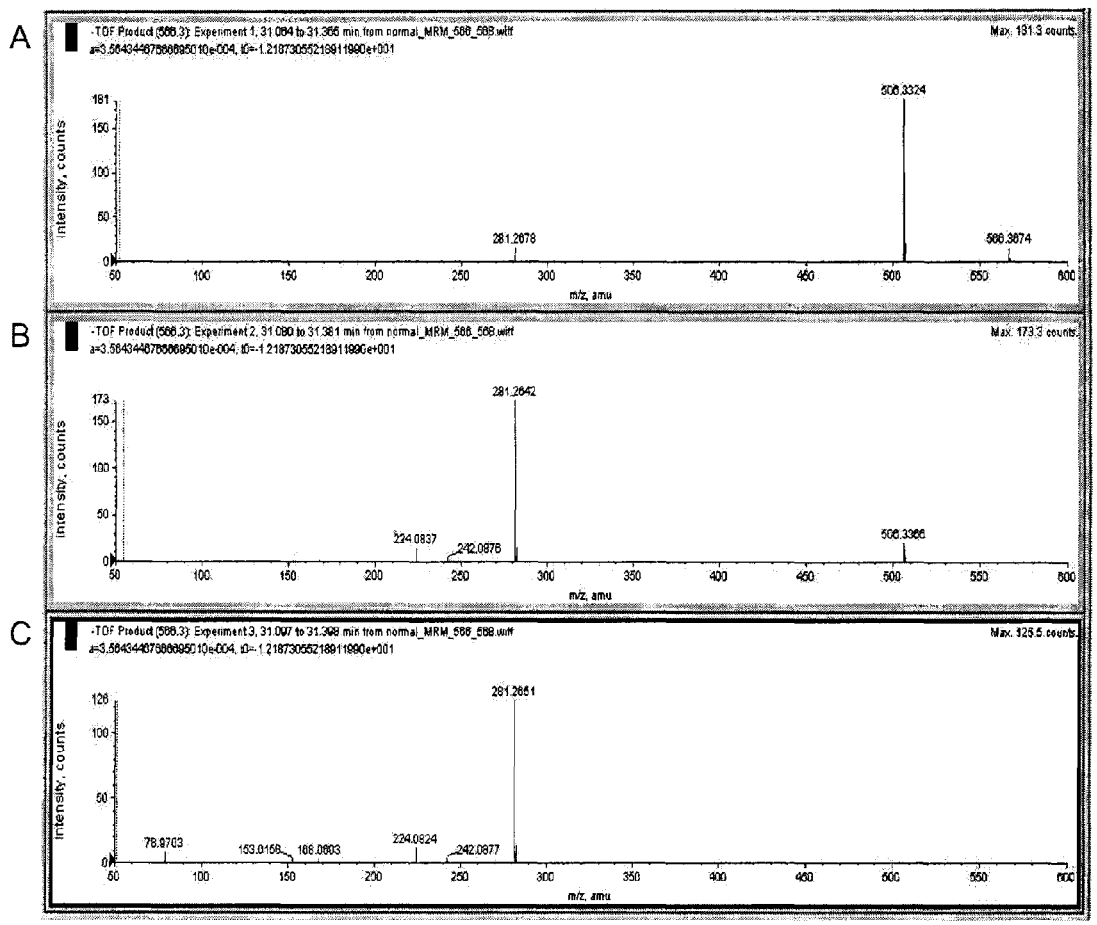
FIG. 19 shows the MS/MS extracted mass spectra for 567.3546 (566.3459 [M−H]), at collision energy voltages of 20 (A), 35 (B) and 50 (C) volts, respectively.
Figure 20:
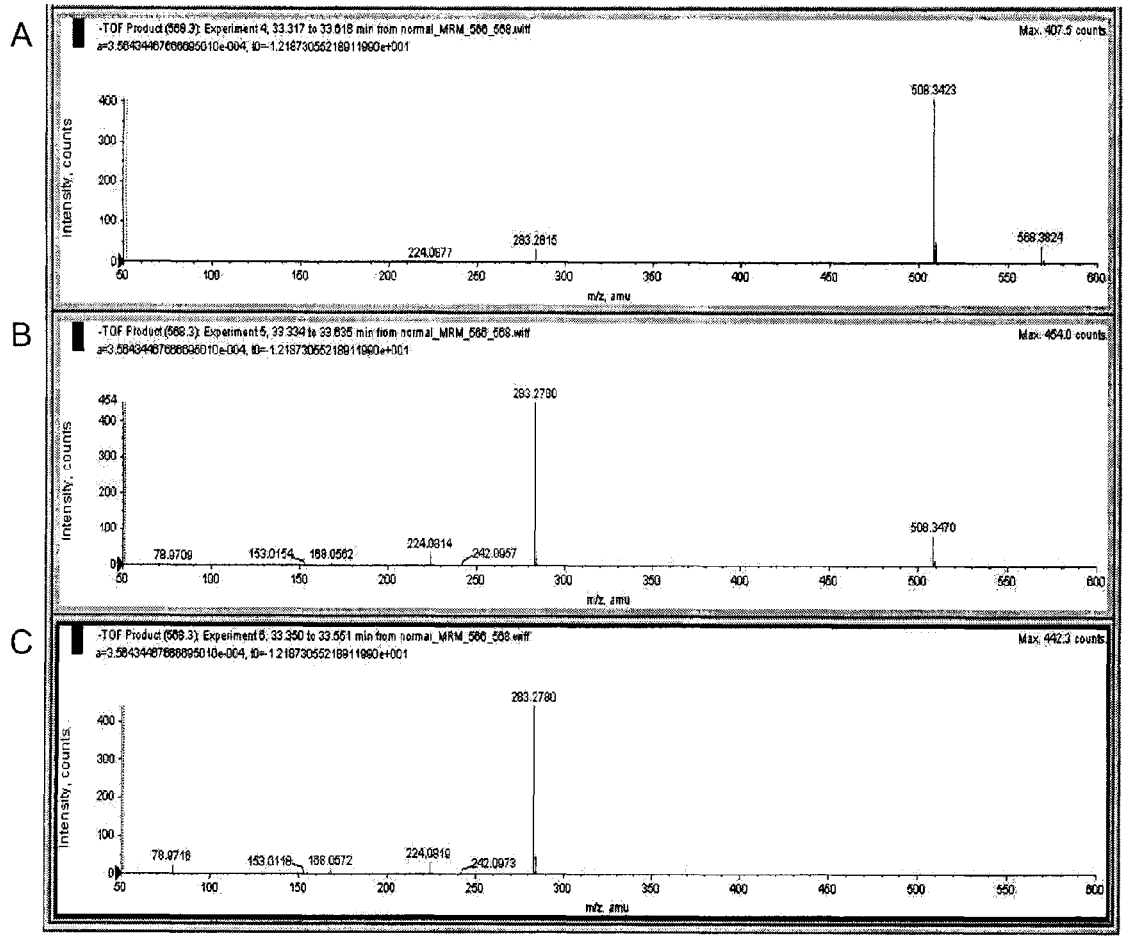
FIG. 20 shows the MS/MS extracted mass spectra for 569.3687 (568.3598 [M−H]), at collision energy voltages of 20 (A), 35 (B) and 50 (C) volts, respectively.

The metabolites within the optimal panel of metabolite markers described above can be further characterized by their MS/MS fragmentation patterns resulting from collision induced dissociation. In particular, metabolite with:

accurate mass 495.3328 has an ionized mass of 496.3401 ([M+H]$^+$, calcd. 496.3398 for $C_{24}H_{51}NO_7P^+$). The MS/MS fragments (MS/MS m/z) (relative intensity) are: 496 ([M+H]$^+$, 90%), 478 (5%), 419 (1%), 313 (1%), 283 (1%), 258 (1%), 239 (1%), 184 (90%), 166 (1%), 104 (100%), 86 (70%); see FIG. 7, Table 3.

accurate mass 517.3148 has an ionized mass of 518.3219 ([M+H]$^+$, calcd. 518.3241 for $C_{26}H_{49}NO_7P^+$). The MS/MS fragments (MS/MS m/z) (relative intensity) are: 518 ([M+H]$^+$, 90%), 459 (10%), 415 (1%), 359 (1%), 341 (1%), 313 (1%), 281 (1%), 221 (1%), 104 (100%), 86 (30%); see FIG. 8, Table 4.

accurate mass 519.3328 has an ionized mass of 520.3401 ([M+H]$^+$, calcd. 520.3398 for $C_{26}H_{51}NO_7P^+$). The MS/MS fragments (MS/MS m/z) (relative intensity) are: 520 ([M+H]$^+$, 10%), 502 (1%), 461 (5%), 281 (1%), 221 (1%), 184 (100%), 166 (5%), 124 (1%), 86 (30%); see FIG. 9, Table 5.

accurate mass 521.3480 has an ionized mass of 522.3554 ([M+H]$^+$, calcd. 522.3554 for $C_{26}H_{53}NO_7P^+$). The MS/MS fragments (MS/MS m/z) (relative intensity) are: 522 ([M+H]$^+$, 100%), 504 (7%), 478 (1%), 357 (1%), 258 (1%), 221 (1%), 184 (60%), 124 (5%), 104 (80%), 86 (30%); see FIG. 10, Table 6.

accurate mass 523.3640 has an ionized mass of 524.3713 ([M+H]$^+$, calcd. 524.3711 for $C_{26}H_{55}NO_7P^+$). The MS/MS fragments (MS/MS m/z) (relative intensity) are: 524 ([M+H]$^+$, 100%), 506 (5%), 496 (1%), 478 (1%), 331 (1%), 313 (1%), 285 (1%), 258 (1%), 184 (70%), 166 (2%), 124 (5%), 104 (70%), 86 (30%); see FIG. 11, Table 7.

accurate mass 541.3148 has an ionized mass of 542.3219 ([M+H]$^+$, calcd. 542.3241 for $C_{28}H_{49}NO_7P^+$). The MS/MS fragments (MS/MS m/z) (relative intensity) are: 542 ([M+H]$^+$, 80%), 483 (25%), 284 (1%), 225 (1%), 184 (1%), 104 (100%), 86 (30%); see FIG. 12, Table 8.

accurate mass 545.3460 has an ionized mass of 546.3534 ([M+H]$^+$, calcd. 546.3554 for $C_{28}H_{35}NO_7P^+$). The MS/MS fragments (MS/MS m/z) (relative intensity) are: 546 ([M+H]$^+$, 90%), 528 (1%), 514 (1%), 487 (30%), 104 (100%), 86 (30%); see FIG. 13, Table 9.

accurate mass 481.3171 has an ionized mass of 480.3091 ([M-H]$^-$, calcd. 480.3081 for $C_{23}H_{47}NO_7P^-$). The MS/MS fragments (MS/MS m/z) (relative intensity) are: 480 ([M-H]$^-$, 100%), 255 (100%), 242 (10%), 224 (15%), 168 (10%), 153 (10%), 79 (25%); see FIG. 14, Table 12.

accurate mass 531.3123 has an ionized mass of 530.3035 ([M-H]$^-$, calcd. 531.3114 for $C_{30}H_{46}NO_5P$). The MS/MS fragments (MS/MS m/z) (relative intensity) are: (530, 100%), 480 (100%), 255 (100%), 242 (10%), 224 (15%), 168 (10%), 153 (10%), 79 (25%); see FIG. 15, Table 13.

accurate mass 541.3422 has an ionized mass of 540.3335 [M-H]$^-$, calcd. 540.3293 for $C_{25}H_{51}NO_9P^-$). The MS/MS fragments (MS/MS m/z) (relative intensity) are: 540 ([M-H]$^-$, 10%), 480 (100%), 255 (100%), 242 (10%), 224 (15%), 168 (10%), 153 (10%), 79 (25%); see FIG. 16, Table 14.

accurate mass 555.3101 has an ionized mass of 554.3013 ([M-H]$^-$, calcd. 555.3172 for $C_{25}H_{50}NO_{10}P$). The MS/MS fragments (MS/MS m/z) (relative intensity) are: 554 ([M-H]$^-$, 10%), 494 (100%), 269 (100%), 242 (10%), 224 (15%), 168 (10%), 153 (10%), 79 (25%); see FIG. 17, Table 15.

accurate mass 565.3394 has an ionized mass of 564.3306 ([M-H]$^-$, calcd. 564.3293 for $C_{27}H_{51}NO_9P^-$). The MS/MS fragments (MS/MS m/z) (relative intensity) are: 564 ([M-H]$^-$, 100%), 504 (100%), 279 (100%), 242 (10%), 224 (15%), 168 (10%), 153 (10%), 79 (25%); see FIG. 18, Table 16.

accurate mass 567.3546 has an ionized mass of 566.3459 ([M-H]$^-$, calcd. 566.3449 for $C_{27}H_{53}NO_9P^-$). The MS/MS fragments (MS/MS m/z) (relative intensity) are: 566 ([M-H]$^-$, 10%), 506 (100%), 281 (100%), 242 (10%), 224 (15%), 168 (10%), 153 (10%), 79 (25%); see FIG. 19, Table 17.

accurate mass 569.3687 has an ionized mass of 568.3598 ([M-H]$^-$, calcd. 568.3605 for $C_{27}H_{55}NO_9P^-$). The MS/MS fragments (MS/MS m/z) (relative intensity) are: 568 (m/z represents the [M+H]$^+$ mass), 10%), 508 (100%), 283 (100%), 242 (10%), 224 (15%), 168 (10%), 153 (10%), 79 (25%); see FIG. 20, Table 18.

Based on the structural characterization of the 14 metabolite markers selected for the diagnosis of prostate cancer, it was determined that the metabolites are molecules related to lysophospholipids. Specifically these include, but are not limited to, lysophosphatidylcholine (lysoPC), lysophosphatidylethanolamine (lysoPE), lysophosphatidyldimethylethanolamine (lysoPdmE), lysophosphatidylserine (lysoPS), lysophosphatidylinositol (lysoPI), and lysophosphatidylglycerol (lysoPG), and platelet activating factors (PAFs), wherein the glycerol backbone is attached to a fatty acid at either SN1 or SN2, for example, 16:0, 18:0, 18:1, 18:2, 18:3, 20:3, 20:4, 20:5, 22:6, ceramide, or other, and a phosphate-containing choline, ethanolamine, dimethylethanolamine, serine, glycerol, or inositol is present at SN3.

Phosphatidylcholine (PC) and phosphatidyethanaolamine (PE) represent the two major lipid components of biological membranes. PC and PE comprise a glycerol backbone containing a phosphate group attached to ethanolamine or choline at the SN3 position, and two fatty acids bound to the SN1 and SN2 positions through an acyl, ether, or vinyl-ether linkages. The fatty acids can be either saturated (more common at SN1), or unsaturated (more common at SN2). When phospholipids such as PC and PE are hydrolyzed by various phospholipases, a lysophospholipid such as lysoPC is generated along with a free fatty acid. Lysophospholipids have been implicated in numerous biological pathways and diseases, such as calcium signaling, atherosclerosis and inflammation (12).

U.S. Published Patent Application US 2004/0137541 (Mills et al.) focuses on the elevation of lysoPCs as key events in or during the progression of cancer. In particular, Mills et al. describe the elevation of lysoPCs in gynecological cancers. This is in contrast with the present invention, which shows that the panel of 14 biomarkers (i.e., metabolites with accurate masses of 519.3328, 541.3148, 545.3460, 555.3101, 541.3422, 565.3394, 521.3480, 517.3148, 567.3546, 523.3640, 531.3123, 481.3171, 495.3328, 569.3687) are decreased in the serum of patients with prostate cancer.

The present invention also provides high-throughput methods for the diagnosis of prostate cancer. The method involves fragmentation of the parent molecule; in a non-limiting example, this may be accomplished by a Q-Trap™ system. Detection of the metabolites may be performed using one of various assay platforms, including calorimetric chemical assays (UV, or other wavelength), antibody-based enzyme-linked immunosorbant assays (ELISAs), chip-based and polymerase-chain reaction for nucleic acid detection assays, bead-based nucleic-acid detection methods, dipstick chemical assays or other chemical reaction, image analysis such as magnetic resonance imaging (MRI), positron emission tomography (PET) scan, computerized tomography (CT) scan, nuclear magnetic resonance (NMR), and various mass spectrometry-based systems.

In a further embodiment of the present invention, there is provided a method for diagnosing prostate cancer or the risk of prostate cancer in a patient. The method comprising the steps of:
- a) obtaining a sample from said patient;
- b) analyzing said sample to obtain quantifying data for one or more than one metabolite marker;
- c) obtaining a ratio for each of the one or more than one metabolite marker to an internal control metabolite;
- d) comparing each ratio of said one or more than one metabolite marker to the internal control metabolite to corresponding data obtained from one or more than one reference sample; and
- e) using said comparison to diagnose prostate cancer or the risk of prostate cancer.

The step of analyzing the sample (step b) may comprise analyzing the sample using a mass spectrometer (MS). For example, and without wishing to be limiting, such mass spectrometer could be of the FTMS, orbitrap, time of flight (TOF) or quadrupole types. Alternatively, the mass spectrometer could be equipped with an additional pre-detector mass filter. For example, and without wishing to be limiting such instruments are commonly referred to as quadrupole-FTMS (Q-FTMS), quadrupole-TOF (Q-TOF) or triple quadrupole (TQ or QQQ). In addition, the mass spectrometer could be operated in either the parent ion detection mode (MS) or in MSn mode, where $n \geq 2$. MSn refers to the situation where the parent ion is fragmented by collision induced dissociation (CID) or other fragmentation procedures to create fragment ions, and then one or more than one of said fragments are detected by the mass spectrometer. Such fragments can then be further fragmented to create further fragments. Alternatively, the sample could be introduced into the mass spectrometer using a liquid or gas chromatographic system or by direct injection.

In the method as just described above, the one or more than one reference sample may be a first baseline reference sample obtained from a control individual.

In the method as described above, the one or more than one metabolite marker may be selected from the metabolites as listed in Table 1, or the metabolites may be the 14 metabolites described above. The "internal control metabolite" refers to an endogenous metabolite naturally present in the patient, provided the metabolite is not associated with the disease and does not vary over disease states; alternatively, the "internal control metabolite" may also refer to an external standard spiked into a serum sample prior to analysis. For example, and without wishing to be limiting, the ratio may be used to determine a diagnostic score for the test subject.

Use of the ratio of the metabolite marker to the internal control metabolite offers measurements that are more stable and reproducible than measurements of absolute levels of the metabolite marker. As the internal control metabolite is present in all samples and does not vary over disease states, the sample-to-sample variability (due to handling, extraction, etc) is minimized.

In the diagnostic methods of the present invention, the measurement of metabolite markers could be taken longitudinally over time in a test subject to determine the change in metabolite concentrations and likelihood of prostate cancer, or risk for the development of prostate cancer. The test subject would provide a sample at a start point, essentially establishing a baseline value; the test subject could then provide samples over time which would be compared to the start point sample. For example, and without wishing to be limiting, an increase in the intensity of the 14 metabolites described above would indicate a reduced risk of prostate cancer, while a decrease in the intensity would indicate an increased risk for prostate cancer.

In yet another embodiment of the present invention, there is provided a method for evaluating the efficacy of a therapy for treating prostate cancer in a patient, comprising:
- a) obtaining a sample from said patient;
- b) analyzing said sample to obtain quantifying data for one or more than one metabolite marker;
- c) comparing said quantifying data to corresponding data obtained from one or more than one reference sample; and
- d) using said comparison to determine whether the therapy is improving the health state of the patient.

Optionally, after the step of analyzing (step b), a ratio for each of the one or more than one metabolite marker to an internal control metabolite may be obtained. In this case, each ratio of said one or more than one metabolite marker to the internal control metabolite to corresponding data obtained from one or more than one reference sample is compared to evaluate the efficacy of the therapy.

The step of analyzing (step b) may comprise analyzing the sample by liquid chromatography mass spectrometry (LC-MS), or alternatively may comprise analyzing the sample by direct injection or liquid chromatography and linear ion trap tandem mass spectrometry when the method is a high-throughput method.

By the term "therapy" or "treatment", it is meant any suitable course of therapy that may attempt to improve the health state of the patient being evaluated. When evaluating the efficacy of the therapy, the effect of the particular therapy in improving or degrading the health state of the patient will be measured. In doing so, a person of skill in the art would be capable of determining whether the therapy is effective for treating prostate cancer. Such treatment may include, but are not limited to, immunotherapy (for example, *Bacillus* Calmette-Guerin injection), radical prostatectomy, chemotherapy, radiation therapy, hormone therapy (including anti-androgens), or others.

In the method as described, the one or more than one reference sample may be any suitable reference sample. For example, and without wishing to be limiting in any manner, the reference sample may be a plurality of samples obtained from control individuals or one or more than one pre-therapy baseline sample obtained from the patient; or any combination thereof. A pre-therapy baseline sample from the patient is particularly useful, as the variation in metabolites will then be specific to the patient.

In the method as described above, the one or more than one metabolite marker may be selected from the metabolites as listed in Table 1, or the metabolites may be the 14 metabolites described above.

The efficacy of a therapy as described above is evaluated based on the measurement of the metabolites and comparison to the reference sample, whereby a restoration of the metabolites towards a normal specified range would be indicative of a positive treatment effect.

In an alternative method of evaluating the efficacy of a therapy for treating prostate cancer, a ratio for each of the one or more than one metabolite marker to an internal control metabolite can be obtained in step b); each ratio of the one or more than one metabolite marker to the internal control metabolite could then be compared to corresponding data obtained from one or more than one reference sample in step c).

The present invention also provides high throughput methods for diagnosis of prostate cancer. The method may involve fragmentation of the parent molecule; in a non-limiting example, this may be accomplished by a Q-Trap™ system. Detection of the metabolites may be performed using one of various assay platforms, including colorimetric chemical assays (UV, or other wavelength), antibody-based enzyme-linked immunosorbant assays (ELISAs), chip-based and polymerase-chain reaction for nucleic acid detection assays, bead-based nucleic-acid detection methods, dipstick chemical assays or other chemical reaction, image analysis such as magnetic resonance imaging (MRI), positron emission tomography (PET) scan, computerized tomography (CT) scan, nuclear magnetic resonance (NMR), and various mass spectrometry-based systems.

The HTS method may involve the measurement of intensity, peak area or summed scans of each selected daughter ion per biomarker, as well as daughter ions for one or more internal standards added to each sample. A ratio may then be generated by dividing each biomarker transition by an internal standard transition. The internal standard provides an indication of the instrument sensitivity, and allows for the normalization of biomarker transition signals across multiple samplings. The ratios generated for the disease-free or healthy population become the defining parameter for the "normal" distribution. A validation set of samples comprising normals and prostate-positives are then analyzed and compared to the normal distribution. This results in essentially two distributions, one for the normal population and one for the prostate-positive population. A cutoff ratio between the two distributions is then selected to determine the sensitivity and specificity of the biomarker assay.

In the methods of the present invention, any individual or combination of metabolites described herein could be combined with existing cancer markers to arrive at a diagnostic/prognostic output. Such existing markers may include, but are not limited to prostate specific antigen (PSA), carcinoembryonic antigen (CEA), cancer antigen (CA) 19-9, C15-3, or CA125.

The above methods may provide medical professionals with a test to better determine the appropriate treatment regimen for a subject based upon the stage at which the cancer is detected. Since the diagnostic methods are relatively non-invasive, a large number of otherwise undiagnosed cases could be identified, particularly early cases, for which specific interventions may be administered by medical professionals. The methods of the present invention may also be used to detect recurrence of cancer, possibly prior to clinical symptoms of the recurrence. Such knowledge could be subsequently used to properly direct treatment regimens that may have improved chances of preventing the recurrence.

The impact of the present invention on the diagnosis of prostate cancer would be tremendous, as literally everyone could be screened longitudinally throughout their lifetime to assess risk. Given that the performance characteristics of the test of the present invention are representative for the general population, this test alone may be superior to any other currently available screening method, as it may have the potential to detect disease progression prior to the emergence of clinical symptoms.

The present invention will be further illustrated in the following examples. An outline of the present invention including each of the examples listed below is shown in FIG. 1.

Example 1

Discovery and Identification of Differentially Expressed Metabolites

Differentially expressed metabolites are identified in clinically diagnosed prostate cancer-positive patients and normal patients.

Clinical Samples. For the prostate cancer screening assay described, serum samples were obtained from representative populations of healthy prostate cancer-free individuals and of professionally diagnosed prostate cancer-positive patients (SeraCare LifeSciences, Inc). The biochemical markers of prostate cancer described below were derived from the analysis of 24 serum samples from prostate cancer-positive patients and 25 serum samples from healthy controls. Samples in both groups were from a diverse population of individuals, ranging in age, ethnicity, weight, occupation, and displaying varying non-prostate cancer-related health-states. All samples were single time-point collections, and the prostate cancer samples were taken either immediately prior to, or immediately following surgical resection of a tumor. All samples were taken prior to chemo or radiation therapy.

The metabolites contained within the 49 serum samples were separated into polar and non-polar extracts by sonication and vigorous mixing (vortex mixing).

The analysis of serum extracts (24 prostate cancer, 25 normal) was made by direct injection into a FTMS and ionization by either electrospray ionization (ESI) or atmospheric pressure chemical ionization (APCI) in both positive and negative modes. Sample extracts were diluted either three or six-fold in methanol:0.1% (v/v) ammonium hydroxide (50:50, v/v) for negative ionization modes, or in methanol:0.1% (v/v) formic acid (50:50, v/v) for positive ionization modes. For APCI, sample extracts were directly injected without diluting. All analyses were performed on a Bruker Daltonics APEX III Fourier transform ion cyclotron resonance mass spectrometer equipped with a 7.0 T actively shielded superconducting magnet (Bruker Daltonics, Billerica, Mass.). Samples were directly injected using ESI and APCI sources at a flow rate of 600 µL per hour. Ion transfer/detection parameters were optimized using a standard mix of serine, tetra-alanine, reserpine, Hewlett-Packard tuning mix and the adrenocorticotrophic hormone fragment 4-10. In addition, the instrument conditions were tuned to optimize ion intensity and broad-band accumulation over the mass range of 100-1000 amu according to the instrument manufacturer's recommendations. A mixture of the abovementioned standards was used to internally calibrate each sample spectrum for mass accuracy over the acquisition range of 100-1000 amu.

In total six separate analyses comprising combinations of extracts and ionization modes were obtained for each sample:
Aqueous Extract
   1. Positive ESI (analysis mode 1101)
   2. Negative ESI (analysis mode 1102)
Organic Extract
   3. Positive ESI (analysis mode 1201)
   4. Negative ESI (analysis mode 1202)
   5. Positive APCI (analysis mode 1203)
   6. Negative APCI (analysis mode 1204)

Mass Spectrometry Data Processing. Using a linear least-squares regression line, mass axis values were calibrated such that each internal standard mass peak had a mass error of <1 p.p.m. compared with its theoretical mass. Using XMASS software from Bruker Daltonics Inc., data file sizes of 1 megaword were acquired and zero-filled to 2 megawords. A sinm data transformation was performed prior to Fourier transform and magnitude calculations. The mass spectra from each analysis were integrated, creating a peak list that contained the accurate mass and absolute intensity of each peak. Compounds in the range of 100-2000 m/z were analyzed. In order to compare and summarize data across different ionization modes and polarities, all detected mass peaks were converted to their corresponding neutral masses assuming hydrogen adduct formation. A self-generated two-dimensional (mass vs. sample intensity) array was then created using DISCOV Ametrics™ software (Phenomenome Discoveries Inc., Saskatoon, SK, Canada). The data from multiple files were integrated and this combined file was then processed to determine all of the unique masses. The average of each unique mass was determined, representing the y axis. This value represents the average of all of the detected accurate masses that were statistically determined to be equivalent. Considering that the mass accuracy of the instrument for the calibration standards is approximately 1 ppm, it would be evident to one skilled in the art that these average masses would include all masses that fall within +/−2 ppm of this average mass, or even +/−5 ppm of this average mass. A column was created for each file that was originally selected to be analyzed, representing the x axis. The intensity for each mass found in each of the files selected was then filled into its representative x,y coordinate. Coordinates that did not contain an intensity value were left blank. Once in the array, the data were further processed, visualized and interpreted, and putative chemical identities were assigned. Each of the spectra were then peak picked to obtain the mass and intensity of all metabolites detected. These data from all of the modes were then merged to create one data file per sample. Then, the data from all 90 samples was merged and aligned to create a two-dimensional metabolite array in which each sample is represented by a column and each unique metabolite is represented by a single row. In the cell corresponding to a given metabolite sample combination, the intensity of the metabolite in that sample was displayed. When the data was represented in this format, metabolites showing differences between groups of samples (i.e., normal and cancer) were determined.

Figure 2:
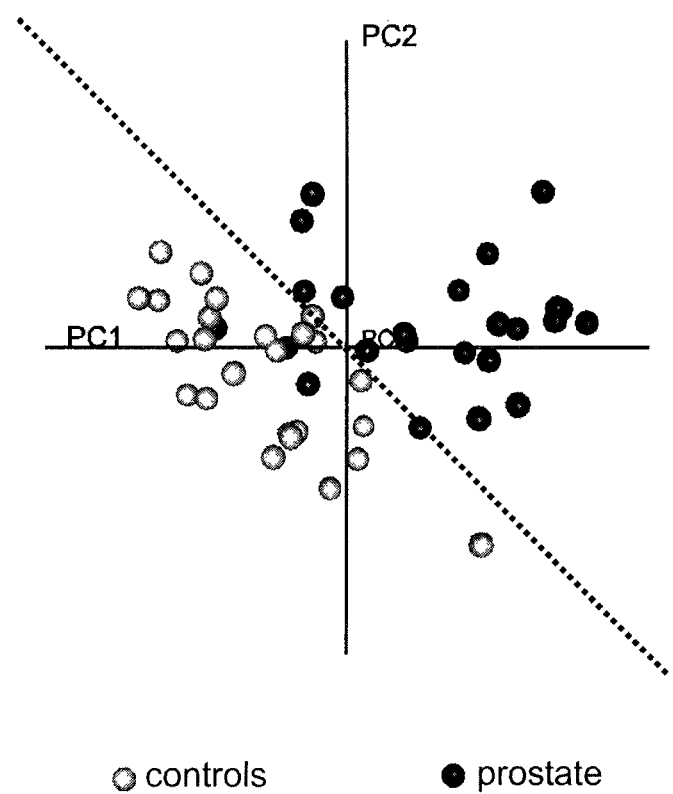
FIG. 2 shows a principle component analysis (PCA) plot generated from the 492 masses with p-values less than 0.05. Each point on the plot represents a single patient sample, while the dotted line represents the boundary between which most of the prostate cancer subjects (in black) and the controls (grey), can be separated.

Advanced Data Interpretation. A student's T-test was used to select for metabolites that differ between the normal and the prostate cancer-positive samples (p<0.05). 492 metabolites met this criterion (as listed in Table 1). Each of these features differs statistically between the two populations and therefore each has potential diagnostic utility. The features are described by their accurate mass and analysis mode, which together are sufficient to provide the putative molecular formulas and chemical characteristics (such as polarity and putative functional groups) of each metabolite. The ability of the 492 metabolites to discriminate between the control and prostate cancer serum is shown by the PCA plot in FIG. 2. A relatively clear distinction (as shown by the dotted line) between the controls (in grey) and prostate cancers (in black) can be drawn, which indicates that the 492 metabolites together can diagnose a prostate cancer-positive serum sample relative to control serum.

However, the incorporation and development of 492 signals into a commercially useful assay is not practical, therefore a combination of univariate analyses and chemical information was used to further select a subset of 14 metabolites from the 492 for additional characterization. The subset of 14 metabolites selected were detected in two different modes: those with accurate masses (measured in Daltons) of 495.3328, 517.3148, 519.3328, 521.3480, 523.3640, 541.3148, and 545.3460, where a +/−5 ppm difference would indicate the same metabolite, were detected as positive ions using methods described in this application and metabolites with accurate masses (measured in Daltons) of 481.3171, 531.3123, 541.3422, 555.3101, 565.3394, 567.3546, and 569.3687 were detected as negative ions using the methods described within this application. All metabolite masses represent $^{12}C$ molecules.

Figure 3:
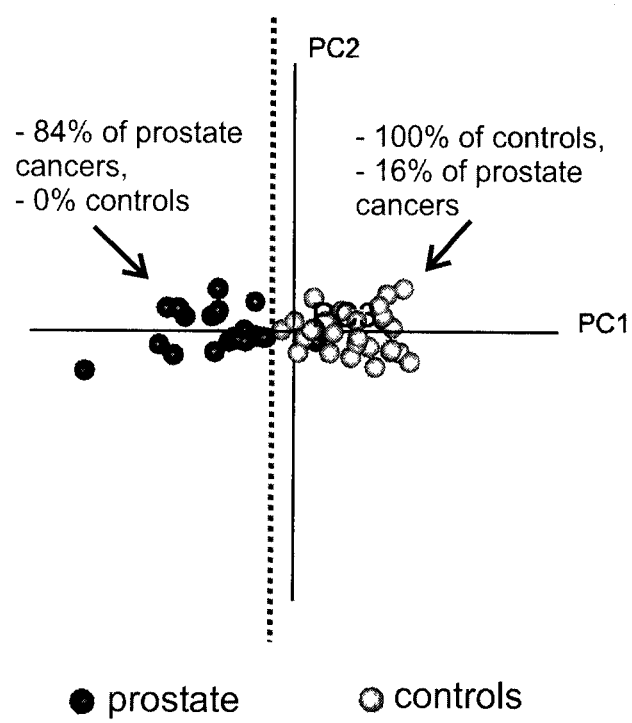
FIG. 3 shows a PCA plot generated from a subset of 14 masses selected from the 492 with p-values <0.05. A high degree of discrimination between the prostate cancer subjects (black points) and the control subjects (grey points) is evident using only the 14 masses. The dotted line shows the boundary between the two cohorts, which when used as a cutoff value results in 84% sensitivity (84% of cancers detected) and 100% specificity (no controls being classified as cancer, or false positives).
Figure 4:
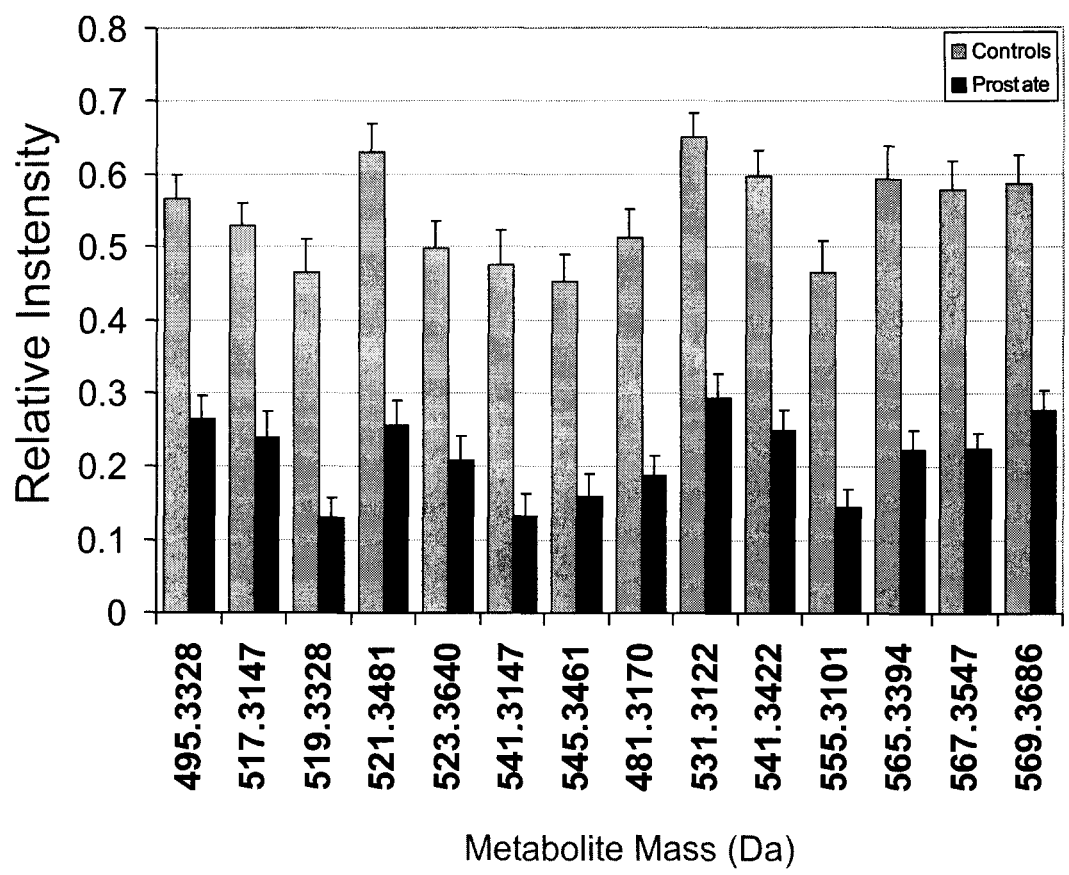
FIG. 4 shows a bar graph of the average relative intensities of the 14 selected masses in the control (grey) and the prostate cancer subjects (black). Error bars=±1 s.d.

The diagnostic accuracy of the 14 masses is shown through a PCA plot in FIG. 3, which illustrates a clear separation between disease and controls. In fact, separating the controls from the prostate cancers using the dotted line results in a sensitivity of 84% and specificity of 100%. A graph of the relative intensities of the 14 masses as detected on the FTICR is shown in FIG. 4 (using data scaled between 0 and 1 for each mass). Each of the markers appears to show a reduction or deficiency of approximately 50% (on average) in the prostate cancer sera versus control sera.

Based upon these results, a clear distinction can be made between the serum of prostate cancer-positive patients and healthy (prostate cancer negative) individuals. Therefore, these markers, which are capable of identifying and distinguishing prostate cancer-positive and prostate cancer-negative serum, can form the basis for a prostate cancer diagnostic test as presently described.

Example 2

Independent Method Confirmation of Discovered Metabolites

Figure 5:
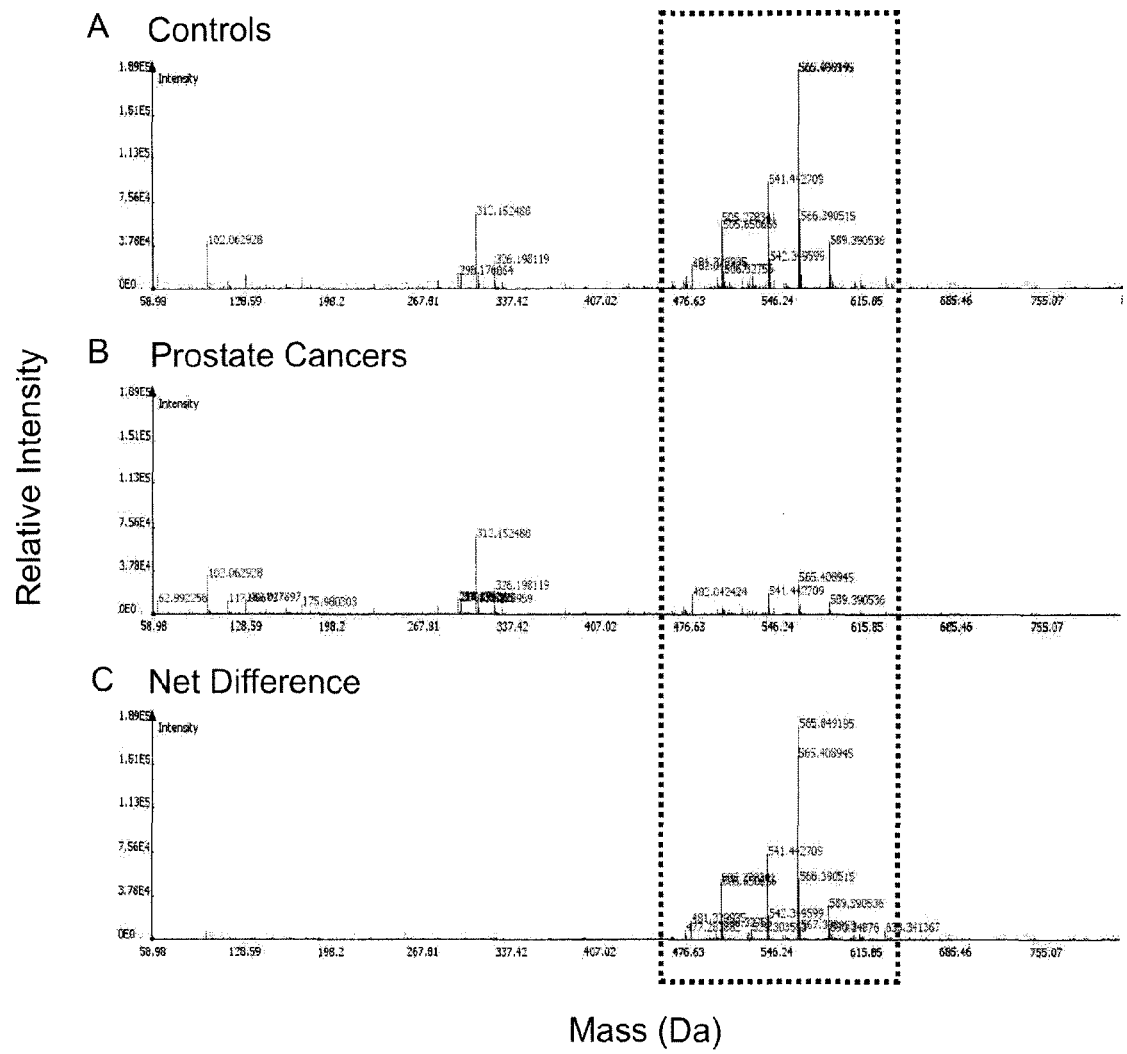
FIG. 5 shows a series of extracted mass spectra for metabolites eluting between 16 and 18 minutes of chromatographic separation on HPLC, as detected using time-of-flight (TOF) MS. The box indicates a region of metabolite masses detected between approximately 450 and 600 daltons in control serum (A), but absent from prostate cancer-positive serum (B). The lower panel (C) indicates the net difference between the control and prostate cancer spectra.
Figure 6:
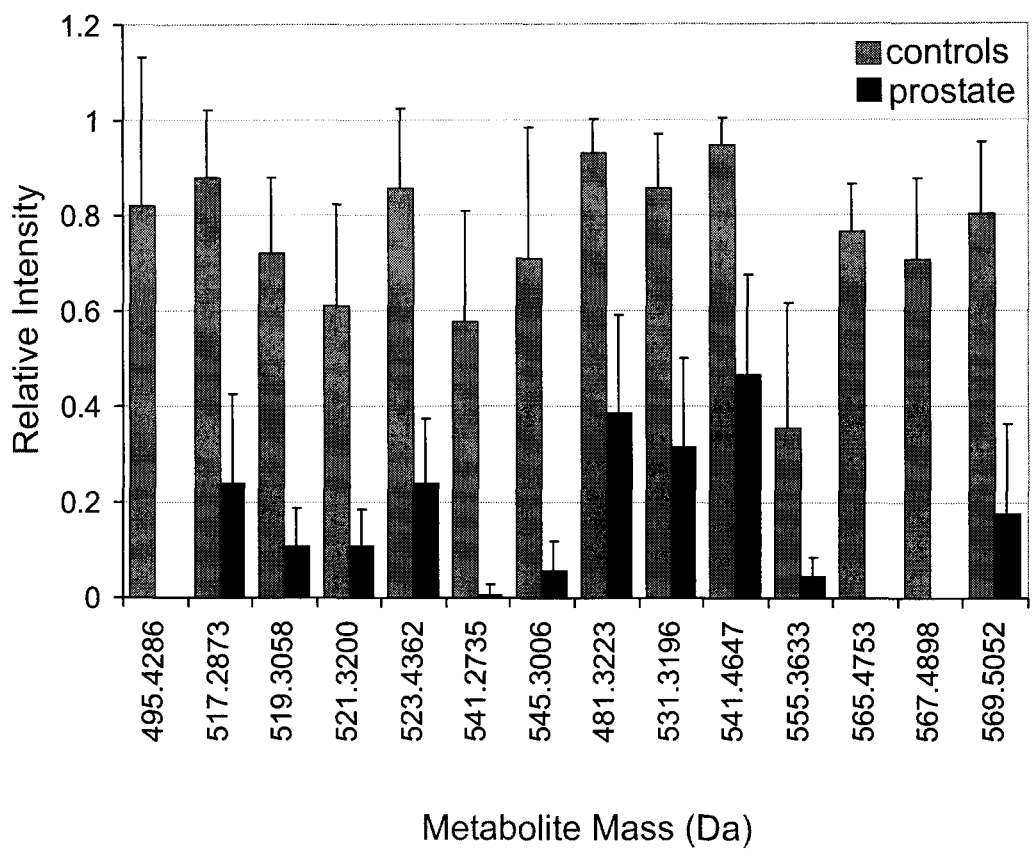
FIG. 6 shows a graph of the 14 said metabolites as detected using TOF-MS following HPLC. Error bars=1 s.d.

The metabolites and their associations with the clinical variables described in Example 1 were further confirmed using an independent mass spectrometry system. Representative aqueous sample extracts from each variable group (10 controls and 9 prostate cancers) were re-analyzed by LC-MS using an HP 1050 high-performance liquid chromatography, or equivalent interfaced to an ABI Q-Star, or equivalent mass spectrometer to obtain mass and intensity information for the purpose of identifying metabolites that differ in intensity between the clinical variables under investigation. Data were acquired using full-scan detection in both positive and negative ESI modes, and the resulting spectral data calibrated and aligned using Phenomenome Profiler software. We identified a retention time window (time at which molecular species are eluting off of the HPLC column), of approximately 28 to 34 minutes under the specified chromatographic conditions. FIG. 5 shows the extracted mass spectra within this retention time range for the controls (A), prostate cancers (B), and the net difference between the controls and prostate cancers (C). The boxed region shows the mass range where the subset of 14 masses previously described was redetected. As previously observed, these molecules were significantly lower in intensity in the prostate cancer sera compared to the controls. A bar graph of the average raw intensities (scaled between 0 and 1) for each of the 14 metabolites as detected using HPLC-coupled TOF-MS, is shown in FIG. 6.

Example 3

MS/MS Characterization of the 14 Metabolite Subset

Various characteristics can be used for structure elucidation of metabolites include accurate mass and molecular formula determination, polarity, acid/base properties, NMR spectra, and MS/MS or MSn spectra. These data can be used as fingerprints of a particular metabolite and are unique identifiers of a particular metabolite regardless of whether the complete structure has been determined. The data include:

1. LC retention time. The extracts containing the metabolites of interest are subjected to reverse phase LC-MS using a C18 column and analysis by MS to determine their retention time under standardized conditions. When the extracts were subjected to LC/MS analysis, all 14 metabolites co-eluted within 26-34 min range.

2. MS/MS spectra. The 14 metabolites of interest were further characterized by performing MS/MS fragmentation using collision induced dissociation (CID). This MS/MS analysis was performed in real time (i.e. during the chromatographic elution process) or off-line on fractions collected from the chromatographic separation process.

Aqueous fractions from 9 prostate cancer and 10 normal sample extracts were evaporated to dryness under nitrogen gas and reconstituted in 100 µL of water:methanol:formic acid (97.9:2:0.1). 5 µL of the reconstituted sample was used for HPLC (Agilent 1100 system with MetaSil AQ 3 um, C18, 100×2.0 mm column, Varian Inc.) for full scan and MS/MS. The mobile phase consisted of water:methanol:formic acid (97.9:2:0.1) as solvent A, and 0.1% formic acid in methanol as solvent B. At a flow rate of 0.2 ml/min, the solvent gradient was as follows: Solvent A was held at 100% for the first minute, then changed to 20% A and 80% B using a linear gradient over 10 min, and then held at 20% A, 80% B for 9 min; then the solvent mixture was changed to 100% B during the next 10 min using a linear gradient, and was held at 100% B for 15 minutes. Finally, the solvent mixture was held at 100% A to equilibrate the column for duration of 20 min (total elapsed time 65 min). Eluate from the HPLC was analyzed using an ABI QSTART XL mass spectrometer fitted with an ESI (TurbolonSpray™) source in positive and negative mode.

For time-of-flight full scan mode, the "TOF-MS" scan type was used with an accumulation time of 1.0 sec, a mass scan range of 50 to 1500 Da, and duration time of 60 min. The source parameters at positive ESI mode were as follows: Ion source gas 1 (GS1) 55; Ion source gas 2 (GS2) 90; Curtain gas (CUR) 40; Nebulizer Current (NC) 3.0; Temperature 400° C.; Declustering Potential (DP) 60; Focusing Potential (FP) 265; Declustering Potential 2 (DP2) 15. The source parameters at negative ESI mode were as follows: Ion source gas 1 (GS1) 55; Ion source gas 2 (GS2) 70; Curtain gas (CUR) 40; Nebulizer Current (NC) 0; Temperature 400° C.; Declustering Potential (DP) −55; Focusing Potential (FP) −265; Declustering Potential 2 (DP2) −15.

In MS/MS mode, the "Product Ion" scan type was used with an accumulation time of 1.0 sec, a scan range of 50 to 650 Da, and a duration time of 60 min. All source parameters are the same as above, with collision energy (CE) settings of 20V, 35V, 50V at positive mode and −20V, −35V, −50V at negative mode. The collision gas (CAD, nitrogen) was set at 5.

The structure of a given molecule dictates a specific fragmentation pattern under defined conditions and is unique for that molecule (equivalent to a person's fingerprint)—even slight changes to the molecule's structure can result in a different fragmentation pattern. In addition to providing a fingerprint of the molecule's identity, the fragments generated by CID were used to gain insights regarding the structure of the metabolites.

Upon constructing possible molecular formulae for the positive mode biomarker panel (i.e., metabolites with accurate masses of 495.3328, 517.3148, 519.3328, 521.3480, 523.3640, 541.3148, and 545.3460), all seven biomarkers were found to possess similar formulae of $RNO_7P$, where R is the variable fatty acid type, indicating that they could be phospholipid choline-related compounds. A summary of the proposed structures based upon MS/MS interprestations is shown in Table 2. The fragmentation spectra for the 7 metabolites detected in the positive ionization mode are shown in FIGS. 7 to 13 (collision energies of 20 (A), 35 (B) and 50 (C) volts), and the masses of the fragments and molecular formula assignments listed in Tables 3 through 9. Each table lists the daughter ions resulting from the CID, as well as the proposed structures of the fragment ions and the fragment losses.

The MS/MS data obtained in the positive mode ESI indicates that each of the seven metabolites abstracted a proton, resulting in the corresponding molecular ion ($[M+H]^+$) in their MS/MS spectra. This suggests the protonation of the phosphate group leaving the positively charged quaternary ammonium ion as the parent ion. Evidence for losing the quaternary amine group, $(CH_3)_3NH^+$, $[M+H−60]^+$) was observed for all of the metabolites confirming the presence of the choline head group in these metabolites. Fragment ions due to phosphocholine ($C_5H_{15}NO_4P^+$, m/z 184) and ethanol-quaternary amine ($C_5H_{14}NO^+$, m/z 104) were other indications suggesting phosphocholine-type structures. Loss of $H_2O$ from the molecular ions was also observed confirming the presence of free hydroxy groups at sn-2 positions inherent in lysolipid-type structures.

Fragment ions, though weak, were observed for either a sn-1 fatty acid side chain or loss thereof. For example, for metabolite 495.3328, where palmitic acid was thought to be the sn-1 fatty acid, the fragment ion representing m/z 458 was assigned as plausibly due to the loss of $C_{16}H_{32}O$ unit. Another fragment ion at m/z 239 ($C_{16}H_{31}O^+$) though low in intensity was also present signifying the sn-1 fatty acid itself. Based on these deductions, the structure was proposed as 2-hydroxy-1-palmitoyl-sn-glycero-3-phosphocholine. The structure of 495.3328 was confirmed to be 2-hydroxy-1-palmitoyl-sn-glycero-3-phosphocholine (commercial standard) by comparison of their LC/MS and MS/MS spectral data (fragment ion comparisons shown in Table 10).

The MS/MS spectral data of the remaining 6 metabolites were very similar to that of 495.3328, the only differences being differences in the sn-1 fatty acid side chains. For metabolites 519.3328 (520 M−H), 521.3481 (522 M−H), and 523.3640 (524 M−H), loss of $H_2O$ from their parent ions resulted in fragment ions m/z 518, 520 and 522 respectively suggesting that their fatty acid side chains varied with an increasing degree of unsaturation. For 520, the sn-1 side chain was deduced as linoleic acid due to the fragment ion at m/z 281. In 522 and 524, a common fragment ion at m/z 258, was thought to be due to the loss of oleyl ($C_{18}H_{33}O$) and stearyl ($C_{18}H_{35}O$) substituents from their parent ions thus confirming oleic and stearic acid side chains respectively. For metabolite 541.3148 (542 M−H), the fragment ion at m/z 225 was deduced as loss of eicosapentaenoic side chain. Using the above discussed MS/MS data, the structures of these 7 prostate cancer biomarkers proposed as shown in Table 2.

The fragmentation spectra of the seven metabolites detected in the negative ionization mode (i.e., metabolites with accurate masses of 481.3171, 531.3123, 541.3422, 555.3101, 565.3394, 567.3546, and 569.3687), are shown in FIGS. 14 to 20 (collision energies of 20, 35 and 50 volts). The molecular formulae suggested that four (541.3422, 565.3394, 567.3546, 569.3687) out of the seven biomarkers were found to possess similar formulae of $RNO_9P$, where R is the variable fatty acid type, indicating that they could be phospholipid ethanolamine related compounds. Table 11 summarizes the molecular formulae and putative structures of the molecules based upon the MS/MS data. Tables 12 to 18 list the fragment ion masses, putative formulas of the fragments and fragment losses as well as putative structures for each fragment.

In the negative mode with electro spray ionization, (ESI), each of the seven molecules loose a proton resulting in the corresponding molecular ion ($[M−H+]^−$) in their MS/MS spectra. This suggests the de-protonation of the phosphate group, leaving the negatively charged phosphate ion as the parent ion. Fragment ions were observed for sn-1 fatty acid side chain for the markers 481.3168 and 541.3422 (palmityl, $C_{16}H_{31}O_2$, m/z 255), 565.3394 (linoleyl, $C_{18}H_{31}O_2$, m/z 279), 567.3546 (oleyl, $C_{18}H_{33}O_2$, m/z 281), and 569.3687 (stearyl, $C_{18}H_{35}O_2$, m/z 283) as prominent signals in their MS/MS spectra. Upon comparing the MS/MS spectra of 569.3687 to its corresponding lysophospholipid ethanolamine counterpart, 2-hydroxy-1-stearyl-sn-glycero-3-phosphoethanolamine ($C_{23}H_{48}NO_7P$, exact mass: 481.317) (commercial standard), a number of similarities were observed (Table 19). The initial fragment loss from the parent ion $[M+H]^-$ of 569.3687 was corresponding to a mass loss of 60 Dalton unit which is associated with the formula $C_2H_4O_2$. This fragment loss was consistent to all the markers of the above panel with exception to 481.3171 which has a formula of $C_{23}H_{48}NO_7P$ similar to the general formulation of the sn2-hydroxyphosphoethanolamine types. In comparing the fragment m/z 508 of 569.3687 to the parent ion of its lysophosphoetanolamine commercial standard (m/z 480), a difference of only 28 Dalton units was observed, which lead to the derivation of N,N-dimethyl phosphoethanolamine type of structures for the biomarker panel. The fragment losses after the loss of sn2 fatty acid, m/z 242, 168, 153 and 79 are constantly observed for all seven biomarkers further confirming a plausible dimethyl ethanolamine type of backbone on the molecule.

While the reported MS/MS data is consistent with molecules of lysophospholipid species, the present invention also includes structures where functional groups or reported fragments are connected in ways that are not presently indicated.

Example 4

High Throughput Commercial Method Development

A high throughput screening (HTS) method was developed for diagnosing prostate cancer. The method described below is compatible with current laboratory instrumentation and triple-quadrupole mass spectrometers that are in place in many laboratories globally (13, 14).

High throughput screening (HTS) was performed with a linear ion trap mass spectrometer (Q-trap 4000, Applied Biosystem) coupled with Agilent 1100 LC system. Serum samples were extracted as described in Example 1. The aqueous fraction was mixed 1:3 with acetonitrile to precipitate proteins prior to use for the analysis of each sample. 15 µL of internal standard (reserpine in methanol: 100 µg/mL for negative ESI; 1 µg/mL for positive ESI) and 108 µL of 3:1 (acetonitrile):(1% formic acid in ddH2O) was added to each 12 µL sample aliquot for a total volume of 135 µL. The autosampler injected 100 µL of the sample by flow-injection analysis (FIA) into an ABI 4000QTRAP. The carrier solvent was 60:40 (methanol):(1% formic acid in ddH2O), with a flow rate of 450 µL/min into the APCI source.

The MS/MS HTS methods (negative and positive ESI) were developed on a quadrupole linear ion trap ABI 4000QTRAP mass spectrometer equipped with a TurboV™ source with an Ionspray probe. The source gas parameters were as follows:

Negative ESI: (CUR: 10.0, CAD: 6, IS: −4500, TEM: 500, GS1: 50, GS2: 60, interface heater on. "Compound" settings were as follows: entrance potential (EP): −10, and collision cell exit potential (CXP): −10.0); Positive ESI: (CUR: 10.0, CAD: 6, IS: 5500, TEM: 500, GS1: 30, GS2: 60, interface heater on. "Compound" settings were as follows: entrance potential (EP): 10, and collision cell exit potential (CXP): 15.0).

The methods were based on the multiple reaction monitoring (MRM) of 2 MRM transitions for each biomarker, and 2 MRM transitions for the internal standard (reserpine, though other compounds may be used) for a total of 16 MRM's for each method. Each of the transitions was monitored for 100 msec or 70 msec for positive and negative ESI modes, respectively. The total acquisition time per sample was approximately 1 min. Briefly, each method measured the intensities of each of 14 biomarker MRM transitions (from 7 parents) and 2 internal standard (IS) MRM transitions (from 1 parent) as shown in Table 20. A patient score was then generated by determining the lowest mean-normalized log(2) transformed ratio of the seven measured biomarker:IS transitions per patient. This value was then compared to a distribution of scores generated from normal individuals, and a prostate cancer risk factor was assigned accordingly. It was confirmed that the ABI 400QTRAP was capable of accurately measuring the MRM transition peak areas using the method described above by plotting the peak area ratios of the biomarker transitions versus the internal standard transitions for each of the seven biomarkers for each method. In addition, the HTS method also incorporates a series of dilutions of extracted human reference serum material, which allowed for the determination and assurance of instrument linearity. If the calibration curve has a $R^2$ value <0.98, then the sample run is considered a failure and the sample needs to be rerun.

As described above, the prostate cancer HTS triple-quad method comprises two independent data acquisition components due to the fact that half the molecules are detected in negative mode, and the other half in positive mode.

Figure 21:
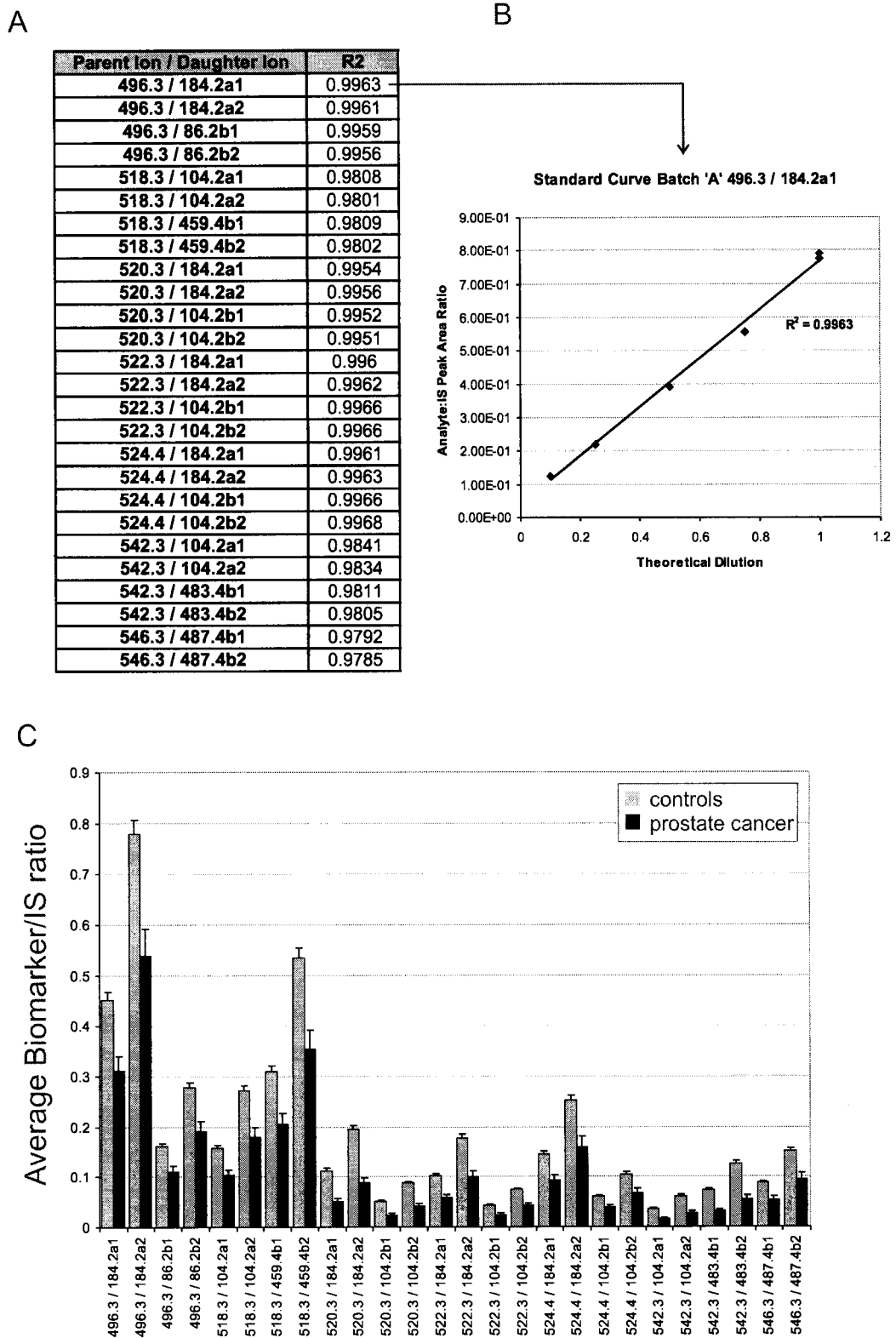
FIG. 21 shows A), the list of the parent-daughter ion transitions used for the positive ESI triple-quadrupole HTS method as well as the R-squared correlation coefficient resulting from calculation of linearity across five diluted samples. B), Standard curve for transition 496.3/184.2a1. C). The average ratio (biomarker:IS peak area) for each transition in the prostate (black) and control (grey) subjects.

For the seven lysophosphaditylcholine molecules detected in the positive mode (i.e., metabolites with accurate masses of 495.3328, 517.3148, 519.3328, 521.3480, 523.3640, 541.3148, and 545.3460), the transitions used for measurement are shown in FIG. 21A, and comprise two daughter ion transitions per molecule for each of the biomarkers (a and b, with the exception of 546.3, in which a single transition was used), and two internal standard transitions per sample (1 and 2). Dividing each biomarker transition by each internal standard transition therefore resulted in 26 ratios per biomarker. A normal reference serum sample is also analyzed at varying dilutions to assess instrument linearity, for which R-squared coefficients can be calculated. The average R-squared values for data obtained below for each transition ratio is shown in FIG. 21A. A sample plot of the average intensities of the dilutions for 496.3/184.2a1 is shown in FIG. 21B. The ratio data was then normalized to the mean of the control population and log(2) transformed. The lowest ratio value of per patient was then selected as the final output score. The distributions of these patient scores were then visualized to determine the optimum diagnostic cut-off point.

The same 24 prostate cancer serum samples used for the discovery phase were re-analyzed using this method, along with an expanded independent set of 147 male control samples. The average ratio (not log transformed) for each of the 26 transitions in the control and prostate cancer cohorts is shown in FIG. 21C. As expected, the intensity of each ratio is lower in the prostate cancer cohort compared to the controls.

Figure 22:
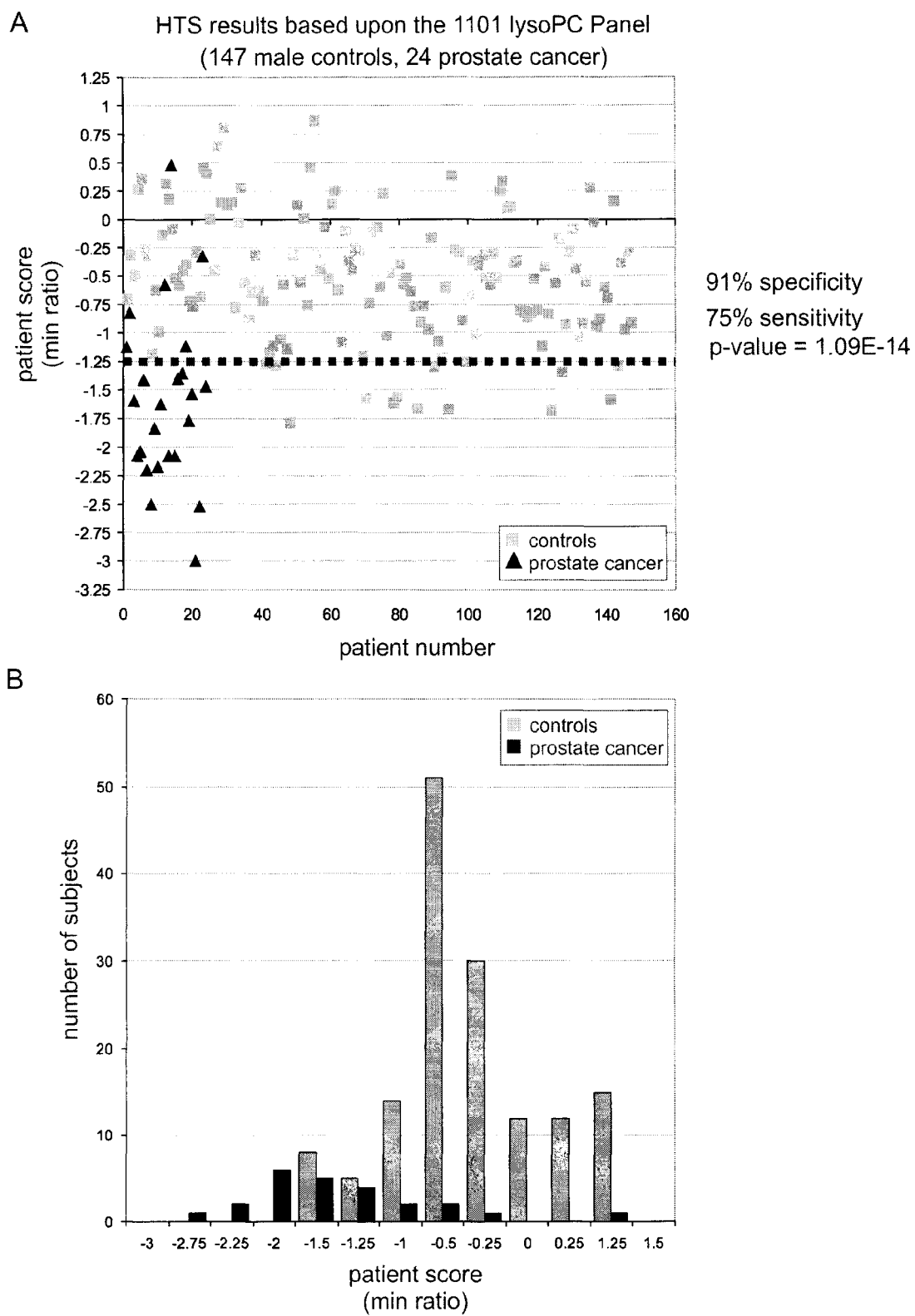
FIG. 22 shows A), a scatter plot of the positive ESI HTS patient scores for 147 male controls (grey squeares) and 24 prostate cancer patients (black triangles). B), frequency histogram showing the distribution of the control population (grey) and prostate cancer subjects (black) according to binned patient scores.

The final patient scores (lowest detected log ratio per patient) for these subjects are shown in the scatter plot in FIG. 22A. The results clearly show that the patient scores of the 24 prostate cancer patients (black triangles) were significantly lower than most of the disease-free male subjects (light grey squares). Plotting the distributions of the subjects based upon the patient score, as shown in FIG. 22B, mirrored the previous findings and showed a shift in the distribution of the prostate patients (black bars) to the left, indicating an overall lower patient score in the majority of prostate cancer patients relative to the controls. Setting a cut-off patient score of −1.25, indicated by the dotted line in FIG. 22A, resulted in approximately 75% sensitivity (that is, 75% of the cancer patients have scores of less than −1.25), and 91% specificity (that is, 91% of the control male population has a score greater than −1.25). The p-value generated from a t-test using the patient scores was 1.09E-14 between the controls and prostate cancer samples.

Figure 23:
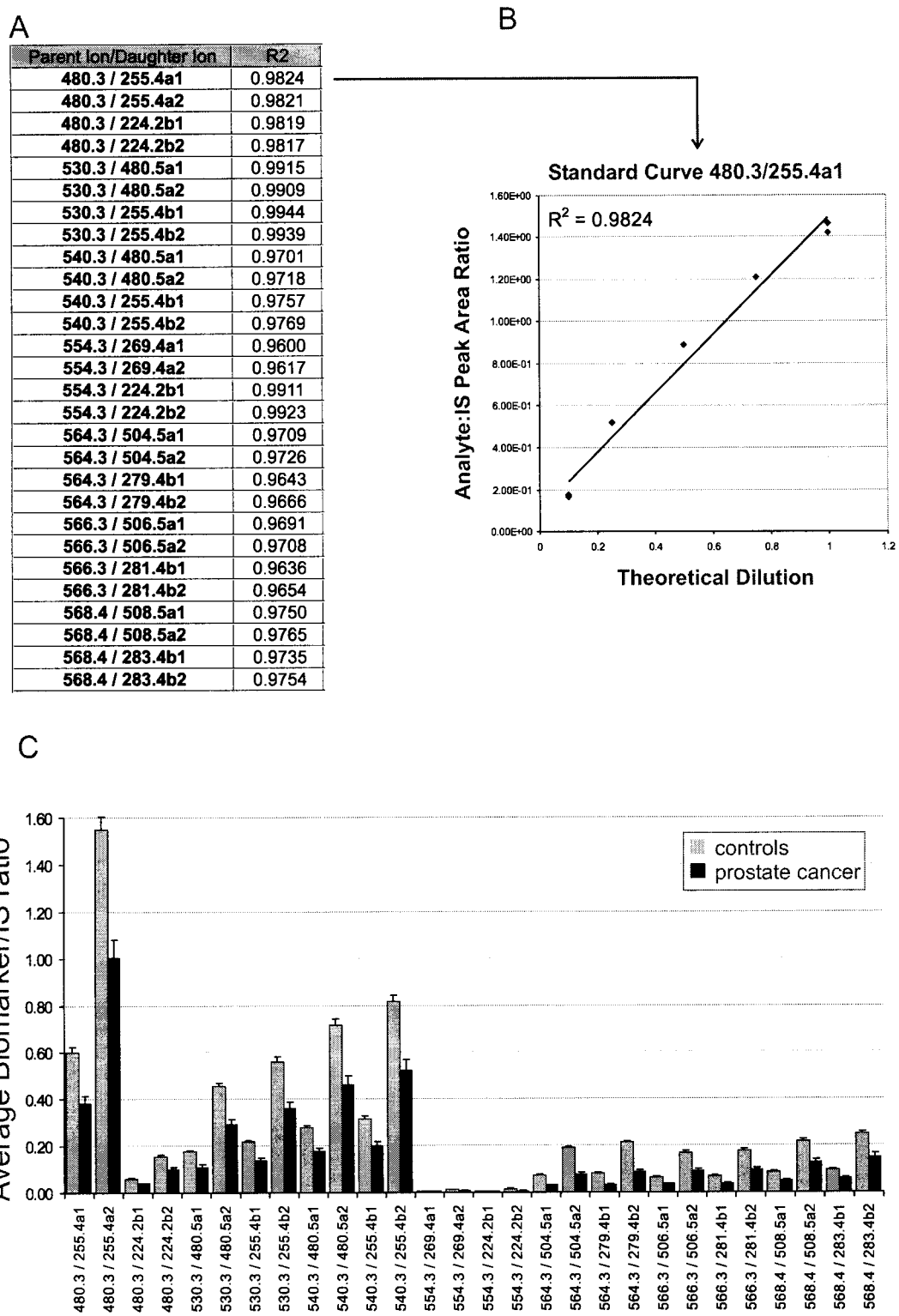
FIG. 23 shows A), the list of the parent-daughter ion transitions used for the negative ESI triple-quadrupole HTS method as well as the R-squared correlation coefficient resulting from calculation of linearity across five diluted samples. B), Standard curve for transition 480.3/255.4a1. C). The average ratio (biomarker:IS peak area) for each transition in the prostate (black) and control (grey) subjects.

For the seven lysolipid species detected in the negative mode (481.3171, 531.3123, 541.3422, 555.3101, 565.3394, 567.3546, and 569.3687), the daughter ion transitions for the HTS method are shown in FIG. 23A. The method is similar to the positive mode, with four ratios (from two internal standard measurements) generated per parent ion, resulting in 28 total ratios per patient sample. The average r-squared values resulting from the analysis of multiple diluted serum samples for each of the ratios is also shown in FIG. 23A. A plot of the standard curve for the first transition ratio (480.3/255.4a1) is shown in FIG. 23 B as an example. As expected, the ratios for each of the transitions was lower in the prostate cancer cohort relative to the controls, as shown in the bar graph in FIG. 23C.

Figure 24:
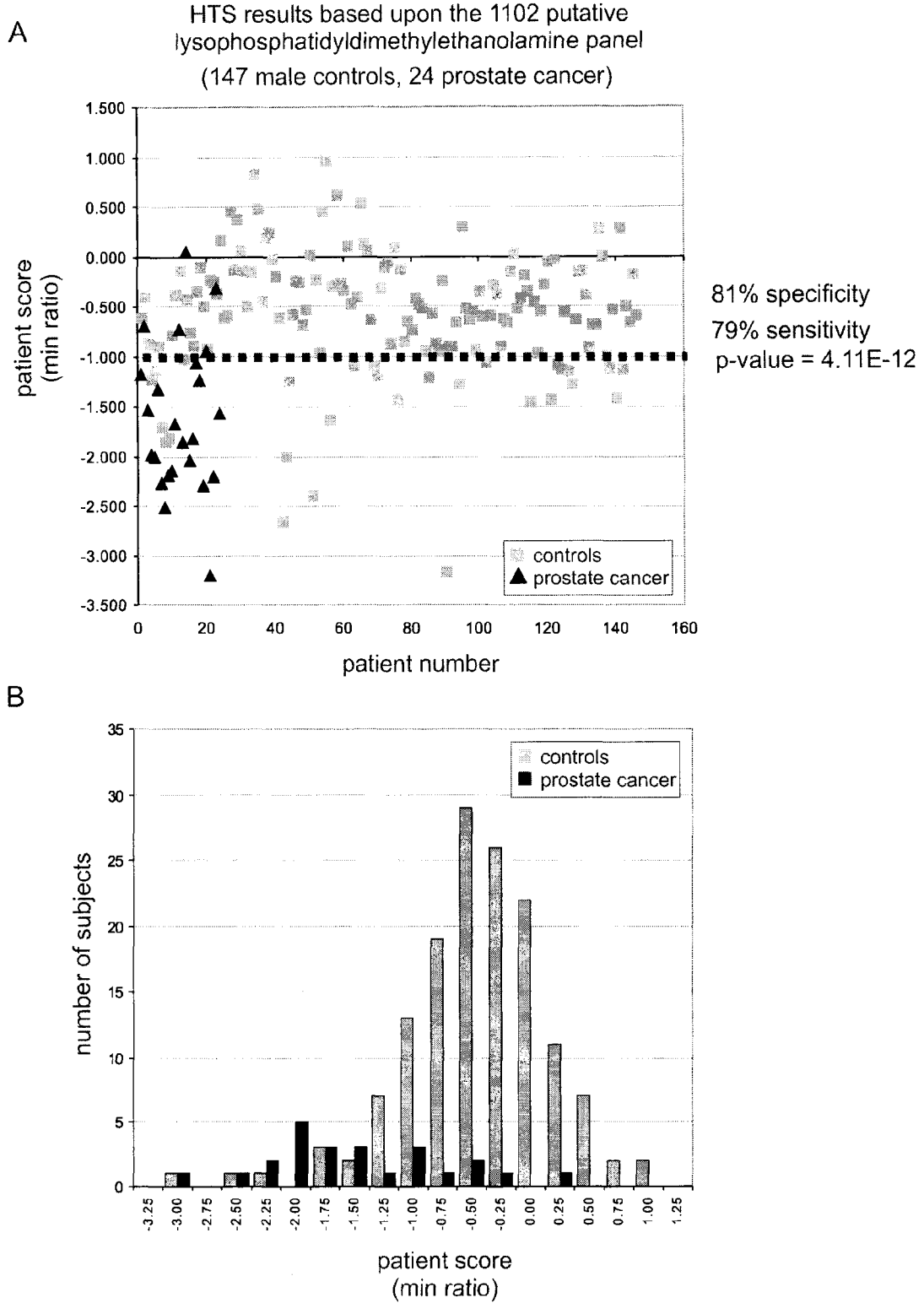
FIG. 24 shows A), a scatter plot of the negative ESI HTS patient scores for 147 male controls (grey squeares) and 24 prostate cancer patients (black triangles). B), frequency histogram showing the distribution of the control population (grey) and prostate cancer subjects (black) according to binned patient scores.

The final patient scores (lowest detected log ratio per patient) for the seven metabolites detected in the negative mode are shown in the scatter plot in FIG. 24A. The results clearly show that the patient scores of the 24 prostate cancer patients (black triangles) were significantly lower than most of the disease-free male subjects (light grey squares). Plotting the distributions of the subjects based upon the patient score, as shown in FIG. 24B, mirrored the previous findings and showed a shift in the distribution of the prostate patients (black bars) to the left, indicating an overall lower patient score in the majority of prostate cancer patients relative to the controls. Setting a cut-off patient score of −1.00, indicated by the dotted line in FIG. 24A, results in approximately 79% sensitivity (that is, 79% of the cancer patients have scores of less than −1.00), and 81% specificity (that is, 81% of the control male population has a score greater than −1.25). The p-value generated from a t-test using the patient scores was 4.11E-14 between the controls and prostate cancer samples.

As would be known to a person of skill in the art, the cut-off value could be move either up or down to favor either sensitivity or specificity, respectively. This performance is superior to that achievable with PSA testing. Since this method is accurate and can be run rapidly on a serum sample, screening the male population would be expected to identify otherwise undetected cases, and would therefore have a major impact on prostate cancer mortality.

As would also be known to a person of skill in the art, various subsets of the measured transitions and ratios thereof could be used to optimize the diagnostic accuracy. Likewise, performing serial analysis of each of the positive and negative modes and then stacking or combining the results may also improve the sensitivity and specificity. For example, patients incorrectly diagnosed using only one method (positive mode) may be correctly classified with the negative mode, or vise-versa. Alternatively, data from both positive and negative modes could be acquired first, followed by the generation of a single patient score based upon the total cumulative dataset.

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

1. Troyer D A, Mubiru J, Leach R J, Naylor S L. Promise and challenge: Markers of prostate cancer detection, diagnosis and prognosis. Dis Markers 2004; 20(2): 117-28.
2. Mettlin C J, Murphy G P, Rosenthal D S, Menck H R. The National Cancer Data Base report on prostate carcinoma after the peak in incidence rates in the U.S. The American College of Surgeons Commission on Cancer and the American Cancer Society. Cancer 1998; 83(8):1679-84.
3. Thompson I M, Goodman P J, Tangen C M, et al. The influence of finasteride on the development of prostate cancer. N Engl J Med 2003; 349(3):215-24.
4. Gann P H, Hennekens C H, Stampfer M J. A prospective evaluation of plasma prostate-specific antigen for detection of prostatic cancer. Jama 1995; 273(4):289-94.
5. Schroder F H, van der Cruijsen-Koeter I, de Koning H J, Vis A N, Hoedemaeker R F, Kranse R. Prostate cancer detection at low prostate specific antigen. The Journal of urology 2000; 163(3):806-12.
6. Reo N V. NMR-based metabolomics. Drug Chem Toxicol 2002; 25(4):375-82.
7. Taylor J, King R D, Altmann T, Fiehn O. Application of metabolomics to plant genotype discrimination using statistics and machine learning. Bioinformatics 2002; 18 Suppl 2:S241-8.
8. Katajamaa M, Oresic M. Processing methods for differential analysis of LC/MS profile data. BMC Bioinformatics 2005; 6:179.
9. Aharoni A, Ric de Vos C H, Verhoeven H A, et al. Nontargeted metabolome analysis by use of Fourier Transform Ion Cyclotron Mass Spectrometry. Omics 2002; 6(3):217-34.
10. Hirai M Y, Klein M, Fujikawa Y, et al. Elucidation of gene-to-gene and metabolite-to-gene networks in arabidopsis by integration of metabolomics and transcriptomics. The Journal of biological chemistry 2005; 280(27): 25590-5.
11. Hirai M Y, Yano M, Goodenowe D B, et al. Integration of transcriptomics and metabolomics for understanding of global responses to nutritional stresses in *Arabidopsis thaliana*. Proceedings of the National Academy of Sciences of the United States of America 2004; 101(27): 10205-10.
12. Okajima F, Sato K, Tomura H, et al. Stimulatory and inhibitory actions of lysophosphatidylcholine, depending on its fatty acid residue, on the phospholipase C/Ca2+ system in HL-60 leukaemia cells. The Biochemical journal 1998; 336 (Pt 2):491-500.
13. Hopfgartner G, Varesio E, Tschappat V, Grivet C, Bourgogne E, Leuthold L A. Triple quadrupole linear ion trap mass spectrometer for the analysis of small molecules and macromolecules. J Mass Spectrom 2004; 39(8):845-55.
14. Xia Y Q, Miller J D, Bakhtiar R, Franklin R B, Liu D Q. Use of a quadrupole linear ion trap mass spectrometer in metabolite identification and bioanalysis. Rapid Commun Mass Spectrom 2003; 17(11):1137-45.

TABLE 1

List of metabolites discriminating prostate cancer-positive from normal serum ($p < 0.05$).

| Detected Mass | Analysis Mode | P_Value | Avg. Normal (log2) | StDev. Normal | Avg. Prostate (log2) | StDev. Prostate | Normal/Prostate (log2 ratio) |
|---|---|---|---|---|---|---|---|
| 174.1408 | 1203 | 0.0079 | 1.85 | 0.25 | 1.62 | 0.32 | 1.14 |
| 188.1566 | 1203 | 0.0227 | 1.46 | 0.36 | 1.12 | 0.63 | 1.31 |
| 194.0804 | 1203 | 0.0001 | 0.72 | 0.8 | 0 | 0 | 0.72 |
| 202.0454 | 1101 | 0.0279 | 2.58 | 1.09 | 3.15 | 0.59 | 0.82 |
| 205.8867 | 1101 | 0.048 | 2.81 | 0.28 | 2.96 | 0.21 | 0.95 |
| 216.0401 | 1102 | 0.0216 | 3.02 | 0.84 | 3.5 | 0.51 | 0.86 |
| 218.0372 | 1102 | 0.0137 | 1.35 | 0.78 | 1.85 | 0.58 | 0.73 |
| 226.0687 | 1102 | 0.0163 | 1.94 | 0.86 | 2.49 | 0.67 | 0.78 |
| 228.1476 | 1101 | 0.0001 | 0.07 | 0.36 | 1.25 | 1.28 | 0.06 |
| 232.9133 | 1202 | 0.0049 | 2.46 | 0.22 | 2.04 | 0.68 | 1.21 |
| 242.2251 | 1204 | 0.0024 | 2.02 | 0.32 | 1.68 | 0.42 | 1.2 |
| 243.0719 | 1101 | 0.0116 | 4.53 | 0.79 | 5.04 | 0.54 | 0.9 |
| 244.056 | 1101 | 0.0043 | 1.54 | 1.14 | 2.41 | 0.87 | 0.64 |
| 247.9578 | 1102 | 0.0003 | 0 | 0 | 1.58 | 2 | 0 |
| 252.2096 | 1204 | 0.0063 | 1.84 | 0.33 | 1.44 | 0.61 | 1.28 |
| 258.2482 | 1204 | 0.0421 | 1.97 | 0.33 | 1.77 | 0.33 | 1.11 |
| 268.2412 | 1204 | 0.0209 | 2.42 | 0.42 | 2.15 | 0.36 | 1.12 |
| 272.2357 | 1204 | 0.0307 | 2.75 | 0.52 | 2.45 | 0.44 | 1.13 |
| 273.874 | 1101 | 0.0349 | 2.76 | 0.29 | 2.93 | 0.23 | 0.94 |
| 276.2096 | 1204 | 0.0001 | 2.77 | 0.46 | 2.24 | 0.42 | 1.24 |
| 278.2256 | 1204 | 0.0013 | 4.95 | 0.42 | 4.54 | 0.42 | 1.09 |
| 279.2287 | 1204 | 0.0047 | 2.83 | 0.47 | 2.44 | 0.45 | 1.16 |
| 280.2414 | 1204 | 0.0401 | 8.14 | 0.45 | 7.89 | 0.36 | 1.03 |
| 281.2448 | 1204 | 0.0352 | 5.77 | 0.45 | 5.52 | 0.36 | 1.05 |
| 283.2602 | 1204 | 0.0475 | 6.56 | 0.42 | 6.33 | 0.38 | 1.04 |
| 283.9028 | 1101 | 0.0061 | 3.14 | 0.33 | 3.36 | 0.2 | 0.93 |
| 292.204 | 1204 | 0.0096 | 1.9 | 0.54 | 1.48 | 0.57 | 1.29 |
| 296.2358 | 1204 | 0.0229 | 4.48 | 0.55 | 4.16 | 0.38 | 1.08 |
| 298.2519 | 1204 | 0.004 | 4.74 | 0.5 | 4.35 | 0.38 | 1.09 |
| 299.2558 | 1204 | 0.0034 | 2.51 | 0.49 | 2.13 | 0.37 | 1.18 |
| 300.2098 | 1204 | 0.0026 | 1.83 | 0.33 | 1.37 | 0.64 | 1.34 |
| 300.2676 | 1204 | 0.0001 | 1.26 | 0.63 | 0.49 | 0.63 | 2.59 |
| 302.2256 | 1204 | 8.97E−06 | 3.69 | 0.4 | 3.05 | 0.5 | 1.21 |
| 304.2394 | 1202 | 0.0088 | 4.39 | 0.47 | 4.03 | 0.45 | 1.09 |
| 304.241 | 1204 | 1.34E−05 | 5.07 | 0.31 | 4.64 | 0.32 | 1.09 |
| 305.243 | 1202 | 0.0123 | 2.4 | 0.68 | 1.8 | 0.91 | 1.33 |
| 305.2439 | 1204 | 0.0001 | 2.77 | 0.32 | 2.34 | 0.36 | 1.19 |
| 306.257 | 1204 | 0.0003 | 3.14 | 0.39 | 2.65 | 0.5 | 1.19 |
| 308.2715 | 1204 | 0.0171 | 1.96 | 0.58 | 1.54 | 0.62 | 1.28 |
| 310.2154 | 1204 | 0.0128 | 2.29 | 0.47 | 1.99 | 0.32 | 1.15 |
| 310.2884 | 1204 | 0.0322 | 2.39 | 0.52 | 2.03 | 0.62 | 1.18 |
| 312.2313 | 1204 | 0.0018 | 2.69 | 0.33 | 2.41 | 0.26 | 1.12 |
| 312.304 | 1204 | 0.0013 | 1.22 | 0.82 | 0.51 | 0.62 | 2.41 |
| 314.2464 | 1204 | 0.0049 | 1.88 | 0.37 | 1.45 | 0.63 | 1.3 |
| 317.9626 | 1101 | 0.0053 | 0.86 | 1.23 | 1.81 | 1.02 | 0.48 |
| 320.2358 | 1204 | 4.37E−05 | 1.86 | 0.56 | 0.99 | 0.77 | 1.87 |
| 326.2262 | 1204 | 0.0052 | 1.79 | 1.03 | 0.96 | 0.95 | 1.87 |
| 326.2476 | 1204 | 0.0425 | 0.79 | 0.68 | 1.18 | 0.59 | 0.68 |
| 327.0326 | 1204 | 0.002 | 2.61 | 0.31 | 2.32 | 0.32 | 1.13 |
| 328.2628 | 1204 | 0.0356 | 1.75 | 0.25 | 1.93 | 0.31 | 0.91 |
| 329.2426 | 1202 | 0.0399 | 1.25 | 1 | 0.67 | 0.91 | 1.86 |
| 329.2445 | 1204 | 0.0147 | 0.91 | 0.83 | 0.39 | 0.59 | 2.33 |
| 330.2568 | 1204 | 0.0428 | 2.25 | 0.4 | 1.93 | 0.66 | 1.17 |
| 331.8326 | 1101 | 0.0273 | 2.7 | 0.32 | 2.89 | 0.26 | 0.93 |
| 339.9964 | 1101 | 0.0003 | 1.94 | 0.95 | 2.77 | 0.43 | 0.7 |
| 340.2977 | 1203 | 0.0156 | 2.4 | 0.41 | 2.12 | 0.36 | 1.13 |
| 341.8614 | 1101 | 0.017 | 3.34 | 0.39 | 3.58 | 0.27 | 0.93 |
| 342.2198 | 1204 | 0.0159 | 0.71 | 0.82 | 0.22 | 0.52 | 3.27 |
| 351.8906 | 1101 | 0.0391 | 3.38 | 0.41 | 3.59 | 0.25 | 0.94 |
| 354.1668 | 1202 | 0.0008 | 0 | 0 | 1.08 | 1.51 | 0 |
| 368.3437 | 1203 | 0.0146 | 10.86 | 0.29 | 10.67 | 0.24 | 1.02 |
| 369.3474 | 1203 | 0.0232 | 9.26 | 0.25 | 9.1 | 0.22 | 1.02 |
| 371.3538 | 1203 | 0.0087 | 3.05 | 0.27 | 2.84 | 0.26 | 1.07 |
| 382.2903 | 1204 | 0.0045 | 0.04 | 0.18 | 0.61 | 0.94 | 0.06 |
| 392.294 | 1204 | 0.0001 | 1.81 | 0.96 | 0.63 | 1 | 2.88 |
| 411.3186 | 1202 | 0.0044 | 2.99 | 0.29 | 2.74 | 0.3 | 1.09 |
| 430.3083 | 1204 | 0.0003 | 2.09 | 0.28 | 1.82 | 0.2 | 1.15 |
| 430.3818 | 1204 | 0.0064 | 4.04 | 0.69 | 3.5 | 0.63 | 1.15 |
| 431.3861 | 1204 | 0.0169 | 2.53 | 0.65 | 2.11 | 0.52 | 1.2 |
| 432.3686 | 1204 | 0.0107 | 1.6 | 0.9 | 0.87 | 1.01 | 1.84 |
| 452.2536 | 1204 | 0.0023 | 1.71 | 0.34 | 1.21 | 0.69 | 1.41 |
| 472.3925 | 1203 | 0.0052 | 3.93 | 0.51 | 4.32 | 0.41 | 0.91 |
| 473.3957 | 1203 | 0.0122 | 2.46 | 0.52 | 2.83 | 0.47 | 0.87 |
| 481.3171 | 1102 | 3.99E−09 | 1.79 | 0.36 | 0.86 | 0.53 | 2.08 |

TABLE 1-continued

List of metabolites discriminating prostate cancer-positive from normal serum (p < 0.05).

| Detected Mass | Analysis Mode | P_Value | Avg. Normal (log2) | StDev. Normal | Avg. Prostate (log2) | StDev. Prostate | Normal/Prostate (log2 ratio) |
|---|---|---|---|---|---|---|---|
| 481.3172 | 1202 | 0.006 | 4.19 | 0.25 | 3.98 | 0.27 | 1.05 |
| 482.3216 | 1202 | 0.0265 | 2.28 | 0.28 | 2.09 | 0.3 | 1.09 |
| 484.3792 | 1204 | 0.0432 | 1.8 | 0.7 | 1.32 | 0.89 | 1.36 |
| 492.4184 | 1203 | 0.0025 | 0.69 | 0.94 | 0.05 | 0.26 | 12.93 |
| 494.4344 | 1203 | 0.01 | 1.92 | 1.56 | 0.9 | 1.04 | 2.13 |
| 495.3328 | 1101 | 4.45E−08 | 4.22 | 0.38 | 3.23 | 0.65 | 1.3 |
| 495.4376 | 1203 | 0.023 | 0.81 | 1.11 | 0.22 | 0.51 | 3.63 |
| 496.336 | 1101 | 2.57E−08 | 2.68 | 0.34 | 1.74 | 0.6 | 1.53 |
| 501.2848 | 1201 | 0.0053 | 1.47 | 0.97 | 0.75 | 0.75 | 1.97 |
| 505.3227 | 1202 | 0.0005 | 4.17 | 0.3 | 3.85 | 0.3 | 1.08 |
| 506.3213 | 1202 | 0.0007 | 2.66 | 0.29 | 2.35 | 0.32 | 1.13 |
| 507.3317 | 1202 | 0.0258 | 3.02 | 0.26 | 2.84 | 0.28 | 1.06 |
| 509.3493 | 1202 | 0.0021 | 2.69 | 0.26 | 2.39 | 0.38 | 1.13 |
| 517.3148 | 1101 | 2.98E−08 | 4.38 | 0.36 | 3.3 | 0.72 | 1.33 |
| 518.3182 | 1101 | 5.20E−08 | 2.42 | 0.32 | 1.33 | 0.78 | 1.82 |
| 518.4345 | 1203 | 0.0043 | 1.33 | 1.08 | 0.52 | 0.79 | 2.57 |
| 519.332 | 1201 | 0.0008 | 2.68 | 0.73 | 2.04 | 0.5 | 1.31 |
| 519.3328 | 1101 | 2.80E−09 | 2.6 | 0.57 | 1.12 | 0.82 | 2.31 |
| 520.4502 | 1203 | 0.0049 | 3.69 | 0.97 | 2.88 | 0.96 | 1.28 |
| 521.348 | 1101 | 3.30E−09 | 2.35 | 0.38 | 1.34 | 0.57 | 1.75 |
| 521.4526 | 1203 | 0.0189 | 1.97 | 1.04 | 1.32 | 0.82 | 1.49 |
| 522.464 | 1203 | 0.0092 | 4.68 | 0.96 | 3.93 | 0.98 | 1.19 |
| 523.364 | 1101 | 2.06E−08 | 2.54 | 0.44 | 1.52 | 0.62 | 1.68 |
| 523.4678 | 1203 | 0.0083 | 3.27 | 0.93 | 2.55 | 0.91 | 1.28 |
| 524.4725 | 1203 | 0.0053 | 1.08 | 0.92 | 0.39 | 0.72 | 2.77 |
| 529.3167 | 1202 | 0.011 | 3.32 | 0.32 | 3.06 | 0.38 | 1.09 |
| 531.3123 | 1102 | 1.22E−09 | 2.39 | 0.3 | 1.49 | 0.51 | 1.61 |
| 534.4645 | 1204 | 0.039 | 1.34 | 0.8 | 0.85 | 0.83 | 1.58 |
| 538.501 | 1204 | 0.0479 | 0.93 | 0.86 | 0.48 | 0.71 | 1.97 |
| 541.3148 | 1101 | 4.07E−09 | 2.56 | 0.59 | 1.07 | 0.84 | 2.39 |
| 541.3422 | 1102 | 5.17E−10 | 4.45 | 0.36 | 3.47 | 0.51 | 1.28 |
| 541.3433 | 1202 | 0.0241 | 6.11 | 0.34 | 5.89 | 0.31 | 1.04 |
| 542.3453 | 1102 | 1.47E−10 | 2.65 | 0.35 | 1.8 | 0.38 | 1.47 |
| 542.3461 | 1202 | 0.0215 | 4.21 | 0.27 | 4.03 | 0.26 | 1.04 |
| 545.346 | 1101 | 3.41E−08 | 2.48 | 0.48 | 1.2 | 0.84 | 2.07 |
| 548.4817 | 1203 | 0.0358 | 6.91 | 0.53 | 6.58 | 0.51 | 1.05 |
| 549.4848 | 1203 | 0.0347 | 5.47 | 0.54 | 5.14 | 0.53 | 1.06 |
| 552.3825 | 1201 | 0.0061 | 0 | 0 | 0.43 | 0.75 | 0 |
| 552.4048 | 1204 | 0.0167 | 0.75 | 0.71 | 0.3 | 0.55 | 2.53 |
| 555.3101 | 1102 | 9.86E−09 | 1.94 | 0.48 | 0.84 | 0.62 | 2.32 |
| 565.3393 | 1202 | 0.0128 | 7.07 | 0.37 | 6.83 | 0.28 | 1.04 |
| 565.3394 | 1102 | 5.30E−09 | 4.17 | 0.49 | 3.13 | 0.54 | 1.33 |
| 566.3433 | 1102 | 7.66E−09 | 2.44 | 0.49 | 1.5 | 0.44 | 1.62 |
| 566.3434 | 1202 | 0.0017 | 5.4 | 0.31 | 5.11 | 0.3 | 1.06 |
| 567.3546 | 1202 | 0.0468 | 6.01 | 0.3 | 5.84 | 0.28 | 1.03 |
| 567.3548 | 1102 | 5.18E−10 | 3.41 | 0.41 | 2.48 | 0.43 | 1.38 |
| 568.3573 | 1102 | 1.36E−06 | 1.53 | 0.48 | 0.68 | 0.58 | 2.23 |
| 568.3574 | 1202 | 0.0494 | 4.01 | 0.3 | 3.84 | 0.29 | 1.04 |
| 569.3687 | 1102 | 6.16E−08 | 3.13 | 0.41 | 2.14 | 0.64 | 1.46 |
| 569.3691 | 1202 | 0.0043 | 5.16 | 0.23 | 4.91 | 0.35 | 1.05 |
| 570.3726 | 1202 | 0.0047 | 3.28 | 0.23 | 3.04 | 0.33 | 1.08 |
| 570.4653 | 1203 | 0.0021 | 2.21 | 0.39 | 1.71 | 0.65 | 1.29 |
| 570.4915 | 1204 | 0.0089 | 0.67 | 0.8 | 0.15 | 0.5 | 4.56 |
| 579.5322 | 1203 | 0.0008 | 4.45 | 0.6 | 3.84 | 0.59 | 1.16 |
| 580.5345 | 1203 | 0.0006 | 2.21 | 0.71 | 1.4 | 0.83 | 1.58 |
| 582.2469 | 1201 | 0.0261 | 2.44 | 0.97 | 3.02 | 0.8 | 0.81 |
| 583.2504 | 1201 | 0.042 | 1.11 | 0.83 | 1.58 | 0.75 | 0.7 |
| 587.3228 | 1202 | 0.0276 | 2.22 | 0.91 | 1.61 | 0.94 | 1.37 |
| 589.3401 | 1102 | 3.62E−07 | 2.73 | 0.42 | 1.86 | 0.6 | 1.47 |
| 589.3404 | 1202 | 0.0246 | 6.25 | 0.37 | 5.98 | 0.42 | 1.04 |
| 590.343 | 1202 | 0.0253 | 4.37 | 0.37 | 4.12 | 0.38 | 1.06 |
| 590.4597 | 1204 | 0.0219 | 2.54 | 0.57 | 2.13 | 0.65 | 1.2 |
| 596.4794 | 1203 | 0.0012 | 3.36 | 0.42 | 2.88 | 0.55 | 1.17 |
| 599.4932 | 1204 | 0.0151 | 1.76 | 0.91 | 1.07 | 0.99 | 1.64 |
| 601.5077 | 1204 | 0.0428 | 1.65 | 0.83 | 1.14 | 0.92 | 1.46 |
| 604.5441 | 1203 | 0.0002 | 6.45 | 0.49 | 5.89 | 0.49 | 1.1 |
| 605.5469 | 1203 | 0.0002 | 4.94 | 0.51 | 4.37 | 0.5 | 1.13 |
| 609.3242 | 1102 | 9.76E−08 | 2.04 | 0.35 | 1.18 | 0.58 | 1.72 |
| 612.5004 | 1204 | 0.0149 | 1.85 | 0.69 | 1.27 | 0.9 | 1.46 |
| 615.4797 | 1204 | 0.0001 | 3.22 | 0.37 | 2.77 | 0.38 | 1.16 |
| 622.4973 | 1203 | 0.0126 | 3.29 | 0.59 | 2.89 | 0.51 | 1.14 |
| 623.4918 | 1204 | 0.0366 | 1.79 | 0.94 | 1.21 | 0.93 | 1.48 |
| 623.5003 | 1203 | 0.006 | 2.19 | 0.6 | 1.59 | 0.83 | 1.37 |
| 624.5134 | 1203 | 0.0003 | 4.04 | 0.39 | 3.6 | 0.4 | 1.12 |

TABLE 1-continued

List of metabolites discriminating prostate cancer-positive from normal serum (p < 0.05).

| Detected Mass | Analysis Mode | P_Value | Avg. Normal (log2) | StDev. Normal | Avg. Prostate (log2) | StDev. Prostate | Normal/Prostate (log2 ratio) |
|---|---|---|---|---|---|---|---|
| 625.5078 | 1204 | 0.0259 | 3.76 | 0.64 | 3.36 | 0.54 | 1.12 |
| 625.5163 | 1203 | 0.0005 | 2.86 | 0.4 | 2.42 | 0.43 | 1.18 |
| 626.5109 | 1204 | 0.014 | 2.63 | 0.59 | 2.17 | 0.67 | 1.21 |
| 626.5285 | 1203 | 1.19E−05 | 3.78 | 0.36 | 3.28 | 0.37 | 1.15 |
| 627.5204 | 1204 | 0.015 | 4.62 | 0.59 | 4.21 | 0.55 | 1.1 |
| 627.5306 | 1203 | 0.0006 | 2.52 | 0.41 | 2.06 | 0.47 | 1.23 |
| 628.5236 | 1204 | 0.0103 | 3.32 | 0.61 | 2.86 | 0.6 | 1.16 |
| 628.5426 | 1203 | 0.0017 | 3.22 | 0.45 | 2.76 | 0.5 | 1.16 |
| 629.5453 | 1203 | 0.0275 | 1.95 | 0.66 | 1.46 | 0.83 | 1.33 |
| 630.5582 | 1203 | 0.0078 | 2.78 | 0.68 | 2.32 | 0.46 | 1.2 |
| 632.5752 | 1203 | 1.91E−06 | 1.46 | 0.85 | 0.3 | 0.61 | 4.83 |
| 635.5246 | 1204 | 0.0253 | 1.7 | 1 | 1.07 | 0.89 | 1.58 |
| 641.4915 | 1204 | 0.0036 | 2.19 | 1.03 | 1.19 | 1.23 | 1.83 |
| 646.5709 | 1203 | 0.0008 | 3.54 | 0.6 | 2.92 | 0.59 | 1.21 |
| 647.574 | 1203 | 0.0008 | 2.72 | 0.58 | 2.06 | 0.71 | 1.32 |
| 647.6063 | 1204 | 0.0044 | 2.09 | 0.62 | 1.39 | 0.97 | 1.5 |
| 648.5865 | 1203 | 0.0007 | 5.73 | 0.44 | 5.2 | 0.56 | 1.1 |
| 649.5056 | 1204 | 0.0255 | 2.61 | 0.91 | 2.02 | 0.91 | 1.3 |
| 649.5898 | 1203 | 0.0015 | 4.69 | 0.48 | 4.17 | 0.59 | 1.12 |
| 655.5509 | 1204 | 0.0006 | 2.79 | 0.57 | 1.87 | 1.1 | 1.49 |
| 660.5005 | 1204 | 0.0059 | 1.38 | 0.97 | 0.62 | 0.86 | 2.22 |
| 660.6082 | 1203 | 0.0116 | 0.41 | 0.77 | 0 | 0 | 0.41 |
| 663.4864 | 1204 | 0.0311 | 1.49 | 1.27 | 0.76 | 1.03 | 1.97 |
| 670.5688 | 1204 | 9.11E−06 | 3.86 | 0.42 | 3.2 | 0.51 | 1.21 |
| 670.5711 | 1203 | 0.0142 | 1.69 | 0.89 | 1.03 | 0.92 | 1.64 |
| 671.5723 | 1204 | 0.0003 | 2.92 | 0.4 | 2.17 | 0.85 | 1.34 |
| 672.5865 | 1203 | 0.0034 | 4.47 | 0.61 | 3.91 | 0.65 | 1.14 |
| 673.5893 | 1203 | 0.003 | 3.66 | 0.57 | 3.13 | 0.61 | 1.17 |
| 673.6185 | 1204 | 0.0174 | 3.07 | 0.49 | 2.63 | 0.74 | 1.17 |
| 673.6224 | 1203 | 0.0032 | 2.74 | 0.45 | 2.37 | 0.4 | 1.16 |
| 675.6359 | 1203 | 0.001 | 3.37 | 0.37 | 3 | 0.37 | 1.12 |
| 675.6375 | 1204 | 0.0047 | 3.89 | 0.48 | 3.33 | 0.82 | 1.17 |
| 676.6393 | 1203 | 0.0009 | 2.24 | 0.36 | 1.78 | 0.54 | 1.26 |
| 680.5625 | 1204 | 0.0293 | 3.86 | 0.65 | 3.48 | 0.52 | 1.11 |
| 684.5487 | 1204 | 0.0001 | 3.11 | 0.37 | 2.63 | 0.44 | 1.18 |
| 685.5543 | 1204 | 0.0001 | 2.7 | 0.37 | 2.1 | 0.61 | 1.29 |
| 686.5126 | 1204 | 0.0469 | 2.49 | 0.86 | 1.92 | 1.09 | 1.3 |
| 688.5294 | 1204 | 0.0081 | 2.9 | 0.43 | 2.46 | 0.68 | 1.18 |
| 690.4849 | 1204 | 0.0399 | 2.37 | 0.6 | 1.98 | 0.69 | 1.2 |
| 690.547 | 1204 | 0.0008 | 2.36 | 0.39 | 1.73 | 0.77 | 1.36 |
| 692.5571 | 1204 | 0.017 | 3.07 | 0.63 | 2.65 | 0.54 | 1.16 |
| 693.611 | 1204 | 0.0396 | 3.79 | 0.5 | 3.39 | 0.8 | 1.12 |
| 695.647 | 1204 | 0.0043 | 2.54 | 1.08 | 1.36 | 1.63 | 1.87 |
| 696.5856 | 1203 | 0.0318 | 1.14 | 0.98 | 0.59 | 0.73 | 1.93 |
| 696.651 | 1204 | 0.0448 | 1.53 | 1.17 | 0.81 | 1.28 | 1.89 |
| 699.5205 | 1204 | 0.0002 | 2.61 | 0.75 | 1.63 | 0.93 | 1.6 |
| 702.5675 | 1101 | 6.42E−08 | 2.87 | 0.29 | 2.12 | 0.5 | 1.35 |
| 705.6083 | 1204 | 0.0303 | 2.82 | 0.49 | 2.44 | 0.69 | 1.16 |
| 707.6256 | 1204 | 0.0361 | 4.27 | 0.43 | 3.83 | 0.93 | 1.12 |
| 708.6308 | 1204 | 0.0242 | 3.26 | 0.44 | 2.86 | 0.74 | 1.14 |
| 710.4923 | 1204 | 0.0087 | 2.32 | 0.37 | 1.91 | 0.65 | 1.22 |
| 716.4982 | 1204 | 0.0004 | 2.38 | 0.33 | 1.59 | 0.98 | 1.5 |
| 721.6388 | 1204 | 0.0402 | 5.27 | 0.49 | 4.76 | 1.1 | 1.11 |
| 722.6423 | 1204 | 0.0473 | 4.18 | 0.51 | 3.75 | 0.89 | 1.11 |
| 723.5194 | 1204 | 7.34E−07 | 4.49 | 0.76 | 3.32 | 0.67 | 1.35 |
| 723.5198 | 1202 | 4.42E−07 | 3.17 | 0.64 | 1.96 | 0.81 | 1.62 |
| 724.5247 | 1204 | 9.89E−07 | 3.45 | 0.69 | 2.32 | 0.72 | 1.49 |
| 724.5496 | 1101 | 1.87E−07 | 2.45 | 0.29 | 1.77 | 0.47 | 1.38 |
| 725.5375 | 1204 | 0.0002 | 3.23 | 0.84 | 2.23 | 0.87 | 1.45 |
| 726.5456 | 1204 | 7.10E−06 | 2.81 | 0.37 | 1.89 | 0.82 | 1.48 |
| 727.5565 | 1204 | 1.52E−07 | 3.68 | 0.5 | 2.86 | 0.67 | 1.29 |
| 728.562 | 1204 | 6.41E−07 | 3.01 | 0.36 | 2.23 | 0.58 | 1.35 |
| 729.5724 | 1204 | 2.18E−05 | 2.39 | 0.38 | 1.56 | 0.79 | 1.53 |
| 731.4913 | 1204 | 0.0013 | 5.85 | 0.37 | 5.45 | 0.44 | 1.07 |
| 732.4938 | 1204 | 0.0013 | 4.6 | 0.36 | 4.21 | 0.44 | 1.09 |
| 733.6425 | 1204 | 0.0199 | 3.17 | 0.43 | 2.75 | 0.77 | 1.16 |
| 735.6555 | 1204 | 0.0055 | 4.08 | 0.42 | 3.52 | 0.86 | 1.16 |
| 736.2234 | 1204 | 0.0037 | 0.05 | 0.26 | 0.77 | 1.15 | 0.07 |
| 736.6584 | 1204 | 0.0078 | 2.95 | 0.45 | 2.47 | 0.71 | 1.19 |
| 737.5354 | 1204 | 0.0059 | 1.3 | 1.05 | 0.54 | 0.75 | 2.39 |
| 738.5449 | 1102 | 1.43E−07 | 2.76 | 0.35 | 2.14 | 0.35 | 1.29 |
| 741.5307 | 1204 | 0.0066 | 2.96 | 0.52 | 2.52 | 0.56 | 1.17 |
| 742.5354 | 1204 | 0.0448 | 2.04 | 0.84 | 1.51 | 0.94 | 1.35 |
| 743.5469 | 1202 | 0.0499 | 3.47 | 0.45 | 3.23 | 0.38 | 1.07 |

TABLE 1-continued

List of metabolites discriminating prostate cancer-positive from normal serum (p < 0.05).

| Detected Mass | Analysis Mode | P_Value | Avg. Normal (log2) | StDev. Normal | Avg. Prostate (log2) | StDev. Prostate | Normal/Prostate (log2 ratio) |
|---|---|---|---|---|---|---|---|
| 744.4942 | 1204 | 0.0208 | 4.35 | 0.37 | 4.09 | 0.39 | 1.06 |
| 745.4972 | 1204 | 0.0029 | 3.53 | 0.29 | 3.23 | 0.39 | 1.1 |
| 746.556 | 1102 | 2.28E−05 | 2.02 | 0.3 | 1.37 | 0.62 | 1.47 |
| 747.5201 | 1202 | 0.0001 | 2.64 | 0.55 | 1.95 | 0.6 | 1.36 |
| 747.5234 | 1204 | 0.0007 | 3.91 | 0.52 | 3.36 | 0.52 | 1.16 |
| 748.5279 | 1204 | 0.0025 | 2.81 | 0.53 | 2.25 | 0.7 | 1.25 |
| 748.5722 | 1102 | 2.22E−07 | 4.56 | 0.34 | 3.91 | 0.41 | 1.17 |
| 749.5346 | 1203 | 0.0221 | 0.97 | 1.02 | 0.38 | 0.68 | 2.56 |
| 749.5354 | 1201 | 0.0001 | 2.15 | 0.62 | 1.31 | 0.73 | 1.64 |
| 749.5364 | 1202 | 9.54E−08 | 3.96 | 0.45 | 2.94 | 0.67 | 1.35 |
| 749.5402 | 1204 | 3.67E−06 | 5.01 | 0.64 | 4.11 | 0.55 | 1.22 |
| 749.5763 | 1102 | 8.79E−07 | 3.39 | 0.35 | 2.76 | 0.42 | 1.23 |
| 750.5403 | 1202 | 3.39E−07 | 2.93 | 0.44 | 1.99 | 0.65 | 1.47 |
| 750.5434 | 1204 | 6.74E−07 | 3.86 | 0.58 | 2.94 | 0.54 | 1.31 |
| 751.551 | 1203 | 0.0218 | 1.39 | 1 | 0.78 | 0.77 | 1.78 |
| 751.5529 | 1202 | 3.60E−06 | 4.09 | 0.52 | 3.18 | 0.69 | 1.29 |
| 751.5548 | 1204 | 2.96E−05 | 5.25 | 0.72 | 4.35 | 0.64 | 1.21 |
| 752.5565 | 1202 | 3.61E−06 | 3.01 | 0.51 | 2.17 | 0.6 | 1.39 |
| 752.5578 | 1204 | 2.88E−05 | 4.12 | 0.67 | 3.29 | 0.59 | 1.26 |
| 753.5674 | 1204 | 0.0001 | 2.95 | 0.55 | 2.37 | 0.43 | 1.25 |
| 755.4866 | 1204 | 6.72E−07 | 3.54 | 0.37 | 2.85 | 0.47 | 1.24 |
| 756.4905 | 1204 | 0.0002 | 2.68 | 0.34 | 1.82 | 1.01 | 1.47 |
| 757.5017 | 1204 | 0.0003 | 3.97 | 0.42 | 3.45 | 0.53 | 1.15 |
| 757.5618 | 1101 | 1.53E−06 | 5.41 | 0.44 | 4.65 | 0.52 | 1.16 |
| 758.5089 | 1204 | 0.0007 | 4.94 | 0.36 | 4.53 | 0.43 | 1.09 |
| 758.5654 | 1101 | 1.28E−06 | 4.37 | 0.44 | 3.59 | 0.54 | 1.22 |
| 759.516 | 1204 | 2.72E−05 | 5.22 | 0.34 | 4.67 | 0.48 | 1.12 |
| 759.578 | 1101 | 0.0001 | 4.15 | 0.46 | 3.58 | 0.45 | 1.16 |
| 760.5223 | 1204 | 4.81E−05 | 4.57 | 0.3 | 4.09 | 0.44 | 1.12 |
| 760.5816 | 1101 | 3.36E−05 | 3.04 | 0.45 | 2.44 | 0.46 | 1.24 |
| 761.5269 | 1204 | 2.48E−05 | 3.16 | 0.31 | 2.69 | 0.39 | 1.17 |
| 765.5665 | 1201 | 0.0166 | 2.93 | 0.61 | 2.52 | 0.53 | 1.16 |
| 766.5701 | 1201 | 0.0341 | 1.88 | 0.75 | 1.45 | 0.6 | 1.29 |
| 767.5821 | 1201 | 0.0146 | 3.46 | 0.58 | 3.09 | 0.41 | 1.12 |
| 768.4944 | 1204 | 0.0043 | 3.82 | 0.41 | 3.48 | 0.39 | 1.1 |
| 768.5507 | 1202 | 0.0292 | 2.46 | 0.35 | 2.22 | 0.42 | 1.11 |
| 769.4957 | 1204 | 0.0045 | 3.02 | 0.39 | 2.56 | 0.65 | 1.18 |
| 770.5109 | 1204 | 0.0046 | 3.21 | 0.41 | 2.86 | 0.42 | 1.12 |
| 771.5809 | 1204 | 0.0153 | 4.35 | 0.35 | 4.09 | 0.36 | 1.06 |
| 772.5269 | 1204 | 0.0016 | 3.71 | 0.35 | 3.34 | 0.43 | 1.11 |
| 772.5856 | 1204 | 0.0098 | 3.34 | 0.31 | 3.08 | 0.35 | 1.08 |
| 773.5337 | 1204 | 1.41E−06 | 3.61 | 0.28 | 3.11 | 0.35 | 1.16 |
| 774.5404 | 1204 | 0.0289 | 2.54 | 0.61 | 2.07 | 0.85 | 1.23 |
| 775.553 | 1204 | 0.0039 | 3.63 | 0.52 | 3.19 | 0.5 | 1.14 |
| 775.5533 | 1202 | 0.0031 | 2.58 | 0.44 | 2.11 | 0.6 | 1.22 |
| 776.5563 | 1204 | 0.0039 | 2.64 | 0.46 | 2.09 | 0.77 | 1.26 |
| 776.6057 | 1102 | 0.0029 | 2.16 | 0.46 | 1.62 | 0.73 | 1.33 |
| 776.6069 | 1202 | 0.0388 | 1.81 | 0.66 | 2.13 | 0.34 | 0.85 |
| 777.5679 | 1204 | 0.0026 | 2.97 | 0.51 | 2.57 | 0.33 | 1.15 |
| 779.5438 | 1101 | 5.66E−07 | 5.11 | 0.46 | 4.25 | 0.59 | 1.2 |
| 779.5831 | 1204 | 0.0034 | 2.62 | 0.5 | 2.15 | 0.56 | 1.22 |
| 780.5474 | 1101 | 6.60E−07 | 4.02 | 0.47 | 3.18 | 0.56 | 1.27 |
| 781.5612 | 1101 | 3.67E−07 | 4.91 | 0.41 | 4.11 | 0.53 | 1.19 |
| 782.5087 | 1204 | 0.0001 | 4.12 | 0.36 | 3.58 | 0.48 | 1.15 |
| 782.5649 | 1101 | 2.11E−07 | 3.83 | 0.42 | 3.04 | 0.49 | 1.26 |
| 783.5141 | 1204 | 2.43E−05 | 3.75 | 0.31 | 3.24 | 0.43 | 1.16 |
| 783.578 | 1101 | 1.62E−06 | 3.95 | 0.46 | 3.17 | 0.54 | 1.25 |
| 783.6349 | 1204 | 0.0015 | 0.13 | 0.45 | 0.86 | 0.99 | 0.15 |
| 784.5235 | 1204 | 0.0002 | 3.77 | 0.35 | 3.27 | 0.52 | 1.15 |
| 784.5813 | 1101 | 1.54E−06 | 2.86 | 0.45 | 2.16 | 0.45 | 1.33 |
| 785.5295 | 1204 | 0.0003 | 3.04 | 0.36 | 2.54 | 0.54 | 1.2 |
| 785.5936 | 1101 | 9.67E−06 | 4.24 | 0.41 | 3.57 | 0.53 | 1.19 |
| 786.5404 | 1204 | 2.83E−05 | 4.19 | 0.34 | 3.63 | 0.49 | 1.15 |
| 786.5967 | 1101 | 8.65E−06 | 3.15 | 0.38 | 2.54 | 0.47 | 1.24 |
| 787.5447 | 1204 | 3.19E−05 | 3.18 | 0.33 | 2.67 | 0.45 | 1.19 |
| 793.5387 | 1102 | 1.74E−07 | 3.64 | 0.39 | 2.89 | 0.47 | 1.26 |
| 794.5126 | 1204 | 0.0111 | 2.51 | 0.32 | 1.98 | 0.95 | 1.27 |
| 794.5424 | 1102 | 1.81E−07 | 2.57 | 0.33 | 1.86 | 0.48 | 1.38 |
| 795.5555 | 1102 | 0.0001 | 2.7 | 0.44 | 2.02 | 0.62 | 1.34 |
| 796.5292 | 1204 | 0.0318 | 3.36 | 0.34 | 3.14 | 0.36 | 1.07 |
| 798.6776 | 1203 | 0.0254 | 1.05 | 1.09 | 0.44 | 0.71 | 2.39 |
| 803.5436 | 1101 | 3.89E−07 | 3.81 | 0.45 | 2.87 | 0.65 | 1.33 |
| 803.5685 | 1102 | 3.50E−07 | 6 | 0.46 | 5.19 | 0.5 | 1.16 |
| 804.547 | 1101 | 5.81E−07 | 2.82 | 0.43 | 1.93 | 0.63 | 1.46 |

TABLE 1-continued

List of metabolites discriminating prostate cancer-positive from normal serum (p < 0.05).

| Detected Mass | Analysis Mode | P_Value | Avg. Normal (log2) | StDev. Normal | Avg. Prostate (log2) | StDev. Prostate | Normal/Prostate (log2 ratio) |
|---|---|---|---|---|---|---|---|
| 804.5717 | 1102 | 6.08E−07 | 4.71 | 0.44 | 3.97 | 0.47 | 1.19 |
| 804.7208 | 1204 | 0.0112 | 1.66 | 1.06 | 0.89 | 0.97 | 1.86 |
| 804.7219 | 1203 | 0.009 | 2.47 | 1.05 | 1.6 | 1.19 | 1.55 |
| 805.5606 | 1101 | 2.80E−07 | 4.01 | 0.45 | 3.17 | 0.54 | 1.27 |
| 805.5834 | 1102 | 1.15E−05 | 4.65 | 0.5 | 3.98 | 0.45 | 1.17 |
| 805.7267 | 1203 | 0.042 | 1.47 | 1.19 | 0.83 | 0.97 | 1.78 |
| 806.5643 | 1101 | 2.17E−06 | 3.03 | 0.47 | 2.24 | 0.54 | 1.35 |
| 806.5863 | 1102 | 6.89E−06 | 3.46 | 0.46 | 2.78 | 0.48 | 1.25 |
| 807.5761 | 1101 | 4.54E−06 | 4.24 | 0.41 | 3.56 | 0.51 | 1.19 |
| 808.5795 | 1101 | 3.90E−06 | 3.25 | 0.4 | 2.55 | 0.53 | 1.27 |
| 809.5937 | 1101 | 1.58E−05 | 3.5 | 0.38 | 2.92 | 0.46 | 1.2 |
| 810.5401 | 1204 | 0.001 | 3.52 | 0.34 | 3.11 | 0.46 | 1.13 |
| 810.597 | 1101 | 0.0001 | 2.53 | 0.42 | 2.01 | 0.45 | 1.26 |
| 811.5733 | 1202 | 0.0028 | 3.25 | 0.52 | 2.8 | 0.47 | 1.16 |
| 812.5767 | 1202 | 0.0028 | 2.34 | 0.47 | 1.77 | 0.77 | 1.33 |
| 813.5888 | 1202 | 0.0017 | 3.62 | 0.45 | 3.23 | 0.37 | 1.12 |
| 814.592 | 1202 | 0.0008 | 2.65 | 0.39 | 2.26 | 0.36 | 1.17 |
| 816.5591 | 1102 | 3.10E−06 | 2.26 | 0.35 | 1.6 | 0.51 | 1.41 |
| 816.7297 | 1204 | 0.0444 | 0.25 | 0.58 | 0 | 0 | 0.25 |
| 817.5376 | 1102 | 2.59E−07 | 2.42 | 0.39 | 1.6 | 0.55 | 1.51 |
| 819.5553 | 1102 | 0.0001 | 2.2 | 0.64 | 1.32 | 0.78 | 1.67 |
| 821.5718 | 1102 | 2.76E−08 | 3.02 | 0.44 | 2.13 | 0.5 | 1.42 |
| 822.5751 | 1102 | 3.08E−07 | 2.01 | 0.44 | 1.12 | 0.6 | 1.79 |
| 824.689 | 1203 | 0.0032 | 2.33 | 0.77 | 1.53 | 1.01 | 1.52 |
| 825.5545 | 1202 | 0.038 | 3.16 | 0.86 | 2.68 | 0.67 | 1.18 |
| 825.5548 | 1102 | 0.0017 | 1.06 | 0.77 | 0.41 | 0.55 | 2.55 |
| 826.5579 | 1202 | 0.0426 | 2.12 | 0.89 | 1.63 | 0.75 | 1.3 |
| 826.7053 | 1203 | 0.0039 | 4.43 | 0.61 | 3.88 | 0.66 | 1.14 |
| 827.5439 | 1101 | 0.0345 | 1.82 | 1.11 | 1.19 | 0.88 | 1.52 |
| 827.5698 | 1102 | 2.43E−07 | 4.75 | 0.39 | 3.83 | 0.65 | 1.24 |
| 827.5699 | 1202 | 0.0259 | 6.79 | 0.5 | 6.47 | 0.47 | 1.05 |
| 827.7084 | 1203 | 0.0029 | 3.7 | 0.6 | 3.16 | 0.6 | 1.17 |
| 828.5734 | 1102 | 7.16E−08 | 3.72 | 0.37 | 2.87 | 0.55 | 1.3 |
| 828.5741 | 1202 | 0.0258 | 5.69 | 0.45 | 5.4 | 0.43 | 1.05 |
| 828.7206 | 1203 | 0.0268 | 5.58 | 0.56 | 5.22 | 0.56 | 1.07 |
| 829.5597 | 1101 | 0.0052 | 1.89 | 0.84 | 1.19 | 0.83 | 1.59 |
| 829.5857 | 1102 | 2.38E−06 | 4.41 | 0.5 | 3.55 | 0.61 | 1.24 |
| 829.7239 | 1204 | 0.0481 | 2.77 | 0.58 | 2.34 | 0.86 | 1.18 |
| 829.7244 | 1203 | 0.0355 | 4.83 | 0.55 | 4.49 | 0.55 | 1.08 |
| 830.5887 | 1102 | 3.45E−06 | 3.3 | 0.5 | 2.48 | 0.59 | 1.33 |
| 830.6537 | 1102 | 0.0004 | 2.49 | 0.35 | 2.06 | 0.44 | 1.21 |
| 830.7359 | 1203 | 0.0499 | 5.12 | 0.61 | 4.78 | 0.55 | 1.07 |
| 831.575 | 1101 | 0.0001 | 2.87 | 0.49 | 2.31 | 0.43 | 1.24 |
| 831.575 | 1101 | 0.0001 | 2.87 | 0.49 | 2.31 | 0.43 | 1.24 |
| 831.5999 | 1102 | 3.19E−07 | 5.12 | 0.51 | 4.22 | 0.55 | 1.22 |
| 831.6002 | 1202 | 0.0111 | 6.36 | 0.46 | 6.03 | 0.41 | 1.06 |
| 831.7409 | 1203 | 0.0438 | 4.27 | 0.6 | 3.94 | 0.54 | 1.09 |
| 832.5765 | 1101 | 0.0094 | 0.52 | 0.87 | 0.04 | 0.17 | 14.81 |
| 832.6028 | 1102 | 3.72E−07 | 3.98 | 0.51 | 3.1 | 0.53 | 1.28 |
| 832.6039 | 1202 | 0.0119 | 5.26 | 0.45 | 4.95 | 0.4 | 1.06 |
| 835.6996 | 1204 | 0.0102 | 2.81 | 0.99 | 2.01 | 1.09 | 1.4 |
| 836.7063 | 1204 | 0.0067 | 1.87 | 1.13 | 0.98 | 1.06 | 1.9 |
| 837.5884 | 1202 | 0.022 | 2.81 | 0.38 | 2.56 | 0.37 | 1.1 |
| 837.7182 | 1204 | 0.0042 | 3.32 | 0.96 | 2.4 | 1.17 | 1.39 |
| 838.7227 | 1204 | 0.0035 | 2.64 | 1.02 | 1.66 | 1.19 | 1.59 |
| 839.7321 | 1204 | 0.0325 | 1.64 | 1.29 | 0.87 | 1.13 | 1.87 |
| 847.5955 | 1202 | 0.0215 | 2.67 | 0.49 | 2.33 | 0.49 | 1.14 |
| 850.703 | 1203 | 0.0002 | 3.38 | 0.6 | 2.7 | 0.6 | 1.25 |
| 851.5689 | 1102 | 0.0008 | 2.92 | 0.63 | 2.28 | 0.64 | 1.28 |
| 851.7111 | 1203 | 0.0058 | 3.03 | 0.57 | 2.47 | 0.76 | 1.22 |
| 852.5725 | 1102 | 0.0048 | 1.98 | 0.68 | 1.41 | 0.66 | 1.4 |
| 852.7198 | 1203 | 0.0274 | 5.94 | 0.62 | 5.57 | 0.49 | 1.07 |
| 852.7242 | 1204 | 0.0074 | 3.66 | 0.62 | 3.21 | 0.52 | 1.14 |
| 853.5854 | 1102 | 1.66E−05 | 3.01 | 0.48 | 2.33 | 0.51 | 1.29 |
| 853.7252 | 1203 | 0.0376 | 5.25 | 0.62 | 4.91 | 0.49 | 1.07 |
| 854.5887 | 1102 | 0.0004 | 2.03 | 0.46 | 1.43 | 0.62 | 1.42 |
| 855.6013 | 1102 | 9.20E−06 | 4.14 | 0.41 | 3.36 | 0.66 | 1.23 |
| 856.6046 | 1102 | 8.38E−06 | 3.14 | 0.41 | 2.42 | 0.59 | 1.3 |
| 856.6697 | 1102 | 3.72E−07 | 2.99 | 0.34 | 2.28 | 0.49 | 1.31 |
| 857.617 | 1102 | 0.001 | 2.52 | 0.8 | 1.68 | 0.87 | 1.5 |
| 857.6733 | 1102 | 1.09E−06 | 2.14 | 0.33 | 1.34 | 0.64 | 1.6 |
| 858.6847 | 1102 | 2.66E−05 | 3.48 | 0.42 | 2.88 | 0.49 | 1.21 |
| 859.6877 | 1102 | 3.67E−05 | 2.53 | 0.4 | 1.97 | 0.45 | 1.28 |
| 861.5265 | 1102 | 2.01E−06 | 2.38 | 0.43 | 1.63 | 0.54 | 1.46 |

TABLE 1-continued

List of metabolites discriminating prostate cancer-positive from normal serum (p < 0.05).

| Detected Mass | Analysis Mode | P_Value | Avg. Normal (log2) | StDev. Normal | Avg. Prostate (log2) | StDev. Prostate | Normal/Prostate (log2 ratio) |
|---|---|---|---|---|---|---|---|
| 861.7174 | 1204 | 0.0161 | 4.38 | 0.84 | 3.81 | 0.76 | 1.15 |
| 861.7808 | 1203 | 0.0128 | 3.02 | 0.48 | 2.66 | 0.51 | 1.14 |
| 862.7228 | 1204 | 0.0046 | 3.92 | 0.69 | 3.34 | 0.69 | 1.18 |
| 863.6874 | 1204 | 0.001 | 5.36 | 0.4 | 4.83 | 0.63 | 1.11 |
| 863.7339 | 1204 | 0.0071 | 5.83 | 0.67 | 5.27 | 0.72 | 1.11 |
| 864.738 | 1204 | 0.0063 | 5.13 | 0.63 | 4.58 | 0.71 | 1.12 |
| 865.7482 | 1204 | 0.0198 | 5.44 | 0.75 | 4.9 | 0.83 | 1.11 |
| 866.7527 | 1204 | 0.0308 | 4.67 | 0.78 | 4.15 | 0.84 | 1.13 |
| 867.7576 | 1204 | 0.0183 | 3.23 | 0.75 | 2.58 | 1.09 | 1.25 |
| 871.5528 | 1102 | 9.31E−07 | 3.47 | 0.46 | 2.69 | 0.51 | 1.29 |
| 872.5556 | 1102 | 1.76E−05 | 2.41 | 0.44 | 1.74 | 0.54 | 1.39 |
| 873.5684 | 1102 | 8.02E−06 | 2.42 | 0.51 | 1.66 | 0.54 | 1.45 |
| 876.7223 | 1203 | 0.0008 | 4.38 | 0.59 | 3.71 | 0.72 | 1.18 |
| 877.7271 | 1203 | 0.0029 | 3.56 | 0.64 | 2.93 | 0.76 | 1.22 |
| 878.7381 | 1203 | 0.0075 | 6.24 | 0.6 | 5.78 | 0.57 | 1.08 |
| 879.598 | 1102 | 0.0007 | 1.67 | 0.63 | 1.1 | 0.48 | 1.53 |
| 879.742 | 1203 | 0.0083 | 5.51 | 0.59 | 5.04 | 0.59 | 1.09 |
| 880.7528 | 1203 | 0.0122 | 7.31 | 0.66 | 6.88 | 0.46 | 1.06 |
| 880.7555 | 1204 | 0.0202 | 4.51 | 0.74 | 4.07 | 0.5 | 1.11 |
| 881.7568 | 1203 | 0.0137 | 6.55 | 0.65 | 6.15 | 0.43 | 1.07 |
| 881.7609 | 1204 | 0.038 | 4.04 | 0.8 | 3.63 | 0.51 | 1.11 |
| 882.7673 | 1203 | 0.0252 | 7.43 | 0.71 | 7.05 | 0.43 | 1.06 |
| 882.7717 | 1204 | 0.0429 | 4.99 | 0.81 | 4.59 | 0.51 | 1.09 |
| 883.7715 | 1203 | 0.0273 | 6.57 | 0.69 | 6.2 | 0.41 | 1.06 |
| 884.7817 | 1203 | 0.0156 | 6.5 | 0.7 | 6.08 | 0.44 | 1.07 |
| 884.7873 | 1204 | 0.0252 | 4.76 | 0.76 | 4.33 | 0.51 | 1.1 |
| 885.7867 | 1203 | 0.0153 | 5.49 | 0.66 | 5.09 | 0.44 | 1.08 |
| 885.7919 | 1204 | 0.0131 | 4.05 | 0.73 | 3.59 | 0.5 | 1.13 |
| 886.5582 | 1102 | 3.88E−07 | 3.51 | 0.32 | 2.75 | 0.55 | 1.28 |
| 886.8027 | 1204 | 0.0165 | 3.49 | 0.71 | 3.05 | 0.51 | 1.14 |
| 887.5625 | 1102 | 3.90E−05 | 2.6 | 0.37 | 1.89 | 0.67 | 1.37 |
| 887.8022 | 1203 | 0.0251 | 3.28 | 0.86 | 2.81 | 0.48 | 1.17 |
| 893.774 | 1204 | 0.0192 | 5.83 | 0.8 | 5.31 | 0.69 | 1.1 |
| 894.7273 | 1204 | 0.001 | 4.24 | 0.65 | 3.6 | 0.63 | 1.18 |
| 894.7813 | 1204 | 0.0049 | 4.39 | 0.74 | 3.78 | 0.7 | 1.16 |
| 895.5578 | 1102 | 2.28E−08 | 2.61 | 0.38 | 1.77 | 0.5 | 1.48 |
| 895.559 | 1202 | 0.0235 | 2.34 | 0.41 | 1.99 | 0.61 | 1.17 |
| 895.7335 | 1204 | 0.0024 | 3.82 | 0.67 | 3.22 | 0.62 | 1.18 |
| 895.7873 | 1204 | 0.0115 | 2.68 | 1.32 | 1.65 | 1.4 | 1.62 |
| 896.745 | 1204 | 0.0031 | 4.26 | 0.69 | 3.69 | 0.59 | 1.15 |
| 897.573 | 1102 | 8.61E−06 | 2.28 | 0.49 | 1.45 | 0.66 | 1.57 |
| 897.75 | 1204 | 0.0053 | 3.68 | 0.76 | 3.13 | 0.54 | 1.18 |
| 898.7605 | 1204 | 0.0026 | 3.79 | 0.69 | 3.22 | 0.54 | 1.17 |
| 899.5871 | 1102 | 6.42E−07 | 2.93 | 0.5 | 2.07 | 0.54 | 1.41 |
| 899.7663 | 1204 | 0.0179 | 3.04 | 0.83 | 2.55 | 0.53 | 1.19 |
| 900.5897 | 1102 | 2.46E−07 | 1.94 | 0.46 | 0.98 | 0.65 | 1.98 |
| 902.737 | 1203 | 0.0022 | 4.31 | 0.67 | 3.71 | 0.61 | 1.16 |
| 903.7407 | 1203 | 0.001 | 3.66 | 0.65 | 2.99 | 0.68 | 1.22 |
| 904.7535 | 1203 | 0.0012 | 5.52 | 0.54 | 5.02 | 0.48 | 1.1 |
| 905.7573 | 1203 | 0.0013 | 4.79 | 0.52 | 4.31 | 0.45 | 1.11 |
| 906.769 | 1203 | 0.0016 | 5.87 | 0.48 | 5.46 | 0.39 | 1.08 |
| 907.7735 | 1203 | 0.0011 | 5.13 | 0.47 | 4.72 | 0.36 | 1.09 |
| 907.7735 | 1203 | 0.0011 | 5.13 | 0.47 | 4.72 | 0.36 | 1.09 |
| 908.708 | 1204 | 0.0018 | 3.13 | 0.65 | 2.43 | 0.84 | 1.29 |
| 908.7842 | 1204 | 0.0092 | 2.68 | 0.88 | 1.92 | 1.09 | 1.4 |
| 908.7843 | 1203 | 0.0011 | 5.24 | 0.5 | 4.78 | 0.41 | 1.1 |
| 909.7153 | 1204 | 0.0151 | 3.2 | 0.89 | 2.64 | 0.65 | 1.21 |
| 909.7892 | 1203 | 0.0011 | 4.42 | 0.48 | 3.99 | 0.39 | 1.11 |
| 910.7248 | 1204 | 0.0047 | 3.77 | 0.73 | 3.2 | 0.6 | 1.18 |
| 910.7979 | 1203 | 0.0001 | 3.71 | 0.49 | 3.12 | 0.48 | 1.19 |
| 911.7326 | 1204 | 0.0069 | 4.17 | 0.82 | 3.57 | 0.68 | 1.17 |
| 912.7412 | 1204 | 0.0105 | 4.25 | 0.82 | 3.69 | 0.63 | 1.15 |
| 913.7502 | 1204 | 0.0143 | 5.1 | 0.98 | 4.49 | 0.67 | 1.14 |
| 914.7577 | 1204 | 0.026 | 4.9 | 1.01 | 4.33 | 0.67 | 1.13 |
| 915.7673 | 1204 | 0.0297 | 6.06 | 1.07 | 5.48 | 0.68 | 1.11 |
| 916.774 | 1204 | 0.0399 | 5.76 | 1.03 | 5.23 | 0.67 | 1.1 |
| 917.7836 | 1204 | 0.0157 | 6.41 | 1.05 | 5.76 | 0.72 | 1.11 |
| 918.7901 | 1204 | 0.0164 | 5.96 | 1 | 5.34 | 0.7 | 1.12 |
| 919.7981 | 1204 | 0.0053 | 5.38 | 0.96 | 4.66 | 0.75 | 1.15 |
| 920.747 | 1204 | 0.0002 | 4.08 | 0.58 | 3.43 | 0.58 | 1.19 |
| 920.8054 | 1204 | 0.0012 | 4.46 | 0.91 | 3.61 | 0.81 | 1.23 |
| 921.753 | 1204 | 0.0011 | 3.84 | 0.6 | 3.13 | 0.83 | 1.23 |
| 921.8145 | 1204 | 0.0021 | 3.27 | 1.23 | 2.07 | 1.37 | 1.58 |
| 922.7656 | 1204 | 0.0003 | 3.9 | 0.61 | 3.24 | 0.55 | 1.2 |

TABLE 1-continued

List of metabolites discriminating prostate cancer-positive from normal serum ($p < 0.05$).

| Detected Mass | Analysis Mode | P_Value | Avg. Normal (log2) | StDev. Normal | Avg. Prostate (log2) | StDev. Prostate | Normal/Prostate (log2 ratio) |
|---|---|---|---|---|---|---|---|
| 922.8229 | 1204 | 0.0198 | 2.13 | 1.57 | 1.14 | 1.3 | 1.88 |
| 923.5884 | 1102 | 4.49E−06 | 1.95 | 0.42 | 1.19 | 0.59 | 1.63 |
| 923.7675 | 1204 | 0.0248 | 3.35 | 0.87 | 2.8 | 0.78 | 1.2 |
| 924.7826 | 1204 | 0.0003 | 3.34 | 0.59 | 2.69 | 0.58 | 1.24 |
| 926.7371 | 1203 | 0.0003 | 2.14 | 0.97 | 1 | 1.06 | 2.14 |
| 928.7519 | 1203 | 0.0006 | 3.02 | 0.66 | 2.31 | 0.69 | 1.31 |
| 930.7673 | 1203 | 0.001 | 3.37 | 0.67 | 2.58 | 0.89 | 1.31 |
| 931.7691 | 1203 | 0.046 | 2.31 | 1.18 | 1.64 | 1.11 | 1.41 |
| 931.793 | 1204 | 0.016 | 2.05 | 1.41 | 1.09 | 1.26 | 1.87 |
| 932.7819 | 1203 | 0.026 | 3.25 | 0.79 | 2.81 | 0.49 | 1.15 |
| 934.7235 | 1204 | 0.0092 | 3.33 | 0.88 | 2.6 | 1.01 | 1.28 |
| 935.7299 | 1204 | 0.0026 | 3.23 | 0.59 | 2.6 | 0.79 | 1.24 |
| 936.7387 | 1204 | 0.0015 | 3.41 | 0.59 | 2.73 | 0.82 | 1.25 |
| 937.7457 | 1204 | 0.0005 | 3.43 | 0.61 | 2.55 | 1 | 1.34 |
| 938.7553 | 1204 | 0.0011 | 3.6 | 0.69 | 2.75 | 1.01 | 1.31 |
| 939.7616 | 1204 | 0.0016 | 3.39 | 0.73 | 2.63 | 0.84 | 1.29 |
| 940.7709 | 1204 | 0.0005 | 3.65 | 0.81 | 2.73 | 0.92 | 1.34 |
| 941.7779 | 1204 | 0.0016 | 3.31 | 0.96 | 2.37 | 0.99 | 1.39 |
| 942.7876 | 1204 | 0.0093 | 3.5 | 1.1 | 2.72 | 0.89 | 1.29 |
| 943.7931 | 1204 | 0.0099 | 2.93 | 1.31 | 1.96 | 1.2 | 1.49 |
| 944.8033 | 1204 | 0.0124 | 2.95 | 1.35 | 1.96 | 1.3 | 1.5 |
| 945.8085 | 1204 | 0.0019 | 2.54 | 1.35 | 1.26 | 1.38 | 2.01 |
| 946.8187 | 1204 | 0.0246 | 1.89 | 1.53 | 0.98 | 1.21 | 1.94 |
| 950.7385 | 1203 | 0.0482 | 0.54 | 0.93 | 0.12 | 0.4 | 4.58 |
| 952.7568 | 1203 | 0.0004 | 0.91 | 1.05 | 0.06 | 0.3 | 14.68 |
| 952.7759 | 1204 | 0.0034 | 2.34 | 1.05 | 1.37 | 1.16 | 1.71 |
| 954.7905 | 1204 | 0.0344 | 1.44 | 1.25 | 0.75 | 0.95 | 1.92 |
| 962.7616 | 1204 | 0.0031 | 2.2 | 1.09 | 1.19 | 1.17 | 1.85 |
| 964.7764 | 1204 | 0.0017 | 2.64 | 0.79 | 1.82 | 0.93 | 1.45 |
| 965.7839 | 1204 | 0.0037 | 1.95 | 1.07 | 1.01 | 1.08 | 1.93 |
| 966.7933 | 1204 | 0.0047 | 2.48 | 0.95 | 1.63 | 1.07 | 1.53 |
| 967.7981 | 1204 | 0.0022 | 1.91 | 0.94 | 0.99 | 1.05 | 1.93 |
| 968.8072 | 1204 | 0.001 | 1.83 | 0.91 | 0.84 | 1.05 | 2.17 |
| 997.3968 | 1102 | 0.0011 | 2.15 | 0.22 | 2.39 | 0.25 | 0.9 |
| 1016.929 | 1203 | 6.70E−06 | 4.91 | 0.63 | 3.87 | 0.8 | 1.27 |
| 1017.934 | 1203 | 3.45E−05 | 4.56 | 0.65 | 3.43 | 1.04 | 1.33 |
| 1018.943 | 1203 | 3.17E−05 | 4.22 | 0.7 | 3.11 | 0.96 | 1.35 |
| 1019.95 | 1203 | 9.64E−06 | 3.37 | 0.7 | 2.07 | 1.1 | 1.63 |
| 1040.934 | 1203 | 0.0011 | 2.27 | 1.16 | 1.13 | 1.12 | 2 |
| 1176.777 | 1204 | 0.0452 | 4.32 | 1.09 | 4.92 | 0.96 | 0.88 |
| 1225.093 | 1203 | 0.0048 | 3.34 | 0.82 | 2.59 | 0.96 | 1.29 |
| 1226.098 | 1203 | 0.0077 | 3.11 | 0.94 | 2.49 | 0.55 | 1.25 |
| 1227.107 | 1203 | 0.0202 | 3.47 | 0.95 | 2.81 | 0.98 | 1.23 |
| 1228.113 | 1203 | 0.0104 | 3.07 | 0.88 | 2.5 | 0.59 | 1.23 |
| 1229.118 | 1203 | 0.0018 | 2.11 | 0.93 | 1.12 | 1.16 | 1.89 |
| 1251.115 | 1203 | 0.0026 | 1.62 | 1.24 | 0.62 | 0.93 | 2.6 |
| 1253.129 | 1203 | 0.0043 | 1.91 | 1.21 | 0.96 | 0.99 | 2 |
| 1373.744 | 1201 | 0.0039 | 0.2 | 0.55 | 0.89 | 0.98 | 0.22 |

TABLE 2

Accurate masses, putative molecular formulae and proposed structures for the seven prostate cancer biomarkers detected in aqueous extracts (positive chemical ionization) of human serum.

| Metabolite ID | Detected Mass | Exact Mass | Formula | Proposed Structure |
|---|---|---|---|---|
| 1 | 495.3328 | 495.3325 | $C_{24}H_{50}NO_7P$ | 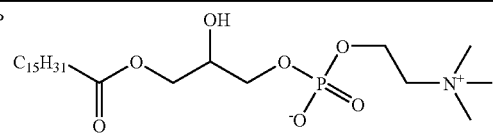 |
| 2 | 517.3147 | 517.3168 | $C_{26}H_{48}NO_7P$ | 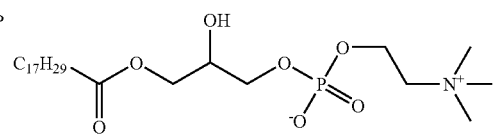 |

TABLE 2-continued

Accurate masses, putative molecular formulae and proposed structures for the seven prostrate cancer biomarkers detected in aqueous extracts (positive chemical ionization) of human serum.

| Metabolite ID | Detected Mass | Exact Mass | Formula | Proposed Structure |
|---|---|---|---|---|
| 3 | 519.3328 | 519.3325 | $C_{26}H_{50}NO_7P$ | 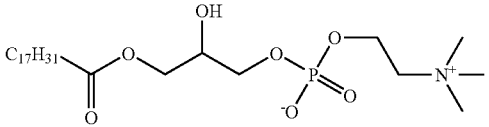 |
| 4 | 521.3481 | 521.3481 | $C_{26}H_{52}NO_7P$ | 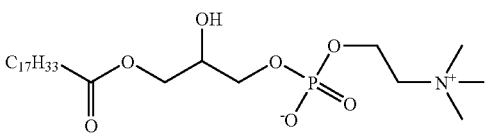 |
| 5 | 523.3640 | 523.3638 | $C_{26}H_{54}NO_7P$ | 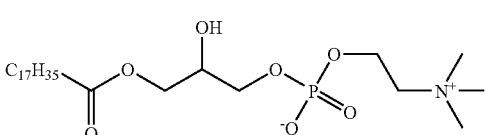 |
| 6 | 541.3148 | 541.3168 | $C_{28}H_{48}NO_7P$ | 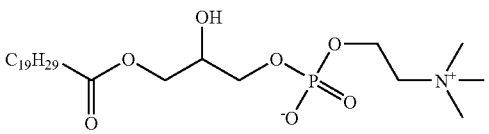 |
| 7 | 545.3460 | 545.3481 | $C_{28}H_{52}NO_7P$ | 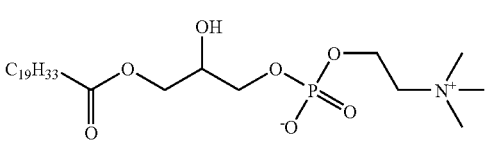 |

TABLE 3

MS/MS fragmentation of prostate cancer biomarker 495.3328, $C_{24}H_{50}NO_7P$ (m/z represents the $[M + H]^+$ mass)

| m/z | Formula | Molecular fragment | Fragment loss |
|---|---|---|---|
| 496 | $C_{24}H_{51}NO_7P^+$ | 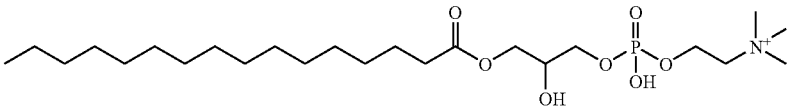 [SMILES: CCCCCCCCCCCCCCCC(=O)OCC(O)COP(=O)(O)OCC[N+](C)(C)C] | |
| 478 | $C_{24}H_{49}NO_6P^+$ | 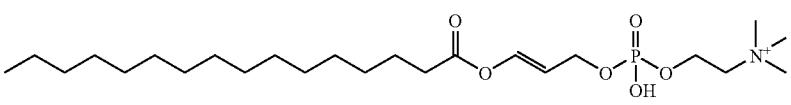 [SMILES: CCCCCCCCCCCCCCCC(=O)O/C=C/COP(=O)(O)OCC[N+](C)(C)C] | 496-$H_2O$ |
| 419 | $C_{21}H_{40}NO_6P^+$ | 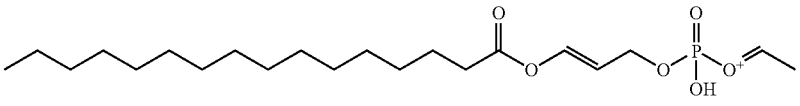 [SMILES: C/C=[O+]/P(=O)(O)OC/C=C/OC(=O)CCCCCCCCCCCCCCC] | 478-$^+HN(CH_3)_3$ |
| 313 | $C_{19}H_{37}O_3^+$ | 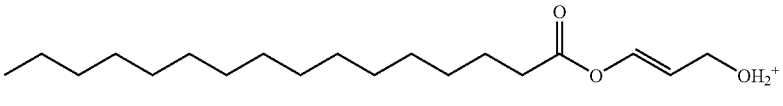 [SMILES: CCCCCCCCCCCCCCCC(=O)O/C=C/C[OH2+]] | 478-166 + $H^+$ |
| 283 | $C_{17}H_{31}O_3^+$ | 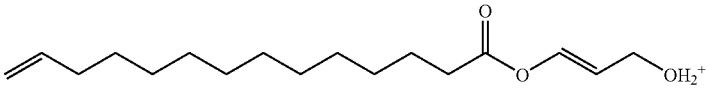 [SMILES: C=CCCCCCCCCCCCC(=O)O/C=C/C[OH2+]] | 313-$C_2H_6$ |

TABLE 3-continued

MS/MS fragmentation of prostate cancer biomarker 495.3328,
$C_{24}H_{50}NO_7P$ (m/z represents the [M + H]$^+$ mass)

| m/z | Formula | Molecular fragment | Fragment loss |
|---|---|---|---|
| 258 | $C_8H_{21}NO_7P^+$ | 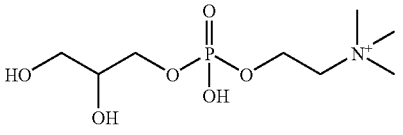 | 496-$C_{16}H_{30}O$ |
| 239 | $C_{16}H_{31}O$ | 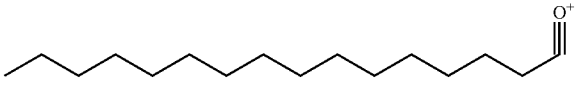 [SMILES: CCCCCCCCCCCCCCCC#[O+]] | 496-$C_8H_{20}NO_5P$ |
| 184 | $C_5H_{15}NO_4P^+$ | 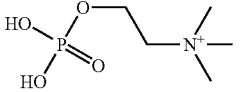 | 258-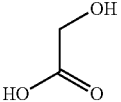 |
| 166 | $C_5H_{13}NO_3P^+$ | 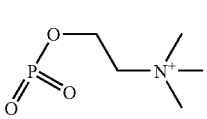 | 478-313 |
| 104 | $C_5H_{14}NO$ | 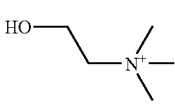 | 184-$HPO_3$ |
| 86 | $C_5H_{12}N$ | 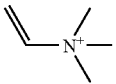 | 104-$H_2O$ |

TABLE 4

MS/MS fragmentation of prostate cancer biomarker 517.3147,
$C_{26}H_{48}NO_7P$ (m/z represents the [M + H]$^+$ mass)

| m/z | Formula | Molecular fragment | Fragment loss |
|---|---|---|---|
| 518 | $C_{26}H_{49}NO_7P^+$ | 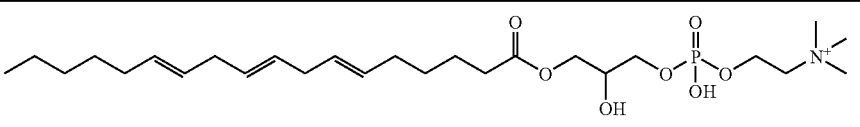 | |
| 459 | $C_{23}H_{40}NO_7P^+$ | 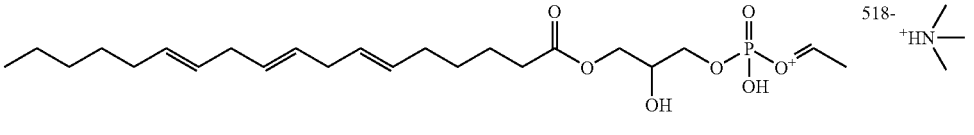 | 518-<br>$^+HN(CH_3)_3$ |
| 415 | $C_{21}H_{36}O_6P^+$ | 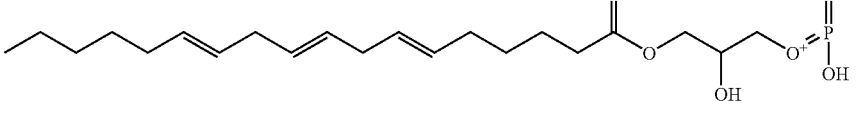 | 459-$C_2H_4O$ |
| 359 | $C_{17}H_{28}O_6P^+$ | 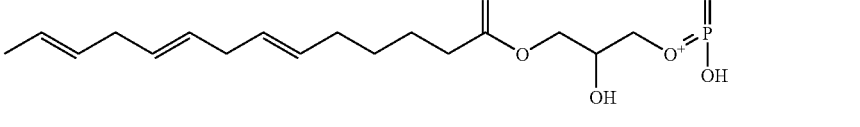 | 415-$C_4H_8$ |
| 341 | $C_{17}H_{26}O_5P^+$ | 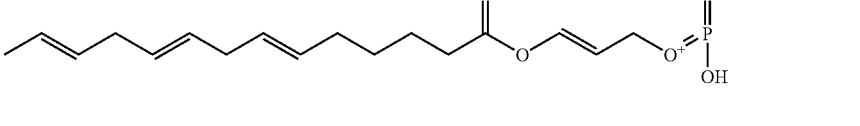 | 359-$H_2O$ |

TABLE 4-continued

MS/MS fragmentation of prostate cancer biomarker 517.3147,
$C_{26}H_{48}NO_7P$ (m/z represents the [M + H]$^+$ mass)

| m/z | Formula | Molecular fragment | Fragment loss |
|---|---|---|---|
| 281 | $C_{10}H_{18}NO_7P^+$ | 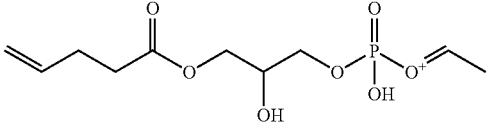 [SMILES: C=CCCC(=O)OCC(O)COP(=O)(O)/[O+]=C/C] | 459-$C_{13}H_{22}$ |
| 221 | $C_8H_{14}NO_5P^+$ | 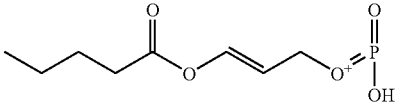 | 359-$C_9H_{14}$ |
| 104 | $C_5H_{14}NO$ | 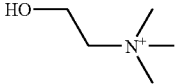 | |
| 86 | $C_5H_{12}N$ |  | 104-$H_2O$ |

TABLE 5

MS/MS fragmentation of prostate cancer biomarker 519.3328,
$C_{26}H_{52}NO_7P$ (m/z represents the [M + H]$^+$ mass)

| m/z | Formula | Molecular fragment |
|---|---|---|
| 520 | $C_{26}H_{51}NO_7P^+$ | 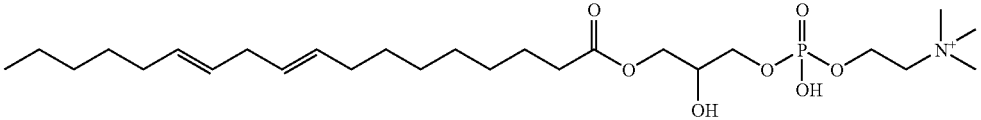 [SMILES: CCCCC/C=C/C/C=C/CCCCCCCC(=O)OCC(O)COP(=O)(O)OCC[N+](C)(C)C] |
| 502 | $C_{26}H_{49}NO_6P^+$ | 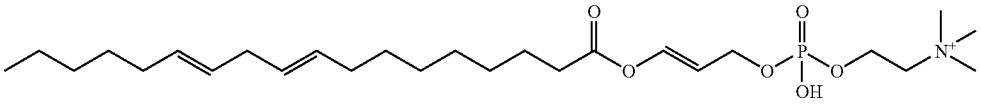 [SMILES: CCCCC/C=C/C/C=C/CCCCCCCC(=O)O/C=C/COP(=O)(O)OCC[N+](C)(C)C] |
| 461 | $C_{23}H_{42}NO_7P^+$ | 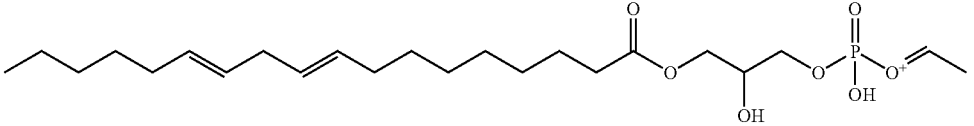 [SMILES: C/C=[O+]/P(=O)(O)OCC(O)COC(=O)CCCCCCC/C=C/C/C=C/CCCCC] |
| 445 | $C_{22}H_{38}NO_7P^+$ | 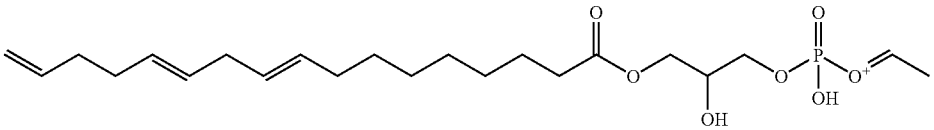 [SMILES: C=CCC/C=C/C/C=C/CCCCCCCC(=O)OCC(O)COP(=O)(O)/[O+]=C/C] |
| 281 | $C_{18}H_{33}O_2$ | 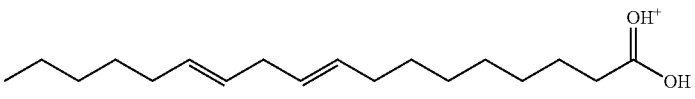 [SMILES: CCCCC/C=C/C/C=C/CCCCCCCC(O)=[OH+]] |
| 221 | $C_{16}H_{29}$ | 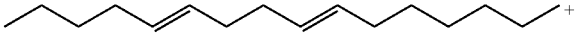 |
| 184 | $C_5H_{15}NO_4P^+$ | 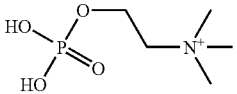 |

TABLE 5-continued

| | | Molecular fragment | |
|---|---|---|---|
| 166 | $C_5H_{13}NO_3P^+$ | phosphocholine structure | |
| 124 | $C_2H_6O_4P^+$ | (HO)$_2$P(=O)–O–CH=CH$_2$ (protonated) | |
| 86 | $C_5H_{12}N$ | CH$_2$=CH–N$^+$(CH$_3$)$_3$ | |

| m/z | Fragment loss |
|---|---|
| 520 | |
| 502 | 520-H$_2$O |
| 461 | 520- $^+$HN(CH$_3$)$_2$ |
| 445 | 461-CH$_4$ |
| 281 | 520-C$_8$H$_{20}$NO$_5$P |
| 221 | 520- (acetyl-glycero-phosphocholine fragment) |
| 184 | |
| 166 | 184-H$_2$O |
| 124 | 184- $^+$HN(CH$_3$)$_2$ |
| 86 | 166-H$_3$PO$_4$ |

TABLE 6

MS/MS fragmentation of prostate cancer biomarker 521.3481, $C_{26}H_{53}NO_7P^+$ (m/z represents the [M + H]$^+$ mass)

| m/z | Formula | Molecular fragment | Fragment loss |
|---|---|---|---|
| 522 | $C_{26}H_{53}NO_7P^+$ | monounsaturated acyl-glycero-phosphocholine | |
| 504 | $C_{26}H_{51}NO_6P^+$ | dehydrated acyl-enol-glycero-phosphocholine | 522-H$_2$O |
| 478 | $C_{23}H_{45}NO_7P^+$ | diunsaturated acyl-glycero-phosphocholine | 522-C$_3$H$_8$ |
| 357 | $C_{18}H_{30}NO_5P^+$ | diunsaturated acyl-enol-phosphate | 478-(i) O=CH–CH$_2$–N$^+$(CH$_3$)$_3$; (ii) H$_2$O |

TABLE 6-continued

MS/MS fragmentation of prostate cancer biomarker 521.3481,
$C_{26}H_{53}NO_7P^+$ (m/z represents the [M + H]$^+$ mass)

| m/z | Formula | Molecular fragment | Fragment loss |
|---|---|---|---|
| 258 | $C_8H_{21}NO_6P^+$ | | $C_{18}H_{33}O^+$ |
| 221 | $C_{15}H_{25}O^+$ | | $C_{18}H_{33}O^+$-$C_3H_8$ |
| 184 | $C_5H_{15}NO_4P^+$ | | 522-$C_{21}H_{38}O_3$ |
| 124 | $C_2H_6H_4P^+$ | | 184- (trimethylamine) |
| 104 | $C_5H_{14}NO$ | | 184-$HPO_3$ |
| 86 | $C_5H_{12}N$ | | 104-$H_2O$ |

TABLE 7

MS/MS fragmentation of prostate cancer biomarker 523.3640,
$C_{26}H_{55}NO_7P^+$ (m/z represents the [M + H]$^+$ mass)

| m/z | Formula | Molecular fragment | Fragment loss |
|---|---|---|---|
| 524 | $C_{26}H_{55}NO_7P^+$ | | |
| 506 | $C_{26}H_{53}NO_6P^+$ | | 524-$H_2O$ |
| 496 | $C_{24}H_{51}NO_7P^+$ | | 524-$C_2H_4$ |
| 478 | $C_{24}H_{49}NO_6P^+$ | | 496-$H_2O$ |
| 331 | $C_{19}H_{39}O_4^+$ | | 496-166 + H$^+$ |

TABLE 7-continued

MS/MS fragmentation of prostate cancer biomarker 523.3640,
$C_{26}H_{55}NO_7P^+$ (m/z represents the [M + H]$^+$ mass)

| m/z | Formula | Molecular fragment | Fragment loss |
|---|---|---|---|
| 313 | $C_{19}H_{37}O_3^+$ | | 496- |
| 258 | $C_8H_{21}NO_6P^+$ | | 524-$C_{18}H_{34}O$ |
| 285 | $C_{18}H_{37}O_3^+$ | | 524-$C_8H_{20}NO_5P$ |
| 184 | $C_5H_{15}NO_4P^+$ | | 524-313 |
| 166 | $C_5H_{13}NO_3P^+$ | | 184-$H_2O$ |
| 124 | $C_2H_6O_4P^+$ | | 184- |
| 104 | $C_5H_{14}NO$ | | 184-$HPO_3$ |
| 86 | $C_5H_{12}N$ | | 104-$H_2O$ |

TABLE 8

MS/MS fragmentation of prostate cancer biomarker 541.3148,
$C_{28}H_{49}NO_7P^+$ (m/z represents the [M + H]$^+$ mass)

| m/z | Formula | Molecular fragment | Fragment loss |
|---|---|---|---|
| 542 | $C_{28}H_{49}NO_7P^+$ | | |
| 483 | $C_{25}H_{40}NO_7P^+$ | | 542- |
| 284 | $C_9H_{19}NO_7P^+$ | | 542-$C_{19}H_{30}$ |

TABLE 8-continued

MS/MS fragmentation of prostate cancer biomarker 541.3148,
$C_{28}49_5NO_7P^+$ (m/z represents the $[M + H]^+$ mass)

| m/z | Formula | Molecular fragment | Fragment loss |
|---|---|---|---|
| 225 | $C_6H_{10}NO_7P^+$ | | 483-$C_{19}H_{30}$ |
| 184 | $C_5H_{15}NO_4P^+$ | | 542-$C_{23}H_{34}O_3$ |
| 104 | $C_5H_{14}NO$ | | 184-$HPO_3$ |
| 86 | $C_5H_{12}N$ | | 104-$H_2O$ |

TABLE 9

MS/MS fragmentation of prostate cancer biomarker 545.3460,
$C_{28}H_{53}NO_7P^+$ (m/z represents the $[M + H]^+$ mass)

| m/z | Formula | Molecular fragment | Fragment loss |
|---|---|---|---|
| 546 | $C_{28}H_{53}NO_7P^+$ | | |
| 528 | $C_{28}H_{51}NO_6P^+$ | | 546-$H_2O$ |
| 514 | $C_{27}H_{49}NO_6P^+$ | | 528-$CH_3$ |
| 487 | $C_{25}H_{44}NO_7P^+$ | | 546- |
| 104 | $C_5H_{14}NO$ | | |
| 86 | $C_5H_{12}N$ | | 104-$H_2O$ |

TABLE 10

Comparison of fragment ion patterns for 2-Hydroxy-1-palmitoyl-sn-glycero-3-phosphocholine and 495.3328.

| Fragment Ion [M + H] | Standard % | 495.3328 % |
|---|---|---|
| 496 | 100 | 90 |
| 478 | 1 | 5 |
| 419 | 1 | 1 |
| 313 | 10 | 1 |
| 239 | 1 | 1 |
| 258 | 1 | 1 |
| 184 | 80 | 90 |
| 166 | 1 | 1 |
| 104 | 30 | 100 |
| 86 | 1 | 70 |

TABLE 11

Accurate masses, putative molecular formulae and proposed structures for the seven prostrate cancer biomarkers detected in aqueous extracts (negative electrospray ionization) of human serum.

| Detected Mass | Calculated Mass | Formula | Proposed Structure |
|---|---|---|---|
| 481.317 | 481.3168 | $C_{23}H_{48}NO_7P$ | |
| 531.3123 | 531.3114 | $C_{30}H_{46}NO_5P$ | |
| 541.3422 | 541.3380 | $C_{25}H_{52}NO_9P$ | |
| 555.3101 | 555.3172 | $C_{25}H_{50}NO_{10}P$ | |
| 565.3394 | 565.3380 | $C_{27}H_{52}NO_9P$ | |
| 567.3546 | 567.3536 | $C_{27}H_{54}NO_9P$ | |

TABLE 11-continued

Accurate masses, putative molecular formulae and proposed structures for the seven prostrate cancer biomarkers detected in aqueous extracts (negative electrospray ionization) of human serum.

| Detected Mass | Calculated Mass | Formula | Proposed Structure |
|---|---|---|---|
| 569.3687 | 569.3693 | $C_{27}H_{56}NO_9P$ | 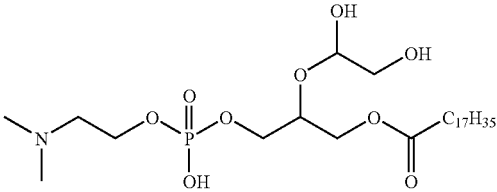 |

TABLE 12

MS/MS fragmentation of prostate cancer biomarker 481.3171, $C_{23}H_{48}NO_7P$ (m/z represents the [M − H]⁻ mass)

| m/z | Formula | Molecular fragment | Fragment loss |
|---|---|---|---|
| 480 | $C_{23}H_{47}NO_7P$ | 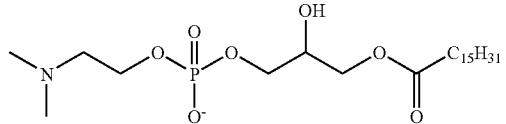 | —H⁺ |
| 462 | $C_{23}H_{45}NO_6P$ | 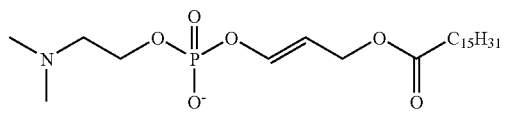 | —H₂O |
| 435 | $C_{21}H_{40}O_7P$ | 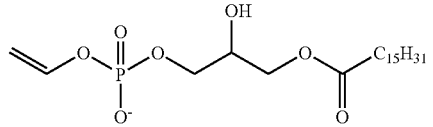 | 480-NH(CH₃)₂ |
| 391 | $C_{19}H_{36}NO_6P$ | 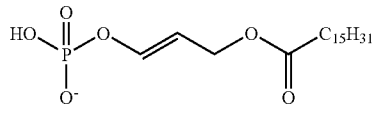 | 462- 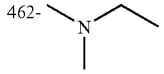 |
| 255 | $C_{16}H_{31}O_2$ | 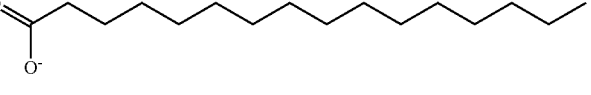 | 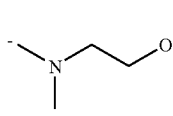 |
| 242 | $C_6H_{13}NO_7P$ | 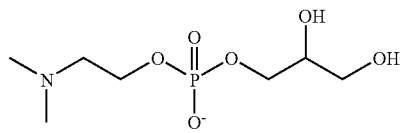 | -O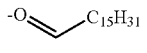$C_{15}H_{31}$ |
| 224 | $C_6H_{11}NO_6P$ | 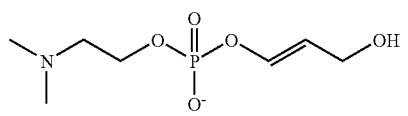 | 242-H₂O |
| 168 | $C_4H_{11}NO_4P$ | 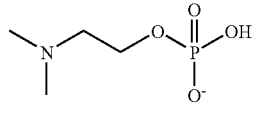 | 224- 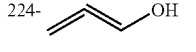 |

TABLE 12-continued

MS/MS fragmentation of prostate cancer biomarker 481.3171,
$C_{23}H_{48}NO_7P$ (m/z represents the [M − H]⁻ mass)

| m/z | Formula | Molecular fragment | Fragment loss |
|---|---|---|---|
| 153 | $C_3H_6O_5P$ | (HO)(O⁻)P(=O)−O−CH=CH−CH₂−OH | 224- N(CH₃)(C₂H₅) |
| 79 | $PO_3$ | O=P(=O)−O⁻ | |

TABLE 13

MS/MS fragmentation of prostate cancer biomarker 531.3123,
$C_{30}H_{46}NO_5P$ (m/z represents the [M − H]⁻ mass)

| m/z | Formula |
|---|---|
| 530 | $C_{30}H_{45}NO_5P$ |
| 480 | |
| 255 | |
| 224 | |
| 168 | |
| 78 | |

TABLE 14

MS/MS fragmentation of prostate cancer biomarker 541.3380,
$C_{25}H_{52}NO_9P$ (m/z represents the [M − H]⁻ mass)

| m/z | Formula | Molecular fragment | Fragment loss |
|---|---|---|---|
| 540 | $C_{25}H_{51}NO_9P$ | [dimethylaminoethyl phosphate − glyceryl − (2-O-glyceryl) − O-C(=O)C₁₅H₃₁] | —H⁺ |
| 480 | $C_{23}H_{47}NO_7P$ | [dimethylaminoethyl phosphate − glyceryl(OH) − O-C(=O)C₁₅H₃₁] | -OH, HO-CH=CH- |
| 255 | $C_{16}H_{31}O_2$ | ⁻O−C(=O)−C₁₅H₃₁ | 480- [dimethylaminoethyl phosphate − CH₂CH(OH)CH₃] |
| 242 | $C_7H_{17}NO_6P$ | [dimethylaminoethyl phosphate − glyceryl(OH)(OH)] | 480- C₁₅H₃₁−CH=O |
| 224 | $C_7H_{15}NO_5P$ | [dimethylaminoethyl phosphate − O−CH=CH−OH] | 242-$H_2O$ |

TABLE 14-continued

MS/MS fragmentation of prostate cancer biomarker 541.3380,
C$_{25}$H$_{52}$NO$_9$P (m/z represents the [M – H]$^-$ mass)

| m/z | Formula | Molecular fragment | Fragment loss |
|---|---|---|---|
| 168 | C$_4$H$_{11}$NO$_4$P | 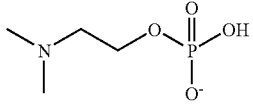 | 224- 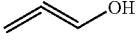 |
| 153 | C$_3$H$_6$O$_5$P | 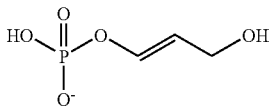 | 224-  |
| 79 | PO$_3$ |  | |

TABLE 15

MS/MS fragmentation of prostate cancer biomarker 555.3172,
C$_{26}$H$_{54}$NO$_9$P (m/z represents the [M – H]$^-$ mass)

| m/z | Formula | Molecular fragment | Fragment loss |
|---|---|---|---|
| 554 | C$_{26}$H$_{53}$NO$_9$P | 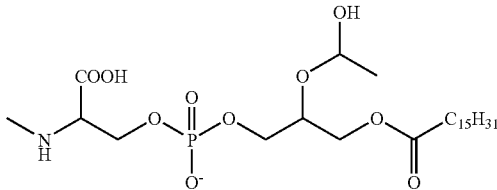 | —H$^+$ |
| 508 | C$_{25}$H$_{52}$NO$_7$P | 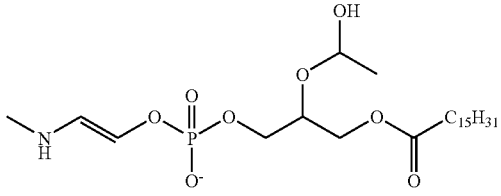 | —HCOOH |
| 494 | C$_{23}$H$_{45}$NO$_8$P | 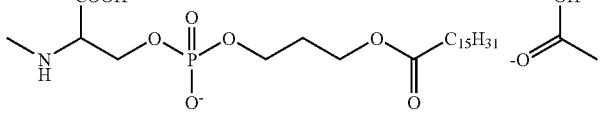 | 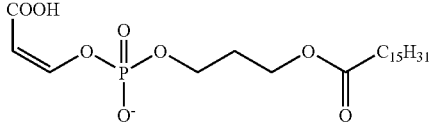 |
| 463 | C$_{22}$H$_{40}$O$_8$P | 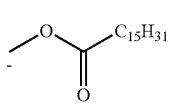 | 494-CH$_3$NH$_2$ |
| 281 | | | |
| 269 | C$_{17}$H$_{32}$O$_2$ | 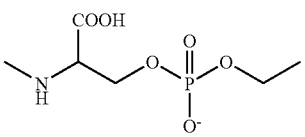 | 494- |
| 242 | C$_7$H$_{17}$NO$_6$P | | |

TABLE 15-continued

MS/MS fragmentation of prostate cancer biomarker 555.3172,
$C_{26}H_{54}NO_9P$ (m/z represents the [M – H]$^-$ mass)

| m/z | Formula | Molecular fragment | Fragment loss |
|---|---|---|---|
| 224 | $C_6H_{11}NO_6P$ | [structure: methylamino-serine phosphate vinyl ester with COOH] | 480- [structure: methyl ester of $C_{15}H_{31}$ carboxylic acid] |
| 168 | | | |
| 153 | | | |
| 79 | | | |

TABLE 16

MS/MS fragmentation of prostate cancer biomarker 565.3394,
$C_{27}H_{52}NO_9P$ (m/z represents the [M – H]$^-$ mass)

| m/z | Formula | Molecular fragment | Fragment loss |
|---|---|---|---|
| 564 | $C_{27}H_{51}NO_9P$ | [structure: dimethylaminoethyl phosphate glycerol with $C_{17}H_{31}$ ester and diol branch] | —H$^+$ |
| 504 | $C_{25}H_{45}NO_8P$ | [structure: dimethylaminoethyl phosphate glycerol with $C_{17}H_{31}$ ester and OH] | - OH [structure: ene-diol] |
| 454 | $C_{19}H_{37}NO_9P$ | [structure: hydroxymethyl-methylamino ethyl phosphate with terminal alkene fatty acid ester] | 564- [structure: heptenyl chain] |
| 279 | $C_{18}H_{31}O_2$ | [structure: $C_{17}H_{31}$ carboxylate] | 504- [structure: dimethylaminoethyl phosphate propylene glycol] |
| 242 | $C_7H_{17}NO_6P$ | [structure: dimethylaminoethyl phosphate glycerol] | 504- [structure: $C_{17}H_{31}$ aldehyde] |
| 224 | $C_7H_{15}NO_5P$ | [structure: dimethylaminoethyl phosphate allyl alcohol] | 242-H$_2$O |
| 168 | $C_4H_{11}NO_4P$ | [structure: dimethylaminoethyl phosphate] | 224- [structure: allyl alcohol] |

TABLE 16-continued

MS/MS fragmentation of prostate cancer biomarker 565.3394,
$C_{27}H_{52}NO_9P$ (m/z represents the [M − H]$^-$ mass)

| m/z | Formula | Molecular fragment | Fragment loss |
|---|---|---|---|
| 153 | $C_3H_6O_5P$ | (phosphate-O-CH=CH-CH2OH) | 224- (N,N-dimethyl ethylamine) |
| 79 | $PO_3$ | ($PO_3^-$) | |

TABLE 17

MS/MS fragmentation of prostate cancer biomarker 567.3546,
$C_{27}H_{54}NO_9P$ (m/z represents the [M − H]$^-$ mass)

| m/z | Formula | Molecular fragment | Fragment loss |
|---|---|---|---|
| 566 | $C_{27}H_{53}NO_9P$ | (full structure with dimethylamino, phosphate, glycerol-diol, oleoyl $C_{17}H_{33}$) | —H$^+$ |
| 506 | $C_{25}H_{47}NO_8P$ | (structure with dimethylamino, phosphate, glycerol-OH, oleoyl $C_{17}H_{33}$) | — OH-CH=CH-OH |
| 281 | $C_{18}H_{33}O_2$ | ($^-$O-CO-$C_{17}H_{33}$) | 504- (dimethylamino-ethyl phosphate-propan-2-ol) |
| 242 | $C_7H_{17}NO_6P$ | (dimethylamino-ethyl phosphate glycerol) | 504- $C_{17}H_{33}$-CHO |
| 224 | $C_7H_{15}NO_5P$ | (dimethylamino-ethyl phosphate allyl alcohol) | 242-$H_2O$ |
| 168 | $C_4H_{11}NO_4P$ | (dimethylamino-ethyl phosphate-OH) | 224- CH2=CH-CH2OH |
| 153 | $C_3H_6O_5P$ | (HO-phosphate-O-CH=CH-CH2OH) | 224- (N,N-dimethyl ethylamine) |
| 79 | $PO_3$ | ($PO_3^-$) | |

TABLE 18

MS/MS fragmentation of prostate cancer biomarker 569.368,
$C_{27}H_{56}NO_9P$ (m/z represents the $[M - H]^-$ mass)

| m/z | Formula | Molecular fragment | Fragment loss |
|---|---|---|---|
| 568 | $C_{27}H_{35}NO_9P$ | | $—H^+$ |
| 508 | $C_{25}H_{49}NO_8P$ | | - OH |
| 283 | $C_{18}H_{35}O_2$ | | 504- |
| 242 | $C_7H_{17}NO_6P$ | | 504- $C_{17}H_{35}$ |
| 224 | $C_7H_{15}NO_5P$ | | 242-$H_2O$ |
| 168 | $C_4H_{11}NO_4P$ | | 224- |
| 153 | $C_3H_6O_5P$ | | 224- |
| 79 | $PO_3$ | | |

TABLE 19

Comparison of MS/MS fragmentation patterns of 569.3687 to
it's corresponding lysophospholipid ethanolamine counterpart, 2-hydroxy-1-stearyl-sn-
glycero-3-phosphoethanolamine standard.

| Standard | | 569.3687 | |
|---|---|---|---|
| m/z | Molecular fragment | m/z | Molecular fragment |
| | | 568 | where R = 60 D |

TABLE 19-continued

Comparison of MS/MS fragmentation patterns of 569.3687 to it's corresponding lysophospholipid ethanolamine counterpart, 2-hydroxy-1-stearyl-sn-glycero-3-phosphoethanolamine standard.

| Standard | | 569.3687 | |
|---|---|---|---|
| m/z | Molecular fragment | m/z | Molecular fragment |
| 480 | [structure: H2N-CH2CH2-O-P(O)(O-)-O-CH2-CH(OH)-CH2-O-C(O)-C17H35] | 508 (568-60) | [structure: (CH3)2N-CH2CH2-O-P(O)(O-)-O-CH2-CH(OH)-CH2-O-C(O)-C17H35] |
| 283 | [structure: -O-C(O)-C17H35] | 283 | [structure: -O-C(O)-C17H35] |
| 214 | [structure: H2N-CH2CH2-O-P(O)(O-)-O-CH2-CH(OH)-CH2OH] | 242 | [structure: (CH3)2N-CH2CH2-O-P(O)(O-)-O-CH2-CH(OH)-CH2OH] |
| 196 | [structure: H2N-CH2CH2-O-P(O)(O-)-O-CH=CH-CH2OH] | 224 | [structure: (CH3)2N-CH2CH2-O-P(O)(O-)-O-CH=CH-CH2OH] |
| 140 | [structure: H2N-CH2CH2-O-P(O)(O-)-OH] | 168 | [structure: (CH3)2N-CH2CH2-O-P(O)(O-)-OH] |
| 153 | [structure: HO-P(O)(O-)-O-CH=CH-CH2OH] | 153 | [structure: HO-P(O)(O-)-O-CH=CH-CH2OH] |
| 79 | [structure: O=P(O)(O-)=O] | 79 | [structure: O=P(O)(O-)=O] |

TABLE 20

| Parent | Daughter 1 | Daughter 2 | Daughter 3 | Daughter 4 | Daughter 5 |
|---|---|---|---|---|---|
| PESI | | | | | |
| 496.33 | 184.2 | 104.2 | 313.4 | 419.4 | 86.2 |
| 518.31 | 104.2 | 459.4 | 313.4 | 415.5 | 147.1 |
| 520.33 | 184.2 | 104.2 | 337.4 | 166.2 | 86.2 |
| 522.35 | 184.2 | 104.2 | 339.4 | 258.4 | 445.3 |
| 524.36 | 184.2 | 104.2 | 341.4 | 258.2 | 86.2 |
| 542.31 | 104.2 | 483.4 | 337.4 | 439.4 | 359.4 |
| 546.35 | 487.4 | 104.2 | 341.4 | 443.5 | 147.0 |
| IS 609.30 | 195.2 | 397.3 | | | |
| NESI | | | | | |
| 480.32 | 255.4 | 224.2 | 242.2 | 283.4 | 153.0 |
| 530.31 | 480.5 | 255.4 | 305.4 | 326.2 | 484.3 |
| 540.34 | 480.5 | 255.4 | 224.2 | 242.2 | 153.0 |
| 554.31 | 494.5 | 269.4 | 283.4 | 508.2 | 224.2 |
| 564.34 | 504.5 | 279.4 | 224.2 | 242.2 | 415.3 |
| 566.35 | 506.5 | 281.4 | 224.2 | 242.2 | 153.0 |
| 568.37 | 508.5 | 283.4 | 224.2 | 242.2 | 419.5 |
| IS 607.20 | 211.3 | 152.2 | | | |

*Note:
The parent m/z and the 2 daughter MRM transitions used in each method are in bold. Additional daughter transitions listed could also be used in other methods in the future.

What is claimed is:

1. A method for determining prostate cancer, or the risk of prostate cancer in a patient, the method comprising the steps of:

a) analyzing at least one blood sample from said patient by high resolution mass spectrometry to obtain accurate mass intensity data;

b) comparing the accurate mass intensity data to corresponding data obtained from one or more than one reference blood sample to identify an increase or decrease in accurate mass intensity; and c) using said increase or decrease in accurate mass intensity to determine prostate cancer, or the risk of prostate cancer in said patient, wherein the accurate mass intensity is measured, in Daltons, at one or more of the following hydrogen and electron adjusted accurate masses or neutral accurate masses ±5 ppm, wherein the hydrogen and electron adjusted accurate masses or neutral accurate masses at which intensity decreases are: 174.1408, 188.1566, 194.0804, 232.9133, 242.2251, 252.2096, 258.2482, 268.2412, 272.2357, 276.2096, 278.2256, 279.2287, 280.2414, 281.2448, 283.2602, 292.204, 296.2358, 298.2519, 299.2558, 300.2098, 300.2676, 302.2256, 304.2394, 304.241, 305.243, 305.2439, 306.257, 308.2715, 310.2154, 310.2884, 312.2313, 312.304, 314.2464, 320.2358, 326.2262, 327.0326, 329.2426, 329.2445, 330.2568, 340.2977, 342.2198, 368.3437, 369.3474, 371.3538, 392.294, 411.3186, 430.3083, 430.3818, 431.3861, 432.3686, 452.2536, 481.3171, 481.3172, 482.3216, 484.3792, 492.4184, 494.4344, 495.3328, 495.4376, 496.336, 501.2848, 505.3227, 506.3213, 507.3317, 509.3493, 517.3148, 518.3182, 518.4345, 519.332, 519.3328, 520.4502, 521.348, 521.4526, 522.464, 523.364, 523.4678, 524.4725, 529.3167, 531.3123, 534.4645, 538.501, 541.3148, 541.3422, 541.3433, 542.3453, 542.3461, 545.346, 548.4817, 549.4848, 552.4048, 555.3101, 565.3393, 565.3394, 566.3433, 566.3434, 567.3546, 567.3548, 568.3573, 568.3574, 569.3687, 569.3691, 570.3726, 570.4653, 570.4915, 579.5322, 580.5345, 587.3228, 589.3401, 589.3404, 590.343, 590.4597, 596.4794, 599.4932, 601.5077, 604.5441, 605.5469, 609.3242, 612.5004, 615.4797, 622.4973, 623.4918, 623.5003, 624.5134, 625.5078, 625.5163, 626.5109, 626.5285, 627.5204, 627.5306, 628.5236, 628.5426, 629.5453, 630.5582, 632.5752, 635.5246, 641.4915, 646.5709, 647.574, 647.6063, 648.5865, 649.5056, 649.5898, 655.5509, 660.5005, 660.6082, 663.4864, 670.5688, 670.5711, 671.5723, 672.5865, 673.5893, 673.6185, 673.6224, 675.6359, 675.6375, 676.6393, 680.5625, 684.5487, 685.5543, 686.5126, 688.5294, 690.4849, 690.547, 692.5571, 693.611, 695.647, 696.5856, 696.651, 699.5205, 702.5675, 705.6083, 707.6256, 708.6308, 710.4923, 716.4982, 721.6388, 722.6423, 723.5194, 723.5198, 724.5247, 724.5496, 725.5375, 726.5456, 727.5565, 728.562, 729.5724, 731.4913, 732.4938, 733.6425, 735.6555, 736.6584, 737.5354, 738.5449, 741.5307, 742.5354, 743.5469, 744.4942, 745.4972, 746.556, 747.5201, 747.5234, 748.5279, 748.5722, 749.5346, 749.5354, 749.5364, 749.5402, 749.5763, 750.5403, 750.5434, 751.551, 751.5529, 751.5548, 752.5565, 752.5578, 753.5674, 755.4866, 756.4905, 757.5017, 757.5618, 758.5089, 758.5654, 759.516, 759.578, 760.5223, 760.5816, 761.5269, 765.5665, 766.5701, 767.5821, 768.4944, 768.5507, 769.4957, 770.5109, 771.5809, 772.5269, 772.5856, 773.5337, 774.5404, 775.553, 775.5533, 776.5563, 776.6057, 777.5679, 779.5438, 779.5831, 780.5474, 781.5612, 782.5087, 782.5649, 783.5141, 783.578, 784.5235, 784.5813, 785.5295, 785.5936, 786.5404, 786.5967, 787.5447, 793.5387, 794.5126, 794.5424, 795.5555, 796.5292, 798.6776, 803.5436, 803.5685, 804.547, 804.5717, 804.7208, 804.7219, 805.5606, 805.5834, 805.7267, 806.6643, 806.5863, 807.5761, 808.5795, 809.5937, 810.5401, 810.597, 811.5733, 812.5767, 813.5888, 814.592, 816.5591, 816.7297, 817.5376, 819.5553, 821.5718, 822.5751, 824.689, 825.5545, 825.5548, 826.5579, 826.7053, 827.5439, 827.5698, 827.5699, 827.7084, 828.5734, 828.5741, 828.7206, 829.5597, 829.5857, 829.7239, 829.7244, 830.5887, 830.6537, 830.7359, 831.575, 831.5999, 831.6002, 831.7409, 832.5765, 832.6028, 832.6039, 835.6996, 836.7063, 837.5884, 837.7182, 838.7227, 839.7321, 847.5955, 850.703, 851.5689, 851.7111, 852.5725, 852.7198, 852.7242, 853.5854, 853.7252, 854.5887, 855.6013, 856.6046, 856.6697, 857.617, 857.6733, 858.6847, 859.6877, 861.5265, 861.7174, 861.7808, 862.7228, 863.6874, 863.7339, 864.738, 865.7482, 866.7527, 867.7576, 871.5528, 872.5556, 873.5684, 876.7223, 877.7271, 878.7381, 879.598, 879.742, 880.7528, 880.7555, 881.7568, 881.7609, 882.7673, 882.7717, 883.7715, 884.7817, 884.7873, 885.7867, 885.7919, 886.5582, 886.8027, 887.5625, 887.8022, 893.774, 894.7273, 894.7813, 895.5578, 895.559, 895.7335, 895.7873, 896.745, 897.573, 897.75, 898.7605, 899.5871, 899.7663, 900.5897, 902.737, 903.7407, 904.7535, 905.7573, 906.769, 907.7735, 908.708, 908.7842, 908.7843, 909.7153, 909.7892, 910.7248, 910.7979, 911.7326, 912.7412, 913.7502, 914.7577, 915.7673, 916.774, 917.7836, 918.7901, 919.7981, 920.747, 920.8054, 921.753, 921.8145, 922.7656, 922.8229, 923.5884, 923.7675, 924.7826, 926.7371, 928.7519, 930.7673, 931.7691, 931.793, 932.7819, 934.7235, 935.7299, 936.7387, 937.7457, 938.7553, 939.7616, 940.7709, 941.7779, 942.7876, 943.7931, 944.8033, 945.8085, 946.8187, 950.7385, 952.7568, 952.7759, 954.7905, 962.7616, 964.7764, 965.7839, 966.7933, 967.7981, 968.8072, 1016.929, 1017.934, 1018.943, 1019.95, 1040.934, 1225.093, 1226.098, 1227.107, 1228.113, 1229.118, 1251.115, and 1253.129, and a decrease in the accurate mass intensity at one or more of said accurate masses in the blood sample from the patient relative to the reference indicates that the patient has prostate cancer or is at risk of prostate cancer; and wherein the hydrogen and electron adjusted accurate masses or neutral accurate masses at which intensity increases are: 202.0454, 205.8867, 216.0401, 218.0372, 226.0687, 228.1476, 243.0719, 244.056, 247.9578, 273.874, 283.9028, 317.9626, 326.2476, 328.2628, 331.8326, 339.9964, 341.8614, 351.8906, 354.1668, 382.2903, 472.3925, 473.3957, 552.3825, 582.2469, 583.2504, 736.2234, 776.6069, 783.6349, 997.3968, 1176.777 and 1373.744, and an increase in the accurate mass intensity at one or more of said accurate masses in the blood sample from the patient relative to the reference indicates that the patient has prostate cancer or is at risk of prostate cancer.

2. The method of claim 1, wherein the accurate mass intensities represent ionized metabolites.

3. The method of claim 1, further comprising analyzing at least one sample from said patient by mass spectrometry to obtain accurate mass intensity data for one or more than one internal control metabolite; and calculating a ratio for each of the accurate mass intensities obtained in step (a) to the accurate mass intensities obtained for the one or more than one internal control metabolite;

wherein the comparing step (b) comprises comparing each ratio to one or more corresponding ratios obtained for one or more than one reference sample.

4. The method of claim 1, wherein the hydrogen and electron adjusted accurate mass, or neutral accurate mass, is selected from the group consisting of: a) 495.3328, b) 517.3148, c) 519.3328, d) 521.3480, e) 523.3640, f) 541.3148, g) 545.3460, h) 481.3171, i) 531.3123, j) 541.3422, k) 555.3101, l) 565.3394, m) 567.3546, n) 569.3687 and combinations thereof, and a decrease in accurate mass intensity at one or more of said accurate masses in the blood sample from the patient relative to the reference indicates that the patient has prostate cancer or is at risk of prostate cancer.

5. The method of claim 1, wherein the accurate mass intensity data is obtained using a Fourier transform ion cyclotron resonance, time of flight, orbitrap, quadrupole or triple quadrupole mass spectrometer.

6. The method of claim 1, wherein the blood sample is a whole blood sample, a blood serum sample, or a plasma sample.

7. The method of claim 1, wherein a liquid/liquid extraction is performed on the blood samples whereby non-polar metabolites are dissolved in an organic solvent and polar metabolites are dissolved in an aqueous solvent.

8. The method of claim 1, wherein said one or more than one reference blood sample is a plurality of blood samples obtained from control individuals; one or more than one baseline sample obtained from the patient at an earlier date; or a combination thereof.

9. A method for determining prostate cancer, or the risk of prostate cancer in a patient, the method comprising the steps of:
a) analyzing at least one blood sample from said patient to obtain quantifying data for one or more than one metabolite marker using an analyzer comprising a mass spectrometer;
b) comparing the quantifying data for said one or more than one metabolite marker to corresponding data obtained for one or more than one reference blood sample to identify a decrease in the level of said one or more than one metabolite marker in said blood sample; and
c) using said decrease in the level of said one or more than one metabolite marker in said at least one sample for determining prostate cancer, or the risk of prostate cancer in said patient,
wherein the one or more than one metabolite marker comprises one or more lysophospho lipid selected from the group consisting of: lysophosphatidylcho lines, lysophosphatidylethanolamines, lysophosphatidyl-dimethylethanolamines, lysophosphatidylserines, lysosphingosylphosphoryl-cholines, lysophosphatidylglycerols, lysophosphatidylinositols, platelet activating factors (PAFs), and combinations thereof,
and wherein a decrease in the level of said one or more than one metabolite marker in the blood sample from the patient relative to the reference indicates that the patient has prostate cancer or is at risk of prostate cancer.

10. The method of claim 9, wherein step a) comprises analyzing the blood sample by liquid chromatography mass spectrometry (LC-MS).

11. The method of claim 9, wherein the method is a high-throughput method and step a) comprises analyzing the blood sample by direct injection or liquid chromatography and linear ion trap tandem mass spectrometry.

12. The method of claim 9, further comprising:
analyzing at least one sample from said patient to obtain quantifying data for one or more than one internal control metabolite; and
obtaining a ratio for each of the levels of said one or more than one metabolite marker to the level obtained for the one or more than one internal control metabolite;
wherein the comparing step (b) comprises comparing each ratio to one or more corresponding ratios obtained for the one or more than one reference sample.

13. The method of claim 9, wherein said one or more than one reference blood sample is a plurality of blood samples obtained from control individuals; one or more than one baseline blood sample obtained from the patient at an earlier date; or a combination thereof.

14. The method of claim 9, wherein said lysophospho lipids are lysophosphatidylcho line-related compounds.

15. The method of claim 9, wherein said lysophospholipids are N,N-dimethyl-lysophosphoethanolamine-related compounds.

16. The method of claim 14, wherein the one or more than one metabolite is characterized by
a) at least one MS/MS transition detected in [M+H]$^+$ mode selected from 496, 478, 419, 313, 283, 258, 239, 184, 166, 104, or 86 for molecular formula $C_{24}H_{51}NO_7P^+$;
b) at least one MS/MS transition detected in [M+H]$^+$ mode selected from 518, 459, 415, 359, 341, 281, 221, 104, or 86 for molecular formula $C_{26}H_{49}NO_7P^+$;
c) at least one MS/MS transition detected in [M+H]$^+$ mode selected from 520, 502, 461, 445, 281, 221, 184, 166, 124, or 86 for molecular formula $C_{26}H_{51}NO_7P^+$;
d) at least one MS/MS transition detected in [M+H]$^+$ mode selected from 522, 504, 478, 357, 258, 221, 184, 124, 104 or 86 for molecular formula $C_{26}H_{53}NO_7P^+$;
e) at least one MS/MS transition detected in [M+H]$^+$ mode selected from 524, 506, 496, 478, 331, 313, 258, 285, 184, 166, 124, 104 or 86 for molecular formula $C_{26}H_{55}NO_7P^+$;
f) at least one MS/MS transition detected in [M+H]$^+$ mode selected from 542, 483, 284, 225, 184, 104, or 86 for molecular formula $C_{28}H_{49}NO_7P^+$; or
g) at least one MS/MS transition detected in [M+H]$^+$ mode selected from 546, 528, 514, 487, 104, or 86 for molecular formula $C_{28}H_{53}NO_7P^+$.

17. The method of claim 15, wherein the one or more than one metabolite is characterized by:
j) at least one MS/MS transition detected in [M−H]$^-$ mode selected from 540, 480, 255, 242, 224, 168, 153 or 79 for molecular formula $C_{25}H_{51}NO_9P^-$;
l) at least one MS/MS transition detected in [M−H]$^-$ mode selected from 564, 504, 454, 279, 242, 224, 168, 153, or 79 for molecular formula $C_{27}H_{51}NO_9P^-$;
m) at least one MS/MS transition detected in [M−H]$^-$ mode selected from 566, 506, 281, 242, 224, 168, 153, or 79 for molecular formula $C_{27}H_{53}NO_9P^-$; or
n) at least one MS/MS transition detected in [M−H]$^-$ mode selected from 568, 508, 283, 242, 224, 168, 153 or 79 for molecular formula $C_{27}H_{55}NO_9P^-$.

18. The method of claim 9, wherein the one or more than one metabolite is characterized by the structure

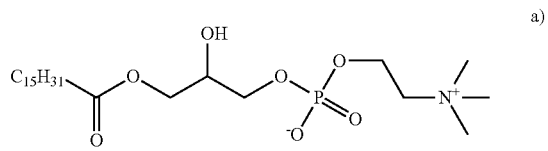

a)

-continued

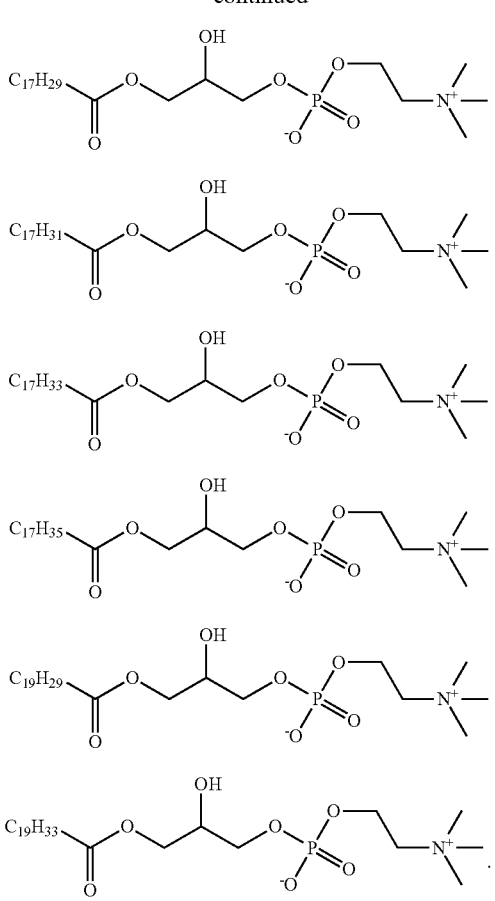

19. The method of claim 9, wherein the quantifying data is obtained using a Fourier transform ion cyclotron resonance, time of flight, orbitrap, quadrupole or triple quadrupole mass spectrometer.

20. The method of claim 19, wherein the mass spectrometer is equipped with a chromatographic system.

21. The method of claim 20, wherein the chromatographic system is a liquid or gas chromatographic system.

22. The method of claim 9, wherein the blood sample is a whole blood sample, a blood serum sample, or a blood plasma sample.

23. The method of claim 9, wherein a liquid/liquid extraction is performed on the blood samples whereby non-polar metabolites are dissolved in an organic solvent and polar metabolites are dissolved in an aqueous solvent.

24. The method of claim 23, wherein the extracted samples are analyzed by positive or negative electrospray ionization, positive or negative atmospheric pressure chemical ionization, or a combination thereof.

25. The method of claim 1, wherein the accurate mass intensity is measured, in Daltons, at the hydrogen and electron adjusted accurate mass or neutral accurate mass ±1 ppm.

26. The method of claim 1, wherein the method is for determining prostate cancer in a patient.

27. The method of claim 1, wherein the method is for determining the risk of prostate cancer in a patient.

28. The method of claim 9, wherein the method is for determining prostate cancer in a patient.

29. The method of claim 9, wherein the method is for determining the risk of prostate cancer in a patient.

30. A method for determining prostate cancer, or the risk of prostate cancer in a patient, the method comprising the steps of:
   a) analyzing at least one blood sample from said patient by high resolution mass spectrometry to obtain accurate mass intensity data;
   b) comparing the accurate mass intensity data to corresponding data obtained from one or more than one reference blood sample to identify an increase or decrease in accurate mass intensity; and
   c) using said increase or decrease in accurate mass intensity to determine prostate cancer or the risk of prostate cancer in said patient,
   wherein the accurate mass intensity is measured, in Daltons, at the hydrogen and electron adjusted accurate mass or neutral accurate mass of 519.3328±5 ppm and wherein a decrease in the accurate mass intensity of 519.3328 in the blood sample from the patient relative to a reference blood sample indicates that patient has prostate cancer or is at risk of prostate cancer.

* * * * *

UNITED STATES PATENT AND TRADEMARK OFFICE
CERTIFICATE OF CORRECTION

PATENT NO. : 8,409,794 B2  
APPLICATION NO. : 12/294215  
DATED : April 2, 2013  
INVENTOR(S) : Ritchie et al.

Page 1 of 1

It is certified that error appears in the above-identified patent and that said Letters Patent is hereby corrected as shown below:

In the Claims:

In claim 9, at col. 75, line 43, delete "lysophospho lipid" and insert --lysophospholipid--; and at col. 75, line 44, delete "lysophosphatidylcho lines" and insert --lysophosphatidylcholines--.

In claim 14, at col. 76, lines 10-11, delete "lysophospho lipids" and insert --lysophospholipids--; and at col. 76, line 11, delete "lysophosphatidylcho line-related" and insert --lysophosphatidylcholine-related--.

Signed and Sealed this
Second Day of July, 2013

Teresa Stanek Rea
*Acting Director of the United States Patent and Trademark Office*